US008053553B2

(12) United States Patent
Strongin et al.

(10) Patent No.: US 8,053,553 B2
(45) Date of Patent: Nov. 8, 2011

(54) TARGETING HOST PROTEINASES AS A THERAPEUTIC STRATEGY AGAINST VIRAL AND BACTERIAL PATHOGENS

(75) Inventors: Alex Strongin, La Jolla, CA (US); Michal Lebl, San Diego, CA (US); Robert Day, Lonchamp (CA)

(73) Assignees: Socpra Sciences Sante Et Humaines, Sherbrooke, Quebec (CA); Illumina, Inc., San Diego, CA (US); Sanford-Burnham Medical Research Institute, La Jolla, CA (US)

( * ) Notice: Subject to any disclaimer, the term of this patent is extended or adjusted under 35 U.S.C. 154(b) by 463 days.

(21) Appl. No.: 12/115,083

(22) Filed: May 5, 2008

(65) Prior Publication Data
US 2009/0029924 A1     Jan. 29, 2009

Related U.S. Application Data

(60) Provisional application No. 60/917,043, filed on May 9, 2007.

(51) Int. Cl.
C07K 4/00 (2006.01)
C07K 14/00 (2006.01)
A61K 39/12 (2006.01)
(52) U.S. Cl. ..... 530/300; 530/350; 530/328; 536/23.72; 536/23.7; 514/20.1
(58) Field of Classification Search ........................ None
See application file for complete search history.

(56) References Cited

U.S. PATENT DOCUMENTS
2005/0089526 A1*   4/2005   Moore et al. ............... 424/188.1

OTHER PUBLICATIONS

Rodriguez-Lopez et al., Immunogenicity of variable regions of hepatitis C virus proteins: selection and modification of peptide epitopes to assess hepatitis C virus genotypes by ELISA, 1999, Journal of General Virology, vol. 80, pp. 727-738.*
Basak, et al Implication of the proprotein convertases furin, PC5 and PC7 in the cleavage of surface glycoproteins of Hong Kong, Ebola and respiratory syncytial viruses: a comparative analysis with fluorogenic peptides Biochem J 353:537-45 2001.
Bucci et al, In vivo delivery of the caveolin-1 scaffolding domain inhibits nitric oxide synthesis and reduces inflammation Nat. Med. 6:1362-1367, 2000.
Chen, et al Structure of the hemagglutinin precursor cleavage site, a determinant of influenza pathogenicity and the origin of the labile conformation Cell 95:409-17 1998.
Chiron, et al Furin-mediated cleavage of Pseudomonas exotoxin-derived chimeric toxins. J Biol Chem 272:31707-11 1997.
Collier, et al Anthrax toxin J Annu Rev Cell Dev Biol 19:45-70, 2003.
Derossi, et al Cell internalization of the third helix of the Antennapedia homeodomain is receptor-independent. J Biol Chem 271:18188-93, 1996.
Elmquist, et al VE-cadherin-derived cell-penetrating peptide, pVEC, with carrier functions Exp. Cell Res. 269:237-244, 2001.
Fischer, et al, Structure activity relationship of truncated and substituted analogues of the intracellular delivery vector Penetratin. J Pept Res 55:163-72, 2000.
Fogle, et al Anti-ETA IgG neutralizes the effects of Pseudomonas aeruginosa exotoxin A.J Surg Res 106:86-98, 2002.
Forino, et al Efficient synthetic inhibitors of anthrax lethal factor Proc Natl Acad Sci USA 102:9499-504, 2005.
Frankel, et al, Cellular uptake of the tat protein from human immunodeficiency virus Cell 55:1189-1193, 1988.
Fugere, et al Inhibitory potency and specificity of subtilase-like pro-protein convertase (SPC) prodomains J Biol Chem 277:7648-56, 2002.
Fugere, et al Trends Pharmacol Sci Cutting back on pro-protein convertases: the latest approaches to pharmacological inhibition 26:294-301, 2005.
Gao, et al. A cell-penetrating peptide from a novel pVII-pIX phage-displayed random peptide library Bioorg. Med. Chem. 10:4057-4065, 2002.
Green, et al, Autonomous functional domains of chemically synthesized human immunodeficiency virus tat trans-activator protein Cell 55:1179-1188, 1988.
Hachmann, et al, Alternative to piperidine in Fmoc solid-phase syntheses J Comb Chem 8:149, 2006.
Hachmann, et al, Search for optimal coupling reagent in multiple peptide synthesizer Biopolymers 84:340-7, 2006.
Hong, et al. Isolation of a peptide for targeted drug delivery into human head and neck solid tumors Cancer Res. 60:6551-6556, 2000.
Jiao, et al, Synthetic small molecule furin inhibitors derived from 2,5-dideoxystreptamine Pro Natl Acad Sci U S A 103:19707-12, 2006.
King, et al, A cleavage method which minimizes side reactions following Fmoc solid phase peptide synthesis Int J Pept Protein Res 36:255-66, 1990.
Kozlov, et al, A method for rapid protease substrate evaluation and optimization Comb Chem High Throughput Screen 9:481-7, 2006.
Lin, et al Synthesis and properties of water-soluble core-shell-shell silica-CdSe/CdS-silica nonparticles. J Nanosci Nanotechnol 6:1092-100, 2006.
Lundberg, et al. Cell membrane translocation of the N-terminal (1-28) part of the prion proteinBiochem. Biophys. res. Commun. 299:85-90, 2002.
Morris, et al A peptide carrier for the delivery of biologically active proteins into mammalian cells. Nature Bio. 19:1173-1176, 2001.
Oehlke, et al, Cellular uptake of an alpha-helical amphipathic model peptide with the potential to deliver polar compounds into the cell interior non-endocytically Biochim Biophys Acta 1414:127-139, 1998.
Park, et al, Structure-activity analysis of buforin II, a histone H2A-derived antimicrobial peptide: the proline hinge is responsible for the cell-penetrating ability of buforin II Proc Natl Acad Sci USA 97:8245-8250, 2000.
Pooga, et al, Cell penetration by transportan FASEB J 12:67-77, 1998.

(Continued)

*Primary Examiner* — Mary E Mosher
*Assistant Examiner* — Benjamin P Blumel
(74) *Attorney, Agent, or Firm* — Pabst Patent Group LLP

(57) ABSTRACT

Disclosed are compositions and methods for preventing or reducing harm resulting from pathogen infection. For example, disclosed are peptides that inhibit the processing of toxins normally cleaved by proprotein convertase enzymes.

21 Claims, 10 Drawing Sheets

OTHER PUBLICATIONS

Remacle, et al, Furin regulates the intracellular activation and the uptake rate of cell surface-associated MT-1-MMP. Oncogene 25:5648-55, 2006.

Rouselle et al. New advances in the transport of doxorubicin through the blood-brain barrier by a peptide vector-mediated strategy. Mol. Pharmacol. 57:679-686, 2000.

Sabet, et al, Modulation of cytokine production and enhancement of cell viability by TLR7 ligands during anthrax infection of macrophages, FEMS Immunol Med Microbiol 47:369-79, 2006.
Sawada, et al. Cytoprotective membrane-permeable peptides designed from the Bax-binding domain of Ku70. Nature Cell Biol. 5:352-357, 2003.
Scamuffa, et al, Proprotein convertases: lessons from knockouts FASEB J 20:1954-63, 2006.
Shiryaev, et al, Cleavage preference distinguishes the two-component NS2B-NS3 serine proteinases of Dengue and West Nile viruses Biochem J 401:743-52, 2007.
Stevens, et al Structure of the uncleaved human H1 hemagglutinin from the extinct 1918 influenza virus Science 303:1866-70, 2004.
Subbarao, et al Characterization of an avian influenza A (H5N1) virus isolated from a child with a fatal respiratory illness. Science 279:393-396, 1998.
Vigneron, et al Guanidinium-cholesterol cationic lipids: efficient vectors for the transfection of eukaryotic cells. Proc. Natl. Acad. Sci. USA 93:9682-9686, 1996.
Wu, et al Immunotherapeutic activity of a novel conjugate of a toll-like receptor 7 ligand. PNAS 104:3990-3995, 2007.
Yang, et al Magnetite-containing spherical silica nanoparticles for biocatalysis and bioseparations. Anal Chem 76:1316-21, 2004. Erratum in: Anal Chem 77:354, 2005.
International Search Report and Written Opinion for PCT/US08/062654 (24520.5.9001) mailed May 5, 2009.
International Preliminary Report on Patentability for PCT/US08/062654 (24520.5.9001) mailed Dec. 7, 2009.

* cited by examiner

|  |  | Ki, µM |
|---|---|---|
| TPRERRRKKRG | SEQ ID NO:109 | >0.1 |
| APRERRRKKRG | SEQ ID NO:25 | >0.1 |
| TARERRRKKRG | SEQ ID NO:26 | >0.1 |
| TPAERRRKKRG | SEQ ID NO:27 | >0.1 |
| TPRARRRKKRG | SEQ ID NO:28 | 0.057 |
| TPREARRKKRG | SEQ ID NO:29 | >0.1 |
| TPRERARKKRG | SEQ ID NO:30 | >0.1 |
| TPRERRAKKRG | SEQ ID NO:31 | >0.1 |
| TPRERRRAKRG | SEQ ID NO:32 | >0.1 |
| TPRERRRKARG | SEQ ID NO:33 | >0.1 |
| TPRERRRKKAG | SEQ ID NO:34 | >0.1 |

|  |  | Ki, µM |
|---|---|---|
| TPGRRRKKRG | SEQ ID NO:94 | 0.047 |
| TPRARRRKKRG | SEQ ID NO:28 | 0.057 |
| TPRVRRRKKRG | SEQ ID NO:95 | >0.1 |
| TPRLRRRKKRG | SEQ ID NO:96 | >0.1 |
| TPRIRRRKKRG | SEQ ID NO:97 | >0.1 |
| TPRPRRRKKRG | SEQ ID NO:98 | >0.1 |
| TPRFRRRKKRG | SEQ ID NO:99 | >0.1 |
| TPRWRRRKKRG | SEQ ID NO:100 | >0.1 |
| TPRMRRRKKRG | SEQ ID NO:101 | >0.1 |
| TPRSRRRKKRG | SEQ ID NO:102 | >0.1 |
| TPRTRRRKKRG | SEQ ID NO:103 | >0.1 |
| TPRCRRRKKRG | SEQ ID NO:104 | >0.1 |
| TPRYRRRKKRG | SEQ ID NO:105 | >0.1 |
| TPRNRRRKKRG | SEQ ID NO:106 | >0.1 |
| TPRQRRRKKRG | SEQ ID NO:107 | >0.1 |
| TPRDRRRKKRG | SEQ ID NO:108 | >0.1 |
| TPRERRRKKRG | SEQ ID NO:109 | >0.1 |
| TPRHRRRKKRG | SEQ ID NO:111 | >0.1 |
| TPRKRRRKKRG | SEQ ID NO:112 | >0.1 |
| TPRRRRRKKRG | SEQ ID NO:113 | >0.1 |
| TPR1RRRKKRG | SEQ ID NO:114 | >0.1 |
| TPR2RRRKKRG | SEQ ID NO:115 | >0.1 |
| TPR3RRRKKRG | SEQ ID NO:116 | >0.1 |
| TPR4RRRKKRG | SEQ ID NO:117 | >0.1 |
| TPReRRRKKRG | SEQ ID NO:118 | >0.1 |
| TPRkRRRKKRG | SEQ ID NO:119 | >0.1 |

|  |  | Ki, µM |
|---|---|---|
| TPRARRRKKRG | SEQ ID NO:28 | 0.057 |
| TPRARRRKKRA | SEQ ID NO:203 | >0.1 |
| TPRARRRKKRV | SEQ ID NO:204 | 0.080 |
| TPRARRRKKRL | SEQ ID NO:205 | >0.1 |
| TPRARRRKKRI | SEQ ID NO:206 | 0.030 |
| TPRARRRKKRP | SEQ ID NO:207 | >0.1 |
| TPRARRRKKRF | SEQ ID NO:208 | 0.038 |
| TPRARRRKKRW | SEQ ID NO:209 | 0.059 |
| TPRARRRKKRM | SEQ ID NO:210 | >0.1 |
| TPRARRRKKRS | SEQ ID NO:211 | >0.1 |
| TPRARRRKKRT | SEQ ID NO:212 | 0.023 |
| TPRARRRKKRC | SEQ ID NO:213 | >0.1 |
| TPRARRRKKRY | SEQ ID NO:214 | 0.053 |
| TPRARRRKKRN | SEQ ID NO:215 | 0.045 |
| TPRARRRKKRQ | SEQ ID NO:216 | 0.047 |
| TPRARRRKKRD | SEQ ID NO:217 | 0.056 |
| TPRARRRKKRE | SEQ ID NO:218 | >0.1 |
| TPRARRRKKRH | SEQ ID NO:219 | >0.1 |
| TPRARRRKKRK | SEQ ID NO:220 | >0.1 |
| TPRARRRKKRR | SEQ ID NO:221 | >0.1 |
| TPRARRRKKR5 | SEQ ID NO:222 | 0.065 |
| TPRARRRKKR6 | SEQ ID NO:223 | 0.081 |

FIG.1A

| PEPTIDE | SEQ ID | FURIN | PACE4 | Ki, µM PC4 | PC5/6 | PC7 |
|---|---|---|---|---|---|---|
| TPRARRRKKRI | SEQ ID NO:206 | 0.030 | 0.026 | 0.562 | 0.492 | 0.135 |
| TPRARRRKKRT | SEQ ID NO:212 | 0.023 | 0.162 | 0.441 | 0.232 | 0.152 |
| TPQRARRRKKRT | SEQ ID NO:151 | 0.033 | .0296 | 0.515 | 0.188 | 0.206 |
| TPQRARRRKKRW | SEQ ID NO:148 | 0.034 | 0.192 | 0.952 | 0.433 | 0.172 |
| TPQRARRRKKRF | SEQ ID NO:147 | 0.044 | 0.602 | 0.772 | 0.806 | 1.133 |
| TPQRARRRKKRY | SEQ ID NO:153 | 0.047 | 1.020 | 0.624 | 0.649 | 1.220 |

| | | N-TERMINAL LINKER | | | |
|---|---|---|---|---|---|
| PEPTIDE | SEQ ID | NONE | GGG- | GGGGGG- | GAGAGA- |
| | | | $K_i$, μm | | |
| PEPTIDE ALONE | TPRARRKKRT | SEQ ID NO:212 | 0.023 | 0.039 | 0.066 | 0.047 |
| | TPRARRRKKRF | SEQ ID NO:208 | 0.038 | 0.067 | 0.045 | 0.056 |
| | TPRARRKKRY | SEQ ID NO:214 | 0.047 | 0.042 | 0.054 | 0.057 |
| | TPQRARRRKKRW | SEQ ID NO:148 | 0.034 | 0.067 | 0.088 | 0.127 |
| PEPTIDE ON NANOBEADS | TPRARRKKRT | SEQ ID NO:212 | 4.9 | 1.99 | 2.32 | 2.57 |
| | TPQRARRRKKRW | SEQ ID NO:148 | 3.85 | 4.28 | 9.09 | ND |

FIG.2C

TARGETING HOST PROTEINASES AS A THERAPEUTIC STRATEGY AGAINST VIRAL AND BACTERIAL PATHOGENS

CROSS-REFERENCE TO RELATED APPLICATIONS

This application claims benefit of U.S. Provisional Application No. 60/917,043, filed May 9, 2007, which is hereby incorporated herein by reference in its entirety.

STATEMENT REGARDING FEDERALLY SPONSORED RESEARCH

This invention was made with government support under Grants U01AI056385, U01AI061139, and U54RR020843 awarded by the National Institutes of Health. The government has certain rights in the invention.

REFERENCE TO SEQUENCE LISTING

The Sequence Listing submitted Jun. 2, 2011 as a text file named "SBMRI_5_8402_AMD_AFD_revised_sequence_listing.txt," created on May 13, 2011, and having a size of 105,201 bytes is hereby incorporated by reference pursuant to 37 C.F.R. §1.52(e)(5).

BACKGROUND

Pathogens or their toxins, including hemorrhagic fever and influenza viruses, botulinum, pseudomonas and anthrax toxins, require processing by host proprotein convertases (PCs) to enter host cells and to cause disease. Disclosed herein are inhibitors of proprotein convertases, such as furin, and methods of using these inhibitors to treat and prevent harm caused by viral and bacterial pathogens.

BRIEF SUMMARY

In accordance with the purpose of this invention, as embodied and broadly described herein, this invention relates to compositions and methods for treating or preventing harm caused by natural or weaponized viral or bacterial pathogens.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

In accordance with the purpose of this invention, as embodied and broadly described herein, this invention relates to compositions and methods for treating or preventing harm caused by natural or weaponized viral or bacterial pathogens.

FIG. 1 shows peptides derived from the cleavage motif of hemagglutinin H5 inhibit furin and related proprotein convertases (PCs) both in vitro and in vivo. FIG. 1A shows derivatization and the $K_i$ values of the peptides against furin. Peptides exhibited the free amino-terminus while the C-terminus was amidated. FIG. 1B shows the $K_i$ values of the peptides against PCs.

FIG. 2 shows nanoparticles exhibiting the immobilized peptides inhibit furin in vitro and in cellbased assays. FIG. 2B shows silica nanoparticles (SNPs) with the immobilized peptides inhibit furin cleavage of PA83. A 500 nM concentration of 2000 kDa SNPs was used in the reactions. FIG. 2C shows the N-terminal linkers and the potency of the soluble and immobilized peptides against furin. The N-terminal linkers used were GGG- (SEQ ID NO:226), GGGGGG- (SEQ ID NO:227), and GAGAGA- (SEQ ID NO:228). The $K_i$ values for SNPs were calculated based on the total amount of the immobilized peptide. The $K_i$ values based on the concentrations of the beads were ~2000-fold less.

FIG. 3 shows the TPRARRRKKRT peptide (SEQ ID NO:212) protects mice from the toxic effect of *Pseudomonas* PEx. FIG. 3A right panel shows Furin, PC4 and PC5/6 cleave PEx at pH 5.5. Dec, decanoyl-Arg-Val-Lys-Arg-chloromethylketone. FIG. 3B left panel shows C57/BL6 mice (5 mice/group) received an injection of the peptide (12.5 mg/kg i.p.) one day before injection of PEx (500 ng/animal; $2LD_{50}$). FIG. 3B middle panel shows C57/BL6 mice (5 mice/group) received an injection of the peptide (12.5 mg/kg i.p.) simultaneously with an injection of PEx (500 ng/animal; $2LD_{50}$). FIG. 3B right panel shows C57/BL6 mice (5 mice/group) received an injection of the peptide (12.5 mg/kg i.p.) one day before an injection of PEx (500 ng/animal; $2LD_{50}$) and then animals received daily injections of the peptide for the remainder of the experiment.

DETAILED DESCRIPTION

Figure 1C:
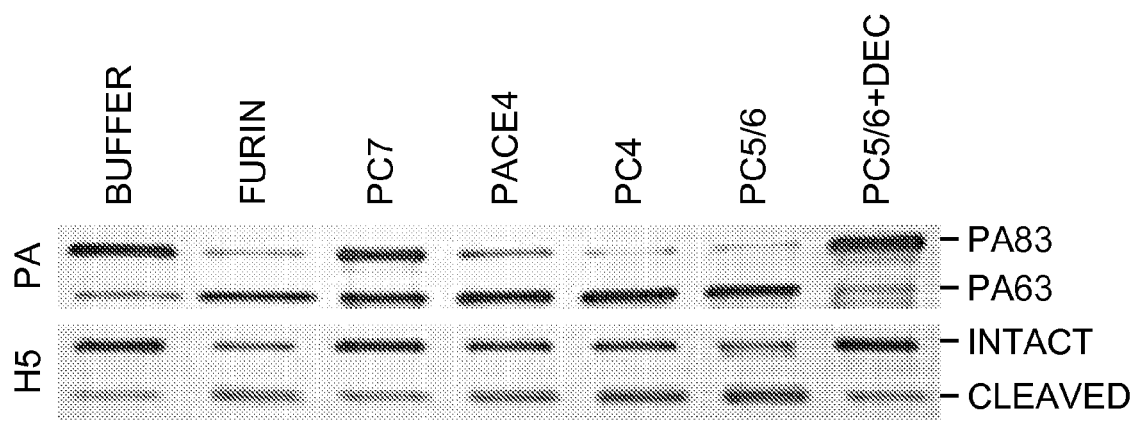
FIG. 1C shows processing of biotin-labeled PA83 and the H5 precursor (500 ng each) by furin and related PCs (one activity unit each).

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Compositions

1. Proprotein Convertase Inhibitors

Provided herein are compounds and compositions that can inhibit protein processing by one or more proprotein convertases (PCs). For example, the disclosed compounds and compositions can inhibit processing of toxins by one or more host proprotein convertases, thus interfering with infection and/or pathology of the pathogen. The disclosed compounds and compositions that inhibit proprotein convertases can be referred to as proprotein convertases.

A proprotein convertase inhibitor, as used herein, is any compound or composition that can inhibit the ability of one or more proprotein convertases to cleave one or more of their substrates. For example, a proprotein convertase inhibitor can in some aspects inhibit the ability of furin to cleave a peptide comprising the amino acid sequence SEQ ID NO:24. Proprotein convertase inhibitors can also be referred to as inhibitors of any or all of the respective proprotein convertase against which the inhibitor is effective. Thus, for example, a proprotein convertase inhibitor that can inhibit furin can be referred to as a furin inhibitor. This is the case regardless of whether the inhibitor inhibits only furin or can also inhibit other proprotein convertases.

Useful proprotein convertases include peptides. Thus, in some aspects, disclosed are isolated peptides that can inhibit proprotein convertase activity. In some aspects, the disclosed isolated peptide is modeled from the cleavage motif of avian influenza H5 hemagglutinin. Thus, for example, the isolated peptide can comprise the amino acid sequence R-X-R/K-R (SEQ ID NO:24). For example, the isolated peptide can comprise the amino acid sequence $X_1RX_2RRRKKRX_3$, wherein $X_1$ is TP (threonine-proline) or TPQ (threonine-proline-glutamine), wherein $X_2$ is A (alanine) or G (glycine), and $X_3$ is any or no amino acid (SEQ ID NOs:346, 371, 372 and 373). In preferred aspects, the isolated peptide can be administered to a subject and is therefore non-toxic.

As used herein, the term "peptide" is meant to include both short and long amino acid polymers. Thus, the terms "peptide" and "polypeptide" are used interchangeably herein. Thus, the disclosed peptide can be at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, or more amino acids in length. Thus, the disclosed peptide can be less than about 100, 95, 90, 85, 80, 75, 70, 65, 60, 55, 50, 45, 40, 35, 30, 25, 20, or 15 amino acids in length.

One advantage of the disclosed peptides is the ability to bind proprotein convertases such as furin. In preferred aspects, the disclosed peptides can sequester proprotein convertases such as furin and thereby inhibit processing of toxins by said proprotein convertases. Thus, the disclosed peptide can bind a proprotein convertase such as furin. In some aspects, the disclosed peptide is not cleaved by a proprotein convertase such as furin.

Numerous examples of the disclosed peptides are described and provided herein. Thus, for example, provided is a peptide comprising the amino acid sequence SEQ ID NO:5. Also provided is a peptide comprising the amino acid sequence SEQ ID NO:28. Also provided is a peptide comprising the amino acid sequence SEQ ID NO:51. Also provided is a peptide comprising the amino acid sequence SEQ ID NO:94. Also provided is a peptide comprising the amino acid sequence SEQ ID NO:142. Also provided is a peptide comprising the amino acid sequence SEQ ID NO:143. Also provided is a peptide comprising the amino acid sequence SEQ ID NO:147. Also provided is a peptide comprising the amino acid sequence SEQ ID NO:148. Also provided is a peptide comprising the amino acid sequence SEQ ID NO:149. Also provided is a peptide comprising the amino acid sequence SEQ ID NO:151. Also provided is a peptide comprising the amino acid sequence SEQ ID NO:153. Also provided is a peptide comprising the amino acid sequence SEQ ID NO:156. Also provided is a peptide comprising the amino acid sequence SEQ ID NO:164. Also provided is a peptide comprising the amino acid sequence SEQ ID NO:204. Also provided is a peptide comprising the amino acid sequence SEQ ID NO:206. Also provided is a peptide comprising the amino acid sequence SEQ ID NO:208. Also provided is a peptide comprising the amino acid sequence SEQ ID NO:209. Also provided is a peptide comprising the amino acid sequence SEQ ID NO:212. Also provided is a peptide comprising the amino acid sequence SEQ ID NO:214. Also provided is a peptide comprising the amino acid sequence SEQ ID NO:215. Also provided is a peptide comprising the amino acid sequence SEQ ID NO:216. Also provided is a peptide comprising the amino acid sequence SEQ ID NO:217. Also provided is a peptide comprising the amino acid sequence SEQ ID NO:222. Also provided is a peptide comprising the amino acid sequence SEQ ID NO:223. Also provided is a peptide comprising the amino acid sequence SEQ ID NO:365. Also provided is a peptide comprising the amino acid sequence SEQ ID NO:366. Also provided is a peptide comprising the amino acid sequence SEQ ID NO:367. Also provided is a peptide comprising the amino acid sequence SEQ ID NO:368. Also provided is a peptide comprising the amino acid sequence SEQ ID NO:369. Also provided is a peptide comprising the amino acid sequence SEQ ID NO:370.

Also provided is an isolated peptide comprising 2, 3, 4, 5, 6, 7, 8, 9, 10 or more of the amino acid sequences disclosed herein. Thus, for example, provided is an isolated peptide comprising 2, 3, 4, 5, 6, 7, 8, 9, 10 or more of the sequences set forth in SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, SEQ ID NO:223, SEQ ID NO:365, SEQ ID NO:366, SEQ ID NO:367, SEQ ID NO:368, SEQ ID NO:369, or SEQ ID NO:370

The sequences can be contiguous or separated by linker sequences. The peptide can be linear or branched.

Also contemplated is the use of amino acid analogues in and/or as part of the disclosed peptides. For example, molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH—(cis and trans), —$COCH_2$—, —$CH(OH)CH_2$—, and —$CHH_2SO$-(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

It has been discovered that the disclosed peptides can inhibit a plurality of proprotein convertases. For example, the disclosed peptides can inhibit two, three, four, five, six or more PCs. The disclosed peptides can inhibit at least two, at least three, at least four, at least five, or at least six PCs. As used herein, inhibit in the context of PCs refers to a reduction of cleavage by the PC of a detectable amount in the presence of an inhibitor as compared to a control level of cleavage in the absence of the inhibitor. For example, the activity of a PC can be inhibited by, for example, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or more. The activity of a PC can be inhibited by, for example, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%. The activity of a PC can be inhibited by, for example, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%. The activity of a PC when inhibited can be, for example, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the control level of activity for the PC. The activity of a PC when inhibited can be, for example, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% or less of the control level of activity for the PC. The activity of a PC when inhibited can be, for example, less than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the control level of activity for the PC. Where a plurality of PCs are inhibited by the disclosed peptides, the different PCs can be inhibited by the same or different amounts. Particularly useful peptides have at least a threshold level of inhibition, inhibit at least a threshold number of PCs, or a combination.

The disclosed peptides can also comprise additional parts, components, moieties or features other than amino acids and amino acid analogues. Any of the peptides disclosed herein can be included or excluded for use as a furin or proprotein convertase inhibitors, either individually or as groups or sets. Thus, for example, the furin inhibitor decanoyl-Arg-Val-Lys-Arg-chloromethylketone (DEC-RVKR-CMK) can be included or excluded.

The proprotein convertase inhibitor also can be a small molecule. For example, small molecule proprotein convertase inhibitors based on 2,5-dideoxystreptamine are disclosed in Jiao, G., et al. (Proc Natl Acad Sci USA. 2006 Dec. 26; 103(52):19707-12).

The proprotein convertase inhibitor also can be an antibody. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro, e.g., using the HIV Env-CD4-co-receptor complexes described herein.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

2. Pathogens

Disclosed herein is a broad-spectrum therapy against natural and pathogens, such as those involving toxins that require processing by host proprotein convertases (PCs) to enter host cells and to cause disease. Examples of such pathogens are disclosed herein. However, it is understood that other pathogens known or discovered to require processing by proprotein convertases can also be affected by the disclosed compositions and methods.

For example the pathogen can be a bacterial pathogen such as Anthrax, *Pseudomonas*, *Botulism*, *Diptheria*, *Aeromonas*, or *Shigella*. Alternatively, the pathogen can be a viral pathogen such as Influenzavirus A, parainfluenza, Sindbis virus, Newcastle disease virus, flavivirus, cytomegalovirus, herpesvirus, HIV, Measles virus, infectious bronchitis virus, Coronavirus, Marburg virus, Ebola virus, or Epstein-Barr virus.

i. Anthrax

Anthrax is a zoonotic disease caused by *Bacillus anthracis*. There are three types of this disease: cutaneous anthrax, inhalation anthrax, and gastrointestinal anthrax. About 95% of the human anthrax cases in the United States have been in the former category. Cutaneous anthrax develops when a bacterial organism from infected animal tissues becomes deposited under the skin. When a patient does not receive an effective antibiotic, the mortality rate for cutaneous anthrax is 10-20%. With treatment, the mortality rate falls to less than 1%. Inhalation anthrax develops when the bacterial organism is inhaled into the lungs. A progressive infection follows. Since inhalation anthrax is usually not diagnosed in time for treatment, the mortality rate in the United States is 90-100%. A biological attack with anthrax spores delivered by aerosol would cause inhalation anthrax, an extraordinarily rare form of the naturally occurring disease.

The pathogenesis of anthrax is primarily the result of a tripartite toxin. This toxin is composed of three proteins: the protective antigen (PA), the edema factor (EF) and the lethal factor (LF). The three proteins of the anthrax toxin depend on each other for their toxic effect. Each protein is nontoxic on its own, but when combined, these proteins produce the lethal symptoms of anthrax.

Figure 2A:
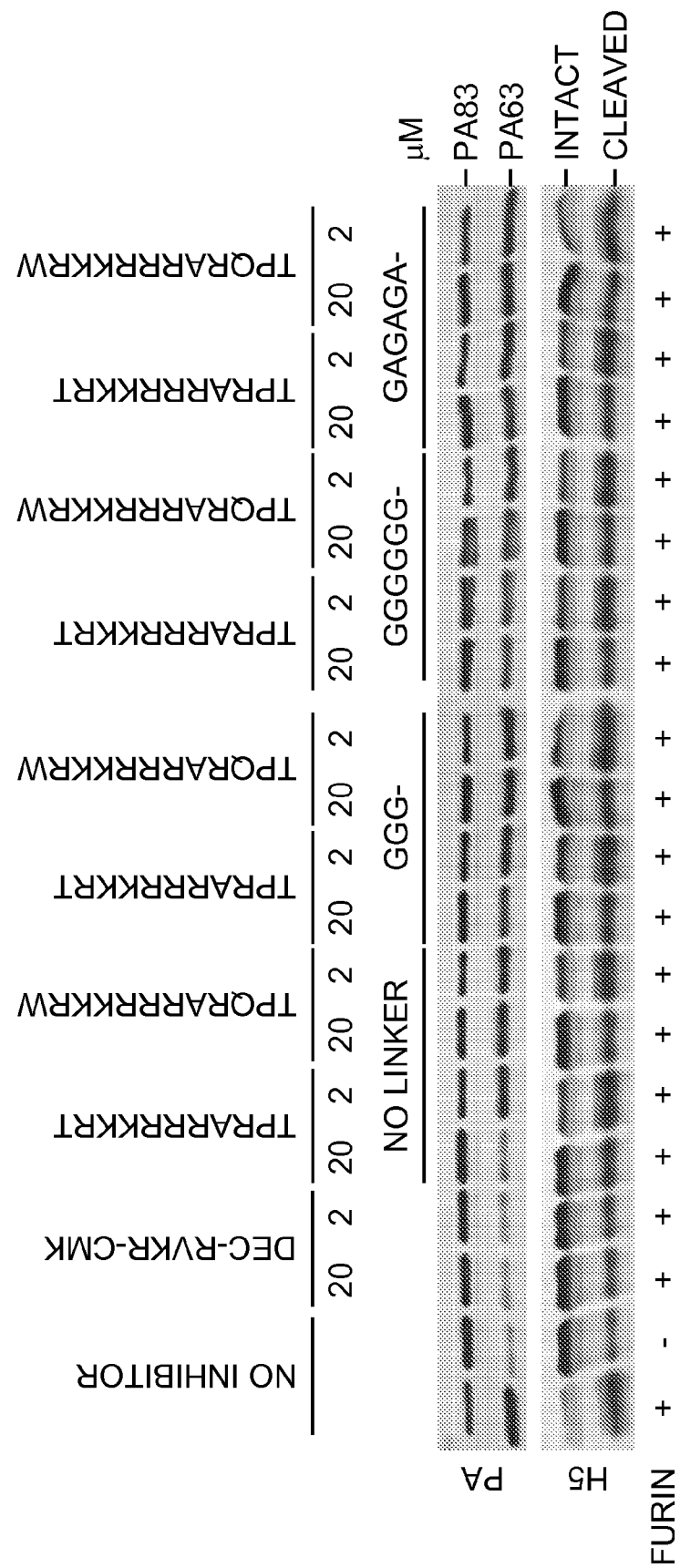
FIG. 2A shows the peptides TPRARRRKKRT (SEQ ID NO:212) and TPQRARRRKKRW (SEQ ID NO:148) without and with the N-terminal linker inhibit processing of biotin-labeled PA83 and H5 (500 ng each).
Figure 2B:
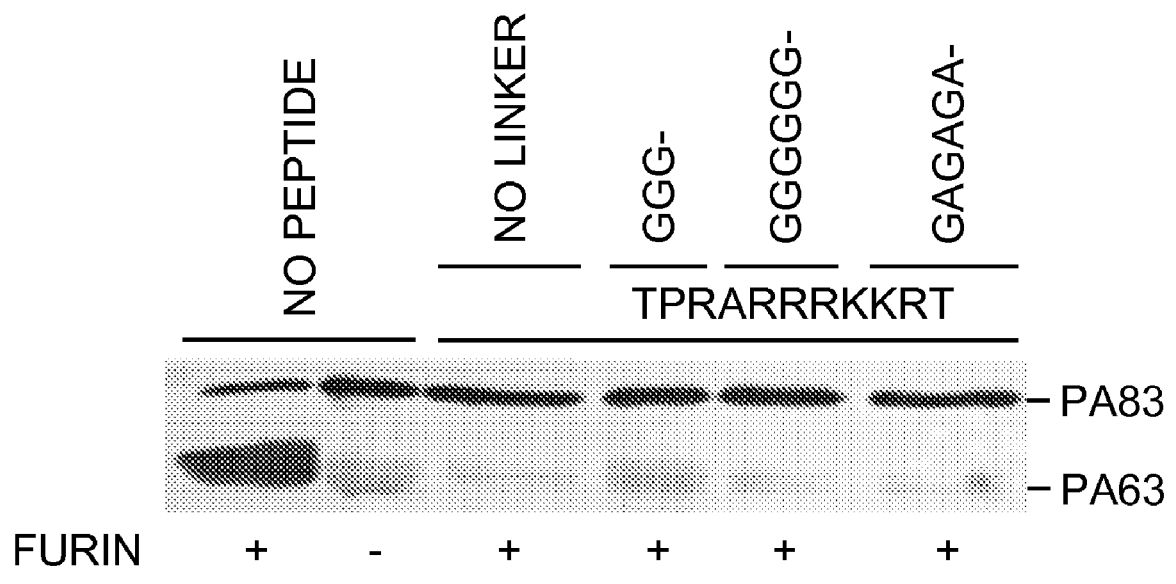

PA is necessary because both LF and EF function inside cells, but they are too large (90.2 kDa and 88.9 kDa, respectively) to enter via existing channels. Through a series of steps, PA helps to shuttle EF and LF into the cell (FIG. 2). This process starts when the 83 kDa PA (PA83) monomers bind to the largely ubiquitous human tumor endothelium marker-8 (TEM8) or capillary morphogenesis protein 2 (CMG2) receptors. Once bound, a 20 kDa N-terminal fragment (PA20) is cleaved off of PA83 by membrane endoproteases from the furin family, exposing binding sites for LF, EF, and other molecules of cleaved PA. Because of this cleavage the remaining 63 kDa portion (PA63) rapidly oligomerizes to form a heptamer pre-pore, which then associates with up to three molecules of EF and/or LF. The cell then endocytoses the complex and carries it to an acidic compartment, where the low pH causes a conformational change in the PA63 pre-pore that forms a cation-specific channel and allows the EF and LF to enter into the cytosol.

Once in the cytosol, the EF and LF then carry out their respective damage-inducing processes. EF acts as a $Ca^{2+}$ and calmodulin dependent adenylate cyclase that greatly increases the level of cAMP in the cell. This increase in cAMP upsets water homeostasis, severely throws the intracellular signaling pathways off balance, and impairs macrophage function, allowing the bacteria to further evade the immune system. LF also helps the bacteria evade the immune system through killing macrophages. Once in these cells, LF acts as a $Zn^{2+}$-dependent endoprotease that snips off the N-terminus of mitogen-activated protein kinase kinases (MAPKK). This inhibits these kinases by not allowing them to efficiently bind to their substrates, which leads to altered signaling pathways and ultimately to apoptosis. Thus, the synergistic effect of these three proteins leads to cellular death through a cascade of events that allow the proteins to enter the cell and disrupt cellular function.

ii. Pseudomonas

Pseudomonas aeruginosa is a Gram-negative, aerobic, rod-shaped bacterium with unipolar motility. An opportunistic pathogen of immunocompromised individuals, *P. aeruginosa* typically infects the pulmonary tract, urinary tract, burns, wounds, and also causes other blood infections. *Pseudomonas* can cause community acquired pneumonias albeit it is uncommon, as well as ventilator-associated pneumonias, being one of the most common agents isolated in several studies. Pyocyanin is a virulence factor of the bacteria and has been known to cause death in *C. elegans* by oxidative stress. However, research indicates that salicylic acid can inhibit pyocyanin production. One in ten hospital-acquired infections are from *Pseudomonas*. Cystic fibrosis patients are also predisposed to *P. aeruginosa* infection of the lungs. *P. aeruginosa* is also the typical cause of "hot-tub rash" (dermatitis), caused by lack of proper, periodic attention to water quality. The most common cause of burn infections is *P. aeruginosa*.

Pseudomonas aeruginosa produces two extracellular protein toxins, Exoenzyme S and Exotoxin A. Exoenzyme S is probably an exotoxin. It has the characteristic subunit structure of the A-component of a bacterial toxin, and it has ADP-ribosylating activity (for a variety of eukaryotic proteins) characteristic of exotoxins. Exoenzyme S is produced by bacteria growing in burned tissue and can be detected in the blood before the bacteria are. It has been suggested that exoenzyme S may act to impair the function of phagocytic cells in the bloodstream and internal organs to prepare for invasion by *P. aeruginosa*.

Exotoxin A has exactly the same mechanism of action as the diphtheria toxin, it causes the ADP ribosylation of eukaryotic elongation factor 2. It is partially-identical to diphtheria toxin, but it is antigenically-distinct. It utilizes a different receptor on host cells, but otherwise it enters cells in the same manner as the diphtheria toxin and it has the exact enzymatic mechanism. Doxtoxin A requires proteolytic cleavage to generate a 37-kDa C-terminal fragment that translocates to the cytosol and ADP-ribosylates elongation factor 2. Cleavage within cells is mediated by furin, occurs between arginine 279 and glycine 280, and requires an arginine at both P1 and P4 residues.

iii. Gas Gangrene

Clostridium perfringens alpha toxin is a toxin produced by the bacterium *Clostridium perfringens* and is responsible for gas gangrene and myonecrosis in infected tissues. The toxin also possesses hemolytic activity. This toxin has been shown to be the key virulence in infection with *C. perfringens*; the bacterium is unable to cause disease without this toxin. Further, vaccination against the alpha toxin toxoid protects mice against *C. perfringens* gas gangrene.

Clostridium septicum alpha-toxin is secreted as an inactive 46,450-Da protoxin. The protoxin is activated by proteolytic cleavage near the C terminus by furin, which eventually causes the release of a 45-amino-acid fragment. Proteoytic activation and loss of the propeptide allow alpha-toxin to oligomerize and form pores on the plasma membrane, which results in colloidal-osmotic lysis.

iv. Diphtheria

Corynebacterium diphtheriae is a pathogenic bacterium that causes diphtheria. *C. diphtheriae* is a facultatively anaerobic Gram positive organism, characterized by non-encapsulated, non-sporulated, immobile, straight or curved rods with a length of 1 to 8 µm and width of 0.3 to 0.8 µm, which form ramified aggregations in culture (looking like "Chinese characters"). Three subspecies *are* recognized: *C. diphtheriae mitis, C. diphtheriae intermedius*, and *C. diphtheriae gravis*. The three subspecies differ slightly in their ability to metabolize certain nutrients, but all may be toxigenic (and therefore cause diphtheria) or non-toxigenic.

Many strains of *C. diphtheriae* produce diphtheria toxin, a proteic exotoxin, with a molecular weight of 62 kilodaltons which ADP-ribosylates host EF-2, which is responsible for the signs of diphtheria. The inactivation of this toxin with an antitoxic serum (antitoxin) is the basis of the antidiphtheric vaccination. However, not all strains are toxigenic; toxin production is associated with infection of the bacterium by a bacteriophage.

Proteolytic cleavage (nicking) of diphtheria toxin (DT) in the 14-amino acid loop subtended by the disulfide bond between Cys186 and Cys201 is required for the cytotoxic action of DT. The loop includes the consensus motif for cleavage by a membrane-anchored furin. In agreement, furin cleaves intact DT between Arg103 and Ser194 in vitro. LoVo cells, a human colon carcinoma cell line, do not produce functional furin. Accordingly, intact DT is not cleaved by LoVo cells. The cells are resistant to intact DT, although they are sensitive to DT nicked by furin before it is added to the medium. When intact DT is added to LoVo/Furl cells, a stable transfectant of LoVo cells expressing mouse furin, nicked DT associated with the cells is observed. LoVo/Furl cells are sensitive to both intact and nicked DT. These results indicate that furin is involved in the toxicity of intact DT. Bafilomycin A1, an inhibitor of intracellular vesicle acidification, did not inhibit cleavage of intact DT by LoVo/Furl or Vero cells, indicating that cleavage can proceed in a neutral environment. Inhibitors of endocytosis decreased DT cleavage but did not eliminate it. Thus, intact DT is cleaved by cell-associated furin on the cell surface as well as in endocytotic vesicles.

v. Aeromonas

The *Aeromonadales* are an order of Proteobacteria, with six genera in two families. *Aeromonas* is a gram-negative, facultative anaerobic rod that morphologically resembles members of the family Enterobacteriaceae. Fourteen species of *Aeromonas* have been described, most of which have been associated with human diseases. The most important pathogens are *A. hydrophila, A. caviae*, and *A. veronii biovar sobria*. The organisms are ubiquitous in fresh and brachish water.

Two major diseases associated with *Aeromonas* are gastroenteritis and wound infections, with or without bacteremia. Gastroentritis typically occurs after the ingestion of contaminated water or food, whereas wound infections result from exposure to contaminated water.

Because of *Aeromonas hydrophila*'s structure, it is very toxic to many organisms. When it enters the body of its victim, it travels through the bloodstream to the first available organ. It produces Aerolysin Cytotoxic Enterotoxin (ACT), a toxin that can cause tissue damage. It is known as a pathogenic bacterium. *Aeromonas hydrophila, Aeromonas caviae,* and *Aeromonas* sobria are all considered to be "opportunistic pathogens," meaning they only infect hosts with weakened immune responses. Though *Aeromonas hydrophila* is considered a pathogenic bacterium, scientists have not been able to prove that it is the actual cause of some of the diseases it is associated with. It is believed that this bacterium aids in the infection of diseases, but do not cause the diseases themselves.

*Aeromonas hydrophila* excretes extracellular proteins which are toxic to other cells. These are aerolysin, glycerophospholipid:cholesterol acyltransferase (GCAT), and serine protease. Another major chemical that contributes to pathogenicity is hemolysin. Aerolysin is secreted as an inactive dimeric precursor. Proteolytic cleavage within a mobile loop near the C terminus of the protoxin is required for oligomerization and channel formation. This loop contains a sequence that is recognized by mammalian proprotein convertases such as furin, PACE4, and PC5/6A.

vi. *Shigella*

*Shigella* are Gram-negative, non-motile, non-spore forming rod-shaped bacteria closely related to *Escherichia coli* and *Salmonella. Shigella* species are classified by four serogroups: Serogroup A: *S. dysenteriae* (12 serotypes), Serogroup B: *S. flexneri* (6 serotypes), Serogroup C: *S. boydii* (23 serotypes), and Serogroup D: *S. sonnei* (1 serotype).

Shiga toxins are a family of related toxins with two major groups, Stx1 and Stx2, whose genes are considered to be part of the genome of lambdoid prophages. The most common sources for Shiga toxin are the bacteria *S. dysenteriae* and the Shigatoxigenic group of *Escherichia coli* (STEC). Shiga toxins act to inhibit protein synthesis within target cells by a mechanism similar to that of ricin toxin produced by *Ricinus communis*. After entering a cell, the protein functions as an N-glycosidase, cleaving several nucleobases from the RNA that comprises the ribosome, thereby halting protein synthesis. The toxin has two subunits—designated A and B—and is one of the AB5 toxins. The B subunit is a pentamer that binds to specific glycolipids on the host cell, specifically globotriaosylceramide (Gb3). Following this, the A subunit is internalised and cleaved into two parts. The A1 component then binds to the ribosome, disrupting protein synthesis.

Shiga toxin is composed of an enzymatically active A-subunit in non-covalent association with a pentamer of B-subunits responsible for binding to cell surface receptors. The A-subunit is a specific N-glycosidase that cleaves off a single adenine residue from 28 S rRNA of the 60 S ribosomal subunit, resulting in inhibition of the protein synthesis. After binding to cell surface receptors, the toxin is endocytosed from clathrin-coated pits. Shiga toxin A-chain (ST-A) contains 2 cysteines that are linked by a disulfide bond. The loop between the 2 cysteines can be cleaved by Furin, separating the A-chain into $A_1$ (~27.5 kDa) and $A_2$ (~4.5 kDa) fragments, thus activating the toxin.

vii. Influenza A

Influenza, commonly known as flu, is an infectious disease of birds and mammals caused by an RNA virus of the family Orthomyxoviridae (the influenza viruses). In humans, common symptoms of influenza infection are fever, sore throat, muscle pains, severe headache, coughing, and weakness and fatigue. In more serious cases, influenza causes pneumonia, which can be fatal, particularly in young children and the elderly. Sometimes confused with the common cold, influenza is a much more severe disease and is caused by a different type of virus.

Typically, influenza is transmitted from infected mammals through the air by coughs or sneezes, creating aerosols containing the virus, and from infected birds through their droppings. Influenza can also be transmitted by saliva, nasal secretions, feces and blood. Infections occur through contact with these bodily fluids or with contaminated surfaces. Flu viruses can remain infectious for about one week at human body temperature, over 30 days at 0° C. (32° F.), and indefinitely at very low temperatures (such as lakes in northeast Siberia).

The influenza virus is an RNA virus of the family Orthomyxoviridae. There are three types of influenza virus: Influenzavirus A, Influenzavirus B, or Influenzavirus C. Influenza A and C infect multiple species, while influenza B almost exclusively infects humans. The type A viruses are the most virulent human pathogens among the three influenza types and cause the most severe disease. The Influenza A virus can be subdivided into different serotypes based on the antibody response to these viruses. The serotypes that have been confirmed in humans, ordered by the number of known human pandemic deaths, are H1N1 (Spanish Flu), H2N2 (Asian Flu), H3N2 (Hong Kong Flu), H5N1 (Avian Flu), H7N7, H1N2, H9N2, H7N2, H7N3, and H10N7.

The influenza A genome is not a single piece of nucleic acid; instead, it contains eight pieces of segmented negative-sense RNA (13.5 kilobases total), which encode 11 proteins (HA, NA, NP, M1, M2, NS1, NEP, PA, PB1, PB1-F2, PB2). The best-characterised of these viral proteins are hemagglutinin (HA) and neuraminidase (NA), two large glycoproteins found on the outside of the viral particles. Neuraminidase is an enzyme involved in the release of progeny virus from infected cells, by cleaving sugars that bind the mature viral particles. By contrast, hemagglutinin is a lectin that mediates binding of the virus to target cells and entry of the viral genome into the target cell. The responses of antibodies to these proteins are used to classify the different serotypes of influenza A viruses, hence the H and N in H5N1. There are at least 16 different HA antigens. These subtypes are labeled H1 through H16.

Although the virulence of avian influenza viruses is polygenic, the susceptibility of the hemagglutinin (HA) to host proteases is the major determinant for this property. That is, influenza virus HA must be cleaved into HA1 and HA2 subunits for the virus to be infectious, as this event generates the amino terminus of HA2, which mediates the fusion of the viral envelope with the endosomal membrane. Lethal and nonlethal avian viruses differ in this mode of activation: the HA of the former is cleaved by the ubiquitous proteases furin and PC6, whereas the HA of the latter is not susceptible to these proteases but rather is cleaved by proteases localized in the respiratory or intestinal organs or both.

viii. Flavivirus

Flaviviruses are small enveloped viruses with a positive-stranded RNA genome. Several of the members of the genus *Flavivirus*, in the family Flaviviridae, are important human pathogens, including Tick-borne encephalitis virus (TBEV), Yellow fever virus, Japanese encephalitis virus, West Nile virus, and the four serotypes of Dengue virus. All of the flaviviruses share very similar structural and functional properties. Their genomic RNA serves as the only viral messenger and encodes all viral proteins in a single long open reading frame. The translation product, a polyprotein, is cleaved by viral and cellular proteases to yield the three structural proteins, C (capsid protein), prM/M (membrane protein and its precursor protein), and E (envelope protein), as well as seven nonstructural proteins. Flavivirus virions consist of a nucleocapsid, which is formed by multiple copies of the basic and mostly alpha-helical protein C encapsulating the genomic RNA, and a surrounding host cell-derived lipid membrane, in which the two surface proteins, prM/M and E, are carboxy-terminally anchored.

Shortly before or concomitant with the final release of the virion from the cell, the immature virion is converted to its mature form by the proteolytic cleavage of protein prM by the cellular proprotein convertase furin. This cleavage event induces a major structural reorganization of the viral particle. The immature particle with its 60 heterodimeric spikes is transformed into the smooth mature virion, which has 90 homodimers of protein E in an icosahedrally symmetric herringbone pattern. The amino-terminal part of protein prM (often referred to as the "pr" part) is lost when prM is cleaved, leaving only the small 8-kDa carboxy-terminal part, protein M, in the viral particle. The "pr" part of protein prM carries major determinants that are important for its role in protecting protein E during exocytosis.

ix. HIV

Human immunodeficiency virus (HIV) is a retrovirus that causes acquired immunodeficiency syndrome (AIDS). This is a condition in humans in which the immune system begins to fail, leading to life-threatening opportunistic infections. Previous names for the virus include human T-lymphotropic virus-III (HTLV-III), lymphadenopathy-associated virus (LAV), and AIDS-associated retrovirus (ARV)

HIV is different in structure from other retroviruses. It is about 120 nm in diameter (120 billionths of a meter; around 60 times smaller than a red blood cell) and roughly spherical. It is composed of two copies of positive single-stranded RNA that codes for the virus's nine genes enclosed by a conical capsid composed of 2,000 copies of the viral protein p24. The single-stranded RNA is tightly bound to nucleocapsid proteins, p7 and enzymes needed for the development of the virion such as reverse transcriptase, proteases, ribonuclease and integrase. A matrix composed of the viral protein p17 surrounds the capsid ensuring the integrity of the virion particle. This is, in turn, surrounded by the viral envelope which is composed of two layers of fatty molecules called phospholipids taken from the membrane of a human cell when a newly formed virus particle buds from the cell. Embedded in the viral envelope are proteins from the host cell and about 70 copies of a complex HIV protein that protrudes through the surface of the virus particle. This protein, known as Env, consists of a cap made of three molecules called glycoprotein (gp) 120, and a stem consisting of three gp41 molecules that anchor the structure into the viral envelope. This glycoprotein complex enables the virus to attach to and fuse with target cells to initiate the infectious cycle.

Of the nine genes that are encoded within the RNA genome, three of these genes, gag, pol, and env, contain information needed to make the structural proteins for new virus particles. env, for example, codes for a protein called gp160 that is broken down by the proprotein convertase furin to form gp120 and gp41. HIV-1 infectivity is strictly dependent on the processing of gp160 to gp120/gp41. The gp120 component promotes the binding of the gp120/gp41 complex to CD4 molecules on target cells, whereas the NH2-terminal 28 residues of the associated gp41 confer the fusogenic properties of the protein. The processing, and hence the bioactivities of both proproteins, show an absolute dependence on the integrity of the consensus furin site.

x. Filoviruses

Filoviruses are viruses belonging to the family Filoviridae, which is in the order Mononegavirales. These viruses are single stranded negative sense RNA viruses that target primates. There are two general viruses, the Ebola virus (Ebolavirus, with four species) and the Marburg virus (Marburgvirus).

These viruses cause horrific viral hemorrhagic fevers, characterized by bleeding and coagulation abnormalities including diffuse bleeding. Ebola destroys the immune system in an explosive manner. Marburg virus typically has a mortality rate of at least 25%, while Ebola virus, depending on the species, has a mortality rate of anywhere from 50% to 90%. The virus is spread through bodily fluids. They are classified by the Centers for Disease Control and Prevention as Biosafety Level 4. This means that they are among the most lethal and destructive viruses known to man.

Ebola virus, a filamentous, enveloped, negative-strand RNA virus in the family Filoviridae, causes severe hemorrhagic fever in humans and nonhuman primates. The fourth gene from the 3' end of its nonsegmented genome encodes two glycoproteins: the nonstructural secretory glycoprotein (SGP), which is secreted from infected cells and is the primary product of the gene, and the envelope glycoprotein (GP), which is responsible for cell binding and penetration of the virus. The latter is expressed by transcriptional editing, resulting in the addition of an extra adenosine within a stretch of seven adenosines in the coding region of GP. These glycoproteins have different proclivities for cell surface molecules. While SGP is reported to bind to neutrophils via the Fcγ receptor and to inhibit early neutrophil activation, GP is thought to contribute to the tissue tropism of Ebola virus, since a murine retroviral vector pseudotyped with Ebola virus GP more efficiently infected endothelial cells, the major targets of filoviruses, than other cell types tested.

The Ebola virus GP undergoes posttranslational proteolytic cleavage by furin into GP1 and GP2, which are covalently linked by disulfide bonds. SGP and GP1 are phagocytosed by macrophages and other APC's when in secreted form. Those peptides are then presented on MHC class II, which elicits a lytic response by CD4 T cells, a result also observed with GP's of HIV, VSV and influenza virus. Endothelial cells may also be subject to lysis by CD4 T cells when expressing SGP or GP1 in MHC II in addition to destruction by viral replication.

xi. Parainfluenza

Human parainfluenza viruses (HPIVs) are a group of four distinct serotypes of single-stranded RNA viruses belonging to the paramyxovirus family. They are the second most common cause of lower respiratory tract infection in younger children. Repeated infection throughout the life of the host is not uncommon. Symptoms of later breakouts include upper respiratory tract illness as in a cold and sore throat. The incubation period of all four serotypes is 1 to 7 days. Parainfluenza viruses can be detected via cell culture, immunofluorescent microscopy, and PCR.

The four serotypes include: HPIV-1 (most common cause of croup; also other upper and lower respiratory tract illnesses typical), HPIV-2 (causes croup and other upper and lower respiratory tract illnesses), HPIV-3 (associated with bronchiolitis and pneumonia), and HPIV-4 (includes subtypes 4a and 4b).

Paramyxovirus proteins include: nucleocapsid, phosphoprotein, matrix, fusion, attachment proteins, large proteins, and accessory proteins. Nucleocapsid (N) protein associates with genomic RNA (one molecule per hexamer) and protects the RNA from nuclease digestion. The phosphoprotein (P) binds to the N and L proteins and forms part of the RNA polymerase complex. The matrix (M) protein assembles between the envelope and the nucleocapsid core, it organises and maintains virion structure. The fusion (F) protein projects from the envelope surface as a trimer, and mediates cell entry by inducing fusion between the viral envelope and the cell membrane by class I fusion. One of the defining characteristics of members of the paramyxoviridae family is the requirement for a neutral pH for fusogenic activity. The cell attachment proteins span the viral envelope and project from the surface as spikes. They bind to sialic acid on the cell surface and facilitate cell entry. Note that the receptor for measles virus is unknown. Proteins are designated "H" for morbilliviruses and henipaviruses as they possess haemagglutination activity, observed as an ability to cause red blood cells to clump. "HN" attachment proteins occur in respiroviruses and rubulaviruses. These possess both haemagglutination and neuraminidase activity which cleaves sialic acid on the cell surface, preventing viral particles from reattaching to previously infected cells. Attachment proteins with neither haemagglutination nor neuraminidase activity are designated "G" (glycoprotein). These occur in members of pneumovirinae. The large (L) protein is the catalytic subunit of RNA dependent RNA polymerase (RDRP). A mechanism known as RNA editing (see Mononegavirales) allows multiple proteins to be produced from the P gene. These are not essential for replication but can aid in survival in vitro or can be involved in regulating the switch from mRNA synthesis to antigenome synthesis.

The fusion (F) protein precursor of virulent Newcastle disease virus (NDV) strains and human parainfluenza virus type 3 (HPIV3) has a multibasic amino acid sequence at the cleavage site, and intracellular cleavage activation occurs in a variety of cells.

The fusion (F) protein of HPIV3 contains the tribasic cleavage site R-T-K-R (SEQ ID NO: 364). The endogenous endoprotease present in CV-1 cells cleaves F variants containing the furin recognition motif R-X-K/R-R (SEQ ID NO:24) but not mutant variants containing the dibasic site K-R or a single R at the cleavage site. Peptidylchloromethylketone inhibitors mimicking basic cleavage sites prevent cleavage of the precursor F0 by the endogenous protease only when the furin-specific motif is present in the peptidyl portion. Thus, furin is a cellular protease responsible for the activation of the F protein of HPIV3.

xii. Herpes Virus

The Herpesviridae are a large family of DNA viruses that cause diseases in humans and animals. The family name is derived from the Greek herpein ("to creep"), referring to the latent, re-occurring infections typical of this group of viruses. Herpesviridae can cause latent or lytic infections.

There are eight distinct viruses in this family known to cause disease in humans.

HHV-1 (Herpes simplex virus-1 (HSV-1)), HHV-2 (Herpes simplex virus-2 (HSV-2)), HHV-3 (Varicella zoster virus (VZV)), HHV-4 (Epstein-Barr virus (EBV), lymphocryptovirus), HHV-5 (Cytomegalovirus (CMV)), HHV-6, -7 (Roseolovirus), and HHV-8 (Kaposi's sarcoma-associated herpesvirus ((KSHV)).

The human herpesviruses all share some common properties. One shared property is virus structure—all herpesviruses are composed of relatively large double-stranded, linear DNA genomes encoding 100-200 genes encased within an icosahedral protein cage called the capsid which is itself wrapped in a lipid bilayer membrane called the envelope.

HCMV infection requires that a viral envelope glycoprotein(s) and the respective cellular receptor(s) engage in a synchronized series of interactions, ultimately resulting in fusion of the viral envelope with the plasma membrane. Initial attachment of HCMV to permissive host cells is dependent upon the presence of cell surface heparan sulfate proteoglycans (HSPGs). The HCMV glycoprotein complex II (gC-II) was described to be the major HCMV envelope protein complex retained on the heparin matrix, while a lesser proportion of glycoprotein B (gB) (also known as gpUL55) was bound.

HCMV gB is a 906-amino-acid protein encoded by the UL55 open reading frame. The gB precursor is synthesized as a 105-kDa protein, which matures into a 130- to 160-kDa glycoprotein by acquiring N-linked glycosylation modifications in the endoplasmic reticulum and Golgi network. The cellular protease furin cleaves the mature gB into two components, a 93- to 116-kDa amino-terminal fragment and a 55-kDa carboxy-terminal fragment. After stable attachment to the cell surface, a direct pH-independent fusion event occurs between the viral envelope and the plasma membrane. Two HCMV envelope glycoprotein complexes, gB and gH-gL (also known as gpUL75-gpUL115), are crucial components in mediating fusion events required for subsequent virus entry. EBV gB contains a consensus furin cleavage site. The enveloped mature EBV contains both full-length and furin-cleaved gB, similar to herpesviruses.

3. Proprotein Convertases

Proprotein convertases (PCs) are enzymes which convert prohormones into hormones. In some aspects, the proprotein covertase of the disclosed method is a subtilisin-like proprotein convertase. Thus, for example, the proprotein convertase can be Furin (SPC1, PACE, PCSK3), PC2 (SPC2, PCSK2), PC1/3 (SPC3, PC1, PC3, PCSK1), PACE4 (SPC4, PCSK6), PC4, (SPC5, PCSK4), PC5/6 (SPC6, PC5, PC6, PCSK5), or PC7 (SPC7, PC8, LPC, PCSK7).

Furin is a protease of animal cells that is similar in structure to the bacterial protease subtilisin. Furin is enriched in the Golgi apparatus, where it functions to cleave other proteins into their mature/active forms. Furin cleaves proteins just downstream of a basic amino acid target sequence (canonically, Arg-X-(Arg/Lys)-Arg; SEQ ID NO:24). In addition to processing cellular precursor proteins, furin is also utilized by a number of pathogens. For example, the envelope proteins of viruses such as HIV, influenza and dengue fever viruses must be cleaved by furin or furin-like proteases to become fully functional. Anthrax toxin, pseudomonas exotoxin and papillomaviruses must be processed by furin during their initial entry into host cells.

In some aspects, the toxin of the disclosed method can be any toxin that is cleaved by a proprotein convertase. In further aspects, the toxin of the disclosed method can be any toxin that is cleaved by a subtilisin-like endoprotease. In further aspects, the toxin of the disclosed method can be any toxin that is cleaved by furin. Thus, the toxin of the disclosed method can be Influenza A H5N1 hemagglutin type H5 protein, Newcastle disease virus F fusion protein, parainfluenza HPIV3 F protein, Sindbis virus structural polyprotein p130, cytomegalovirus glycoprotein B (gpUL55), HIV-1 glycoprotein-160, Measles virus fusion protein, infectious bronchitis spike protein, Marburg virus spike glycoprotein, Ebola envelope glycoprotein, Epstein-Barr virus glycoprotein gp100, *Pseudomonas aeruginosa* exotoxin A, Anthrax protective antigen, Botulinum toxin, Clostridium alpha-toxin, Diphtheria toxin, *Aeromonas aerolysin*, and *Shigella shiga* toxin, Borna disease p57/gp94, flaviviral prM protein, Mumps virus F glycoprotein, Varicella zoster gpII, Bovine leukemia gp72, Rous sarcoma env protein, and respiratory syncytial F protein.

In some aspects, the pathogen can be any pathogen that produces a toxin cleaved by a proprotein convertase. In some aspects, the pathogen can be any pathogen that produces a toxin cleaved by a subtilisin-like endoprotease. Thus, the pathogen can be any pathogen that produces a toxin cleaved by furin (SPC1, PACE, PCSK3). The pathogen can be any pathogen that produces a toxin cleaved by PC2 (SPC2, PCSK2). The pathogen can be any pathogen that produces a toxin cleaved by PC1/3 (SPC3, PC1, PC3, PCSK1). The pathogen can be any pathogen that produces a toxin cleaved by PACE4 (SPC4, PCSK6). The pathogen can be any pathogen that produces a toxin cleaved by PC4 (SPC5, PCSK4). The pathogen can be any pathogen that produces a toxin cleaved by PC5/6 (SPC6, PC5, PC6, PCSK5). The pathogen can be any pathogen that produces a toxin cleaved by PC7 (SPC7, PC8, LPC, PCSK7).

Thus, the pathogen can be from a bacteria selected from the group consisting of *Bacillus, Pseudomonas, Clostridium, Corynebacterium, Aeromonas*, and *Shigella*. Thus, the pathogen can be from a bacteria selected from the group consisting of *Bacillus anthracis, Pseudomonas aeruginosa, Corynebacterium diphtheriae, Aeromonas aerolysin*, and *Shigella shigae*.

Thus, the pathogen can be from a virus selected from the group consisting of Influenzavirus A, parainfluenza, Sindbis virus, Newcastle disease virus, flavivirus (including Dengue hemorrhagic fever 1, 2, 3 and 4, Yellow fever, Usutu, West Nile, Kunjin, Murray, Japanese encephalitis, St. Loius encephalitis and related), cytomegalovirus, herpesvirus, HIV, Measles virus, infectious bronchitis virus, Coronavirus, Marburg virus, Ebola virus, Epstein-Barr virus, Borna disease virus, Mumps virus, Varicella zoster virus, Bovine leukemia virus, Rous sarcoma virus, and respiratory syncytial virus.

4. Internalization Sequence

The disclosed proprotein convertase inhibitors can comprise a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 1).

TABLE 1

Cell Internalization Transporters

| 5. Name | 6. Sequence | 7. SEQ ID NO |
| --- | --- | --- |
| Antp | RQPKIWFPNRRKPWKK | (SEQ ID NO: 347) |
| HIV-Tat | GRKKRRQRPPQ | (SEQ ID NO: 348) |
| Penetratin | RQIKIWFQNRRMKWKK | (SEQ ID NO: 349) |
| Antp-3A | RQIAIWFQNRRMKWAA | (SEQ ID NO: 350) |
| Tat | RKKRRQRRR | (SEQ ID NO: 351) |
| Buforin II | TRSSRAGLQFPVGRVHRLLRK | (SEQ ID NO: 352) |
| Transportan | GWTLNSAGYLLGKINKALAALAKKIL | (SEQ ID NO: 353) |
| model amphipathic peptide (MAP) | KLALKLALKALKAALKLA | (SEQ ID NO: 354) |
| K-FGF | AAVALLPAVLLALLAP | (SEQ ID NO: 355) |
| Ku70 | VPMLK-PMLKE | (SEQ ID NO: 356) |
| Prion | MANLGYWLLALFVTMWTDVGLCKKRPKP | (SEQ ID NO: 357) |
| pVEC | LLILRRRIRKQAHAHSK | (SEQ ID NO: 358) |
| Pep-1 | KETWWETWWTEWSQPKKKRKV | (SEQ ID NO: 359) |
| SynB1 | RGGRLSYSRRRFSTSTGR | (SEQ ID NO: 360) |
| Pep-7 | SDLWEMMMVSLACQY | (SEQ ID NO: 361) |
| HN-1 | TSPLNIHNGQKL | (SEQ ID NO: 362) |
| BGSC (Bis-Guanidinium-Spermidine-Cholesterol) | | |

BGSC

TABLE 1-continued

Cell Internalization Transporters

| 5. Name | 6. Sequence | 7. SEQ ID NO |
|---|---|---|
| BGSC (Bis-Guanidinium-Tren-Cholesterol) | 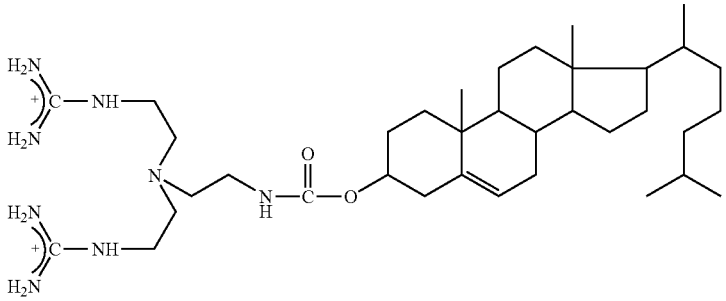 BGTC | |

Thus, the disclosed proprotein convertase inhibitor can further comprise the amino acid sequence SEQ ID NO:347, SEQ ID NO:348 (Bucci, M. et al. 2000. Nat. Med. 6, 1362-1367), SEQ ID NO:349 (Derossi, D., et al. 1994. Biol. Chem. 269, 10444-10450), SEQ ID NO:350 (Fischer, P. M. et al. 2000. J. Pept. Res. 55, 163-172), SEQ ID NO:351 (Frankel, A. D. & Pabo, C. 0.1988. Cell 55, 1189-1193; Green, M. & Loewenstein, P. M. 1988. Cell 55, 1179-1188), SEQ ID NO:352 (Park, C. B., et al. 2000. Proc. Natl. Acad. Sci. USA 97, 8245-8250), SEQ ID NO:353 (Pooga, M., et al. 1998. FASEB J. 12, 67-77), SEQ ID NO:354 (Oehlke, J. et al. 1998. Biochim. Biophys. Acta. 1414, 127-139), SEQ ID NO:355 (Lin, Y. Z., et al. 1995. J. Biol. Chem. 270, 14255-14258), SEQ ID NO:356 (Sawada, M., et al. 2003. Nature Cell Biol. 5, 352-357), SEQ ID NO:357 (Lundberg, P. et al. 2002. Biochem. Biophys. Res. Commun. 299, 85-90), SEQ ID NO:358 (Elmquist, A., et al. 2001. Exp. Cell Res. 269, 237-244), SEQ ID NO:359 (Morris, M. C., et al. 2001. Nature Biotechnol. 19, 1173-1176), SEQ ID NO:360 (Rousselle, C. et al. 2000. Mol. Pharmacol. 57, 679-686), SEQ ID NO:361 (Gao, C. et al. 2002. Bioorg. Med. Chem. 10, 4057-4065), or SEQ ID NO:362 (Hong, F. D. & Clayman, G. L. 2000. Cancer Res. 60, 6551-6556). The provided polypeptide can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety for the teachings of cellular internalization vectors and sequences. Any other internalization sequences now known or later identified can be combined with a polypeptide disclosed herein.

8. Carriers

The disclosed proprotein convertase inhibitors can be combined, conjugated or coupled with or to carriers and other compositions to aid administration, delivery or other aspects of the inhibitors and their use. For convenience, such composition will be referred to herein as carriers. Carriers can, for example, be a small molecule, pharmaceutical drug, fatty acid, detectable marker, conjugating tag, nanoparticle, or enzyme.

The carrier can be any substance that can be used with the disclosed inhibitors, and is not restricted by size or substance. Examples include, but are not limited to, nanoparticles (such as silica nanoparticles, iron oxide nanoparticles or albumin nanoparticles), liposomes, small organic molecules, microparticles, or microbubbles, such as fluorocarbon microbubbles. The term carrier is used to identify a component of the disclosed conjugate but is not intended to be limiting. In particular, the disclosed carriers are not limited to substances, compounds, compositions, particles or other materials composed of a single molecule. Rather, the disclosed carriers are any substance(s), compound(s), composition(s), particle(s) and/or other material(s) that can be conjugated with one or more PC inhibitors. A variety of examples of suitable carriers are described and disclosed herein.

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds can be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)). The carrier molecule can be covalently linked to the disclosed inhibitors. The carrier molecule can be linked to the amino terminal end of the disclosed peptides. The carrier molecule can be linked to the carboxy terminal end of the disclosed peptides. The carrier molecule can be linked to an amino acid within the disclosed peptides. The herein provided compositions can further comprise a linker connecting the carrier molecule and disclosed inhibitors. The disclosed inhibitors can also be conjugated to a coating molecule such as bovine serum albumin (BSA) (see Tkachenko et al., (2003) J Am Chem Soc, 125, 4700-4701) that can be used to coat microparticles, nanoparticles of nanoshells with the inhibitors.

Protein crosslinkers that can be used to crosslink the carrier molecule to the inhibitors, such as the disclosed peptides, are known in the art and are defined based on utility and structure and include DSS (Disuccinimidylsuberate), DSP (Dithiobis (succinimidylpropionate)), DTSSP (3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimidyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SLAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP(N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

Given that cell surface-associated PCs in bronchial epithelial cells are the first to encounter inhaled pathogens, it was realized that for of the disclosed inhibitor compositions suitable for inhalation was desirable. Attaching PC inhibitors to nanoparticles are one useful form of such compositions.

i. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohoms, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, silica nanoparticles, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

For example, PC inhibitors such as the disclosed peptides can be immobilized on silica nanoparticles (SNPs). SNPs have been widely used for biosensing and catalytic applications owing to their favorable surface area-to-volume ratio, straightforward manufacture and the possibility of attaching fluorescent labels, magnetic nanoparticles (Yang, H. H. et al. 2005) and semiconducting nanocrystals (Lin, Y. W., et al. 2006). When peptides with a GGG linker (FIG. 1A) were immobilized on 15-nm diameter 4-formylbenzoyl chloride-activated SNPs with a density of ~100 peptide molecules/SNP, it was found that the inhibitory efficacy (on a molar basis) of the immobilized peptides against furin was similar to that of the soluble peptides (FIGS. 2B and C). Furthermore, SNPs showed no cell toxicity, even at high concentrations [e.g., 50 nM SNPs ($3\times10^{17}$ SNP particles)/100,000 cells].

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Targeting molecules can be attached to the disclosed compositions and/or carriers. For example, the targeting molecules can be antibodies or fragments thereof, ligands for specific receptors, or other proteins specifically binding to the surface of the cells to be targeted.

ii. Liposomes

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J. Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. 1, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 µm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. 1, II & III (1984). This and the aforementioned references describing various lipid vesicles suitable for use in the invention are incorporated herein by reference.

Fatty acids (i.e., lipids) that can be conjugated to the provided compositions include those that allow the efficient incorporation of the proprotein convertase inhibitors into liposomes. Generally, the fatty acid is a polar lipid. Thus, the fatty acid can be a phospholipid The provided compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, pahnitelaidoyloleoylphosphatidylcholine, palmitelaidoyloleoylphosphatidylserine, palmitelaidoyloleoylphosphatidylethanolamine, palmitelaidoyloleoylphosphatidylglycerol, pahnitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

9. Nucleic Acids

Also provided is an isolated nucleic acid encoding any one or more of the disclosed peptides. Thus, for example, provided is an isolated nucleic acid encoding one or more peptides comprising the amino acid sequence SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, SEQ ID NO:223, SEQ ID NO:365, SEQ ID NO:366, SEQ ID NO:367, SEQ ID NO:368, SEQ ID NO:369, SEQ ID NO:370, or a combination thereof.

The disclosed nucleic acids can be made up of, for example, nucleotides, nucleotide analogs, or nucleotide substitutes. Non-limiting examples of these and other molecules are discussed herein. It is understood that, for example, when a vector is expressed in a cell, the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

10. Nucleic Acid Delivery Systems

Also provided herein are vectors comprising nucleic acids that encode the disclosed peptides. These vectors can be used to recombinantly express the peptides either in vitro or in vivo. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids into the cell without degradation and include a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

11. Expression Systems

Nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

i. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

ii. Markers

The disclosed vectors can include nucleic acid sequence encoding a marker product. This marker product is used to determine if the nucleic acid has been delivered to the cell and once delivered is being expressed. Preferred marker genes are the *E. Coli* lacZ gene, which encodes 3-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

B. Methods

Disclosed are methods using inhibitors of proprotein convertases such as furin. The disclosed inhibitors can be administered to subjects that have been exposed to, are suspected of being exposed to, may become exposed to or are infected by a pathogen or other harmful organism. The disclosed method is useful where the pathogen requires or makes use of host proprotein convertases. Inhibition of one or more proprotein convertases can, for example, prevent, reduce, interfere with, slow or otherwise affect the pathogen, the effect of the pathogen, the infectivity of the pathogen, the ability of the pathogen to produce or sustain an infection, one or more harmful effects of the pathogen, or a combination. For example, provided is a method of treating a subject with a pathogen infection, comprising administering to the subject a therapeutically effective amount of a proprotein convertase inhibitor. Also provided is a method of reducing risk of harm from a pathogen infection in a subject, comprising administering to the subject a therapeutically effective amount of a proprotein convertase inhibitor. Useful proprotein convertases can be non-toxic. Thus, for example, the furin inhibitor is Dec-RVKR-CMK can be excluded as a proprotein convertase inhibitor.

The type and extent of harm associated with a pathogen infection is dependent on the selected pathogen. However, for the pathogens disclosed herein, the harm is at least partially dependent on the enzymatic processing of pathogenic proteins by proprotein convertase enzymes. Thus, the skilled artisan will be able to ascertain the ability of the disclosed compositions and methods to reduce harm in a given pathogen based on an understanding in the art of the role of enzymatic processing for that pathogen.

Thus, the pathogen can in some aspects be any pathogen that produces a toxin cleaved by a proprotein convertase. Thus, the method can further comprise identifying a subject suspected of being exposed to or at risk of being exposed to a pathogen that produces toxins cleaved by a proprotein convertase.

A proprotein convertase inhibitor, as used herein, is any compound or composition that can inhibit the ability of one or more proprotein convertases to cleave one or more of their substrates. For example, a proprotein convertase inhibitor can in some aspects inhibit the ability of furin to cleave a peptide comprising the amino acid sequence SEQ ID NO:24. Proprotein convertase inhibitors can also be referred to as inhibitors of any or all of the respective proprotein convertase against which the inhibitor is effective. Thus, for example, a proprotein convertase inhibitor that can inhibit furin can be referred to as a furin inhibitor. This is the case regardless of whether the inhibitor inhibits only firinor can also inhibit other proprotein convertases.

In some aspects of the disclosed method, the proprotein convertase inhibitor can inhibit the activity of a plurality of proprotein convertases. For example, the proprotein convertase inhibitor can inhibit the activity of 2, 3, 4, 5, 6, 7, 8, 9, 10 or more proprotein convertases.

The proprotein convertase inhibitor of the disclosed method can comprise a peptide as disclosed herein. In some aspects, the proprotein convertase inhibitor can be a peptide comprising a furin cleavage motif, wherein the peptide is resistant to furin proteolysis. Thus, in some aspects, the peptide can comprise the amino acid sequence R-X-R/K-R (SEQ ID NO:24). In further aspects, the peptide can comprise the amino acid sequence $X_1RX_2RRRKKRX_3$, wherein $X_1$ is TP or TPQ, wherein $X_2$ is A or G, and $X_3$ is any or no amino acid (SEQ ID NOs:346, 371, 372 and 373).

Thus, the proprotein convertase inhibitor of the disclosed method can comprise a peptide comprising an amino acid sequence selected from the group consisting of SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, SEQ ID NO:223, SEQ ID NO:365, SEQ ID NO:366, SEQ ID NO:367, SEQ ID NO:368, SEQ ID NO:369, or SEQ ID NO:370.

The proprotein convertase inhibitor of the disclosed method can comprise a peptide consisting essentially of an amino acid sequence selected from the group consisting of SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, SEQ ID NO:223, SEQ ID NO:365, SEQ ID NO:366, SEQ ID NO:367, SEQ ID NO:368, SEQ ID NO:369, or SEQ ID NO:370

1. Administration

The disclosed compounds and compositions can be administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like. For example, the proprotein convertase inhibitor can be administered to the skin or mucosa of the subject. Additional methods include aerosol, with or without carrier particles such as nanoparticles, and sustained release methods.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of a peptide disclosed herein used alone might range from about 1 µg/kg to up to 100 mg/kg of body weight or more per day, depending on the factors mentioned above. Thus, the a typical daily dosage of a peptide disclosed herein can be from about 1, 2, 3, 4, 5, 6, 7, 8, 9, 10, 15, 20 mg/kg.

Following administration of a disclosed composition for treating, inhibiting, or preventing pathogen harm, the efficacy of the therapeutic can be assessed in various ways well known to the skilled practitioner.

The disclosed compositions that inhibit proprotein convertases may be administered prophylactically to patients or subjects who are at risk for exposure to a pathogen or who have been newly exposed to a viral or bacterial pathogen.

The disclosed compositions and methods can also be used for example as tools to isolate and test new drug candidates for a variety of pathogen related diseases.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue, the principles of which can be applied to targeting of other cells (Senter, et al., Bioconjugate Chem., 2:447-451, (1991); Bagshawe, K. D., Br. J. Cancer, 60:275-281, (1989); Bagshawe, et al., Br. J. Cancer, 58:700-

703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

2. Identifying Peptides

Also provided is a method of identifying a peptide that can inhibit the activity of a proprotein convertase, comprising determining the amino acid sequence of a natural cleavage site in a pathogenic toxin cleaved by a proprotein convertase; producing a peptide, wherein at least 7, 8, 9, 10, 11, 12, 13, 14, 15, 16, 17, 18, 19, 20 amino acid residues have at least 70%, 75%, 80%, 85%, 90%, 95%, 96%, 97%, 98%, or 99% sequence identity to the natural cleavage site; and assaying the peptide for the ability to inhibit the activity of one or more proprotein convertases.

The ability of a peptide to inhibit the activity of a proprotein convertase can be assayed using any method known in the art. For example, a candidate peptide can added to a sample comprising a proprotein convertase and a detection peptide comprising a cleavage motif for said proprotein convertase. The method can then further comprise assaying for the presence of cleavage of the detection peptide. For example, the method can comprise detecting peptide fragments of the detection peptide. The amount of cleavage of the detection peptide can be compared to negative control and/or a reference standard in order to characterize the amount of inhibition. In some aspects, the detection peptide comprises a detectable marker, such as a fluophore. Thus, the detection peptide can be a fluorogenic substrate or a chromogenic substrate.

The toxin for use in the disclosed method can be, for example, selected from the group consisting of Influenza A H5N1 hemagglutin type H5 protein, Newcastle disease virus F fusion protein, parainfluenza HPIV3 F protein, Sindbis virus structural polyprotein p130, cytomegalovirus glycoprotein B (gpUL55), HIV-1 glycoprotein-160, Measles virus fusion protein, infectious bronchitis spike protein, Marburg virus spike glycoprotein, Ebola envelope glycoprotein, Epstein-Barr virus glycoprotein gp100, *Pseudomonas aeruginosa* exotoxin A, Anthrax protective antigen, Botulinum toxin, Clostridium alpha-toxin, Diphtheria toxin, Aeromonas aerolysin, and *Shigella* shiga toxin, Borna disease p57/gp94, flaviviral prM protein, Mumps virus F glycoprotein, Varicella zoster gpII, Bovine leukemia gp72, Rous sarcoma env protein, and respiratory syncytial F protein.

The proprotein convertase assessed in the disclosed method can be, for example, Furin (SPC1, PACE, PCSK3), PC2 (SPC2, PCSK2), PC1/3 (SPC3, PC1, PC3, PCSK1), PACE4 (SPC4, PCSK6), PC4, (SPC5, PCSK4), PC5/6 (SPC6, PC5, PC6, PCSK5), or PC7 (SPC7, PC8, LPC, PCSK7).

The peptide of the disclosed method can inhibit the activity of a plurality of proprotein convertases. For example, the disclosed peptide can inhibit the activity of 2, 3, 4, 5, 6, 7, 8, 9, 10 or more proprotein convertases.

3. Making the Compositions

The compositions disclosed herein and the compositions necessary to perform the disclosed methods can be made using any method known to those of skill in the art for that particular reagent or compound unless otherwise specifically noted.

i. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

C. Uses

The disclosed compositions can be used in a variety of ways as research tools. For example, the disclosed compositions, such an isolated polypeptide comprising SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, SEQ ID NO:223, SEQ ID NO:365, SEQ ID NO:366, SEQ ID NO:367, SEQ ID NO:368, SEQ ID NO:369, or SEQ ID NO:370 can be used to study the interactions between proprotein convertase enzymes and their pathogen substrates, by for example acting as inhibitors of binding. Other uses are disclosed, apparent from the disclosure, and/or will be understood by those in the art.

D. kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for XXX, the kit comprising XXX. The kits also can contain XXX. The disclosed kits can also include XXX.

E. Uses

The disclosed compositions can be used in a variety of ways as research tools. For example, the disclosed compositions, such an isolated polypeptide comprising SEQ ID NOs: XXX can be used to study the interactions between XXX and XXX, by for example acting as inhibitors of binding. Other uses are disclosed, apparent from the disclosure, and/or will be understood by those in the art. Other uses include XXX. Other uses are disclosed, apparent from the disclosure, and/or will be understood by those in the art.

F. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

As used herein, the term "subject" means any target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "therapeutically effective" means that the amount of the composition used is of sufficient quantity to ameliorate one or more causes or symptoms of a disease or disorder. Such amelioration only requires a reduction or alteration, not necessarily elimination.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Targeting Host Proteinases as a Therapeutic Strategy Against Viral and Bacterial Pathogens i. Results Furin and related PCs are subtilisin-like endoproteases which cleave the multibasic motifs R-X-R/K-R (SEQ ID NO:24) and transform proproteins into biologically active proteins and peptides. PCs are implicated in many pathogenic states because they also process membrane fusion proteins and pro-toxins of a wide variety of pathogenic bacteria and viruses, including highly pathogenic H5N1 avian influenza. The pathogenicity of H5N1 correlates with the extended furin cleavage motif, TPQRERRRKKR↓GL (SEQ ID NO:224), within the H5 sequence (Subbarao, K. et al. 1998; Chen, J. et al. 1998; Basak, A., et al. 2001). Following furin cleavage, the resulting protein becomes competent to initiate fusion with the host membrane.

Disclosed herein is the use of the furin cleavage sequence of H5 as the starting point to obtain peptide sequences that inhibit cleavage of a fluorescent peptide substrate by furin (Fugere, M. et al. 2002). The presence of the Gln residue at position P9 of the TPQRERRRKKRG (SEQ ID NO:174) cleavage motif was not necessary for inhibition. Using alanine scanning mutagenesis a potent inhibitor was found (TPRARRRKKRG (SEQ ID NO:28), Ki=57 nM; FIG. 1A and Table 2), which was improved further by substitution of the C-terminal glycine by threonine (TPRARRRKKRT (SEQ ID NO:212), Ki=23 nM; FIG. 1A and Table 3). Other PCs (PACE4, PC4, PC5/6 and PC7) were also inhibited but with less efficiency. Peptides with aromatic C-terminal residues (F or Y) were more selective for furin, while TPQRARRRKKRT (SEQ ID NO:151) and TPRARRRKKRT (SEQ ID NO:212) were potent pan-inhibitors of PCs (Ki=150-300 nM) (FIG. 1B). Co-incubation of the peptides with furin followed by mass-spectrometry analysis showed that the inhibitory peptides were resistant to furin proteolysis.

It was next determined if the H5-derived peptides could inhibit intoxication by two unrelated pathogens, anthrax and *Pseudomonas* toxins. Host cleavage of anthrax Protective Antigen-83 (PA83) is a prerequisite for the translocation of the toxic enzymes, Lethal Factor (LF) and Edema Factor, into the host cell cytosol (Collier, R. J. & Young, J. A. 2003). It was determined that PA83 was cleaved by furin and also by PC4 and PC5/6 while PACE4 and PC7 were less effective. Furin and PC5/6 also efficiently cleaved the recombinant H5 precursor (HA0; Stevens, J. et al. 2004), while other PCs were less efficient (FIG. 1C).

Figure 1D:
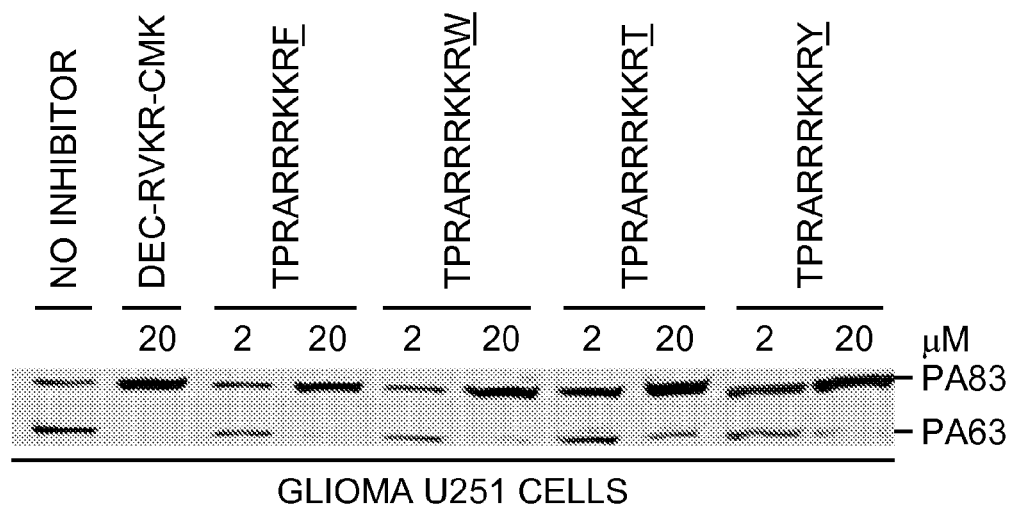
FIG. 1D shows inhibition of the processing of biotin-labeled anthrax protective antigen 83 (PA83; 1 µg/ml) by the peptides in glioma U251 cells.
Figure 1E:
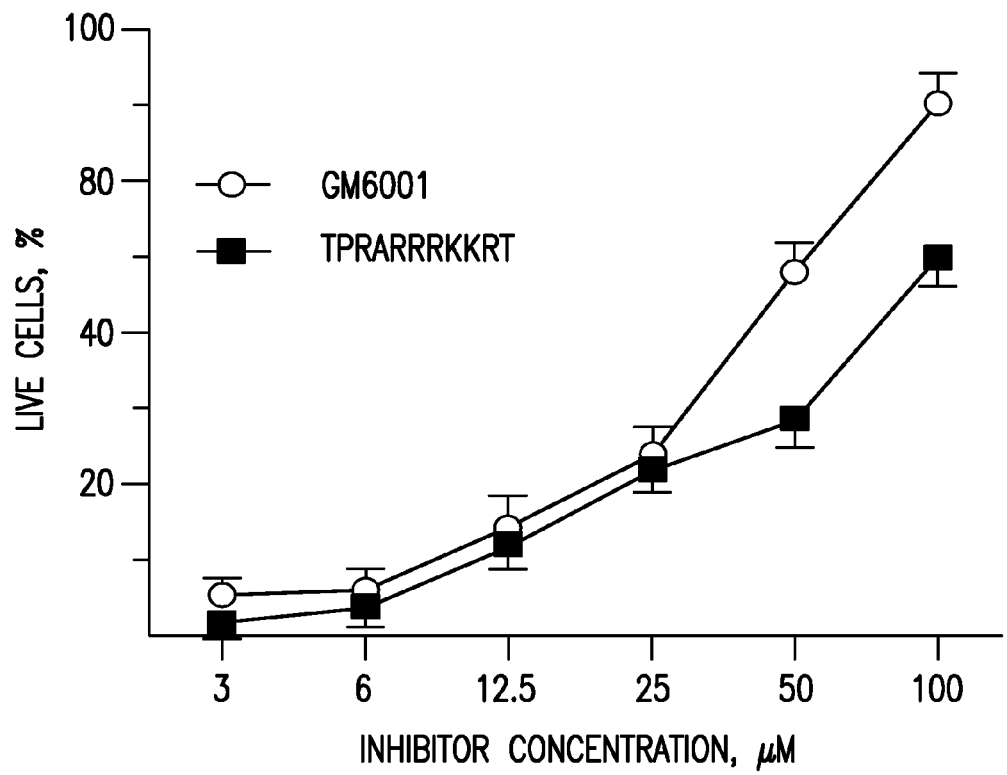
FIG. 1E shows inhibitors protect murine macrophage RAW264.7 cells against LF. Cells were co-incubated with PA83 (400 ng/ml) and LF (25 ng/ml). Indicated concentrations of the inhibitors were added to the cells. The residual viable cells were measured by adding the tetrazolium salt 3-[4,5-dimethylthiazol-2-yl]-2,5-diphenyltetrazolium bromide (MTT). To protect the peptide from proteolysis in vivo, the TPRARRRKKRT (SEQ ID NO:212) peptide sequence was amidated at the C-terminus and had β-Ala at the N-terminus.

Using a cell-based assay (glioma U251 cells; Remacle, A. G., et al. 2006), it was determined that TPRARRRKKRX peptides with C-terminal F, W, T and Y (SEQ ID NO:225) were potent inhibitors of PA83 processing (FIG. 1D). Furthermore, the TPRARRRKKRT (SEQ ID NO:212) peptide inhibited delivery of the PA63-LF complex into the cytosol and protected cells from LF-induced cytotoxicity (FIG. 1E) with an efficiency similar to that of GM6001 (a hydroxamate inhibitor of LF; Forino, M. et al. 2005). The peptide alone at concentrations $\leq$0.5 mM displayed no toxicity and had no effect on cell viability.

Figure 1F:
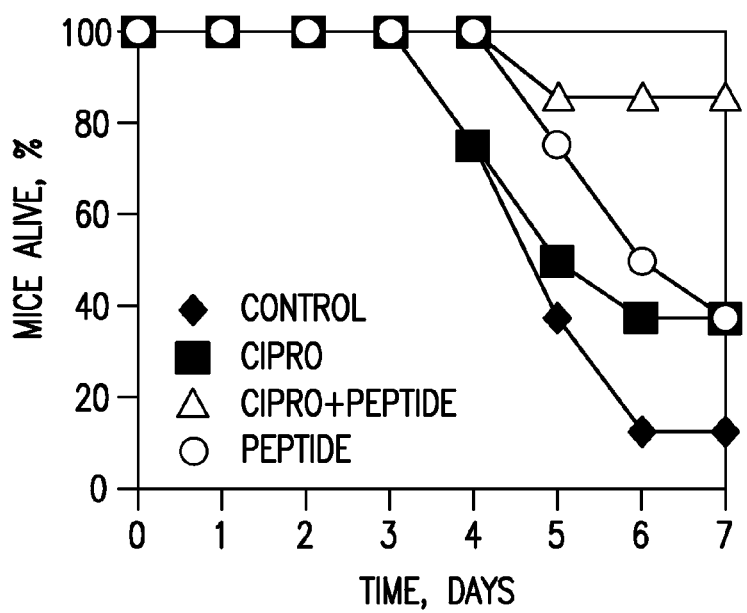
FIG. 1F shows the β-Ala-TPRARRRKKRT-amide peptide (SEQ ID NO:212) and Cipro protect A/J mice from anthrax. Mice (8 animals/group) were infected intranasally with $4 \times 10^5$ B. anthracis Sterne spores. Treatment with the peptide (12.5 mg/kg i.p.) was started 24 h postexposure and continued for the next 6 days. On the fourth day following infection, mice were given daily injections of Cipro (25 mg/kg subq). Non-treated mice were used as a control. e=D-Glu; k=D-Lys; 1=β-Ala; 2=ε-aminohexanoic acid; 3=aminocyclopentanecarboxylic acid; 4=Citrullin; 5=Cys(Me); 6=Nle.

The peptide was next tested in a mouse model of inhalation anthrax (Collier, R. J. & Young, J. A. 2003; Forino, M. et al. 2005). A/J mice (8 mice/group) received *B. anthracis* Sterne spores ($4 \times 10^5$/animal). On the day following infection, mice received the TPRARRRKKRT (SEQ ID NO:212) peptide (12.5 mg/kg i.p.) and then continued to receive injections once daily for the remainder of the experiment. Mice treated with Cipro received 25 mg/kg subcutaneously daily beginning on the fourth day following infection. This post-exposure peptide/Cipro regimen protected 90% of the infected mice from disease, compared with 40% using either the peptide or Cipro alone (FIG. 1F).

Figure 3A:
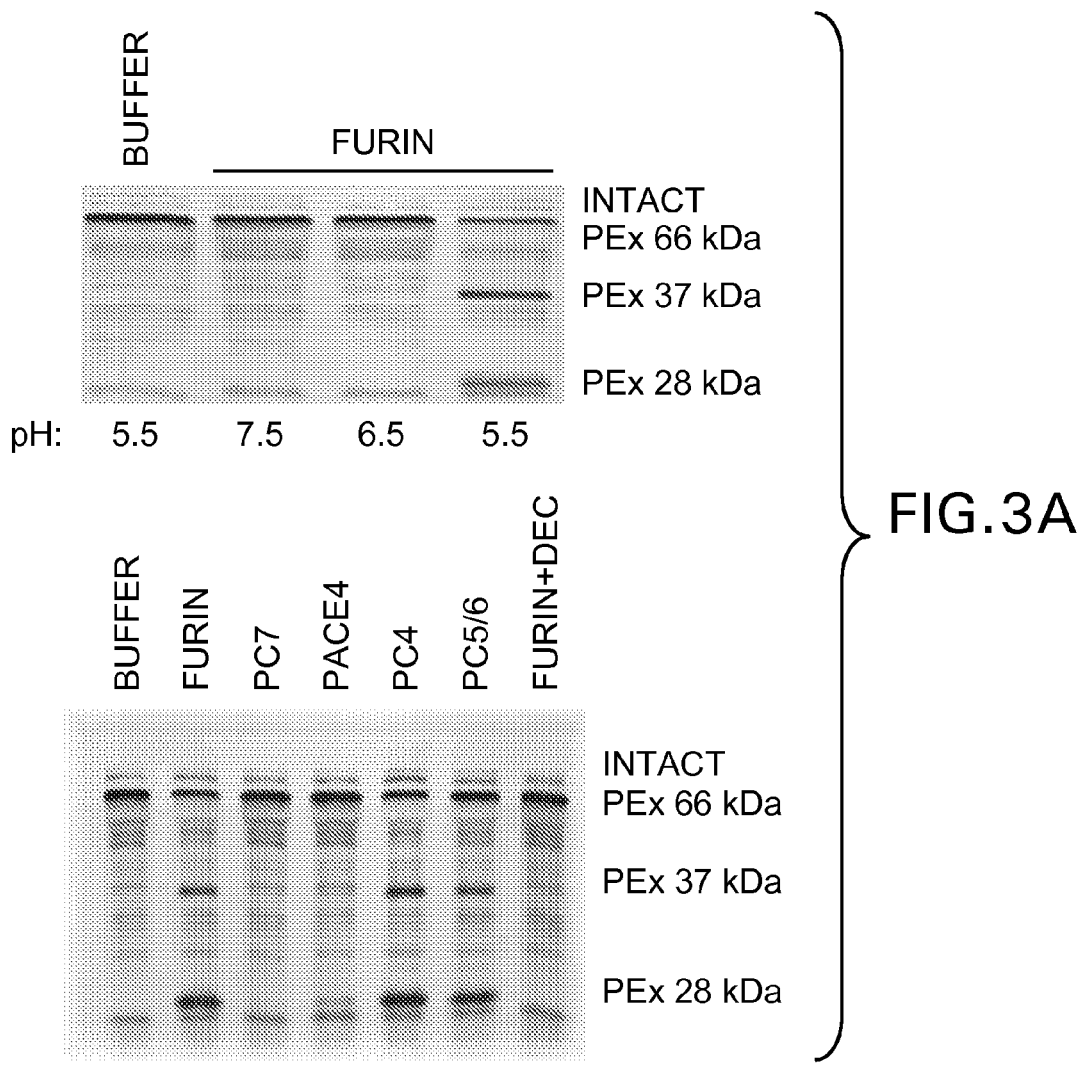
FIG. 3A left panel shows furin cleaves the exposed cleavage site of PEx at pH 5.5 to produce the 28 kDa N-terminal and the 37 kDa C-terminal fragments.
Figure 3B:
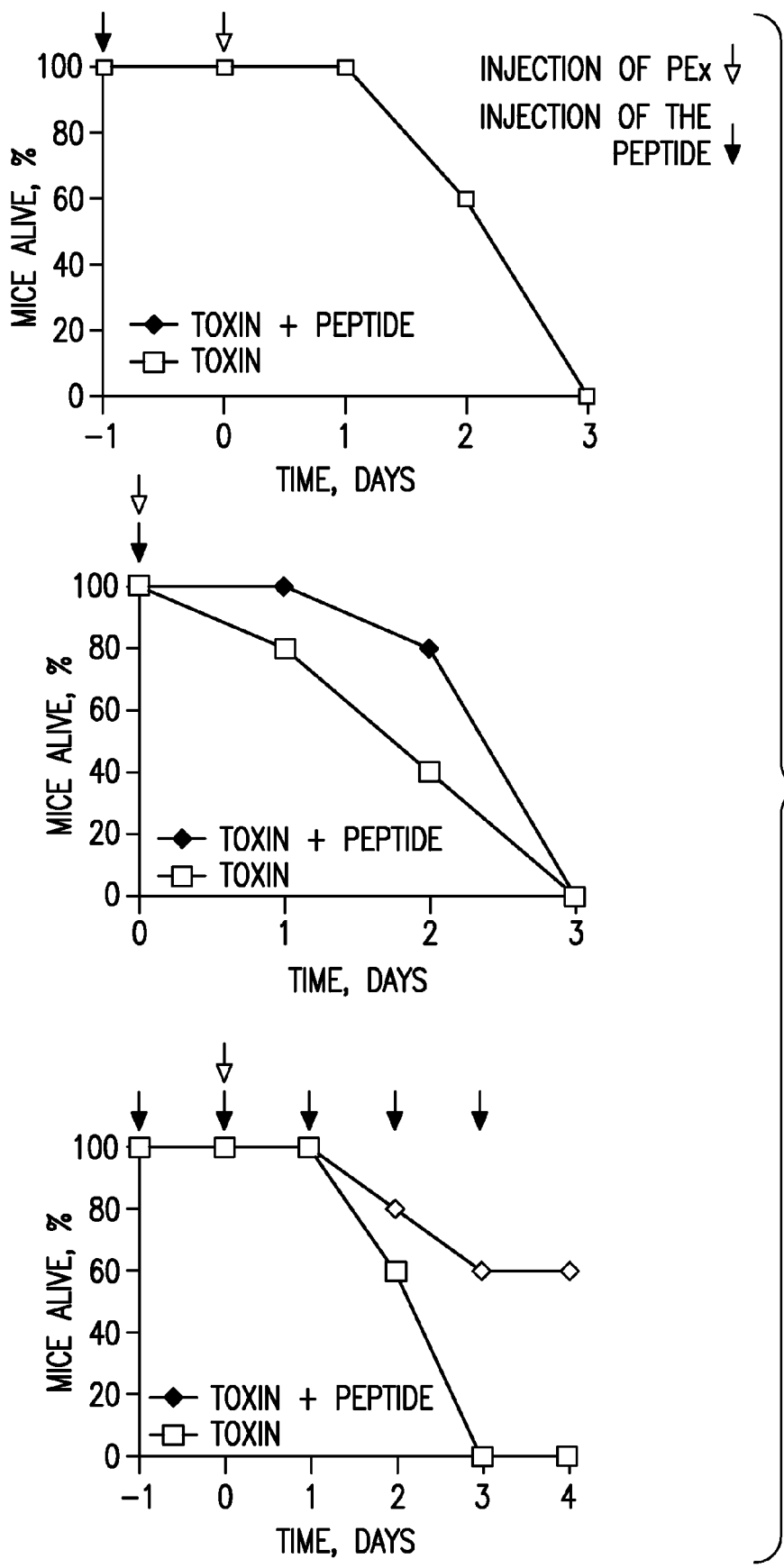
FIG. 3B shows animal experiments with PEx and the TPRARRRKKRT peptide (SEQ ID NO:212).

A similar set of experiments was carried out with an unrelated toxin, *Pseudomonas* exotoxin A. Consistent with the earlier data (Chiron, M. F., et al. 1997), *Pseudomonas* exotoxin A (PEx) was resistant to PC cleavage at pH 7.5 but following unfolding at pH 5.5 PEx (66 kDa) was readily processed by furin, PC4 and PC5/6 to produce the 28 kDa N-terminal fragment and the toxic 37 kDa Cterminal fragment (FIG. 3A). C57/BL6 mice (5 mice/group) received one intramuscular injection of PEx (500 ng/animal; 2xLD$_{50}$; Fogle, M. R., et al. 2002) and one injection of the TPRARRRKKRT (SEQ ID NO:212) peptide (12.5 mg/kg i.p.) either 24 h prior to toxin injection or simultaneously with toxin. Another group of mice, after receiving one injection of the peptide 24 h prior to toxin injection, continued to receive daily injections of the peptide for the remainder of the experiment. Daily injections of the peptide provided good protection (60% survival) from the lethal action of PEx, demonstrating efficacy against a second, otherwise unrelated, furin-dependent pathogen (FIG. 3B).

Given that cell surface-associated PCs in bronchial epithelial cells are the first to encounter inhaled pathogens, the development of an inhalation drug that could be used for acute treatment or for prophylactic use in civilian or battlefield settings was propose. Peptide immobilization was investigated on silica nanoparticles (SNPs), which have been widely used for biosensing and catalytic applications owing to their favorable surface area-to-volume ratio, straightforward manufacture and the possibility of attaching fluorescent labels, magnetic nanoparticles (Yang, H. H. et al. 2005) and semiconducting nanocrystals (Lin, Y. W., et al. 2006). When peptides with a GGG linker (FIG. 1A) were immobilized on 15-nm diameter 4-formylbenzoyl chloride-activated SNPs with a density of ~100 peptide molecules/SNP, it was found that the inhibitory efficacy (on a molar basis) of the immobilized peptides against furin was similar to that of the soluble peptides (FIGS. 2B and C). Furthermore, SNPs showed no cell toxicity, even at high concentrations [e.g., 50 nM SNPs ($3\times10^{17}$ SNP particles)/100,000 cells].

In summary, peptides based on the cleavage motif of H5 are efficient inhibitors of furin and related PCs, and these inhibitors prevent the cleavage and activation of different and unrelated viral pathogens. The results provide examples of and a foundation for the development of novel drugs to be used both as therapeutics and prophylactics against a broad range of natural and engineered infectious agents (Fugere, M. & Day, R. 2005; Scamuffa, N., et al. 2006), including bird flu, anthrax, Marburg, Ebola and flaviviral infections and multiple additional furin-dependent acute disease pathogens.

ii. Materials and Methods

Reagents: Reagents were purchased from Sigma (St Louis, Mo.) unless indicated otherwise. A TMB/M substrate and GM6001 were from Chemicon (Temecula, Calif.). The furin inhibitor decanoyl-Arg-Val-Lys-Arg-chloromethylketone (DEC-RVKR-CMK) was obtained from Bachem Bioscience (King of Prussia, Pa.). The protease inhibitor cocktail set III, and the fluorescence peptide substrate pyroglutamic acid-Arg-Thr-Lys-Arg-methyl-coumaryl-7-amide (Pyr-RTKR-AMC; SEQ ID NO: 273) were obtained from Calbiochem (San Diego, Calif.). Sulfosuccinimidyl-6-(biotinamido) hexanoate [EZ-Link sulfo-NHS-Long Chain(LC)-biotin] was from Pierce (Rockford, Ill.). Anthrax PA83 and *Pseudomonas* exotoxin A (PEx) were purchased from List Biological Laboratories (Campbell, Calif.). Recombinant human furin, PC5/6, PC4 and PC7, and rat PACE4 were prepared in the S2 *Drosophila* expression system (Invitrogen, Carlsbad, Calif., USA) and purified to homogeneity as described earlier (Fugere, M. et al. 2002).

Expression and purification of H5: The ectodomain of H5 was cloned into the baculovirus pAcGP67A transfer vector (BD Biosciences, Bedford, Mass.) to allow for efficient secretion of the recombinant protein. To facilitate the yield of the stable H5 precursor, the C-terminal region of the contract contained the bacteriophage T4 fibritin "foldon" trimerizing sequence, a thrombin cleavage site and a Hisx6 tag (RSLVPRGSPGSGYIPEAPRDGQAYVRKDGEWVLLSTFLGHHHHHH (SEQ ID NO:93 the thrombin site, the T4 foldon and His-tag sequences are italicized, underlined and shown in bold, respectively). Infection of Sf9 insect cells with the recombinant plasmid and virus amplification was performed according to the manufacturer's instructions (Pharmingen, San Diego, Calif.). Infected cells ($3\times10^6$ cells/ml infected at a multiplicity of infection equal to 1-3) were cultured in suspension for 3 days in 4 liters of sf900-II SFM serum-free medium (Invitrogen, Carlsbad, Calif.). Cells were then removed by centrifugation. The soluble H5 was purified from the supernatant by metal affinity chromatography on an Ni-NTA column followed by the Mono-Q FPLC and size-exclusion chromatography on a Superdex-200 10/30 column equilibrated with 10 mM Tris-HCl buffer, pH 7.5, containing 80 mM NaCl. The yield of the purified H5 trimer was 1.5 mg/liter of cell culture.

In vitro cleavage of PA83, H5 and PEx: PA83, PEx and H5 were each labeled with EZ-Link sulfo-NHS-LC-biotin (at a 1:20 protein-biotin molar ratio) for 30 min on ice. Biotin-labeled PA83, PEx and H5 (500 ng each) were co-incubated for 3 h at 37° C. with furin, PC7, PACE4, PC4 and PC5/6 (one unit of activity each). The 100 mM HEPES (pH 7.5), 20 mM Tris-HCl (pH 6.5) and 100 mM sodium acetate (pH 5.5) buffers were supplemented with 1 mM $CaCl_2$ and 0.5 mg/ml BSA. One unit of activity was equal to the amount of the enzyme that was required to cleave 1 pmole/min of the Pyr-RTKR-AMC (SEQ ID NO:273) substrate at 37° C. Where indicated, DEC-RVKR-CMK and the inhibitory peptides were added to the samples. The cleavage was stopped by adding a 5×SDS sample buffer. The digest samples were analyzed by Western Blotting with ExtrAvidin conjugated with horseradish peroxidase and a TMB/M substrate (FIG. 1 and FIG. 3A).

Binding and processing of PA83 by cultured cells: Glioma U251 cells ($3\times10^5$) were incubated for 3 h at 37° C. in serum-free DMEM supplemented with biotin-labeled PA83 (1 μg/ml). Where indicated, DEC-RVKR-CMK (20 μM) and the inhibitory peptides (2-20 μM) were added to the cells. After incubation, cells were washed and lysed in an RIPA buffer (20 mM Tris-HCl, 150 mM NaCl, 0.1% SDS, 1% deoxycholate, 1% IGEPAL, pH 7.4) containing a protease inhibitor cocktail set III, 1 mM phenylmethylsulfonylfluoride and 10 mM EDTA. To determine the concentrations of cell-associated PA83 and PA63, the samples were analyzed by Western blotting with ExtrAvidin conjugated with horseradish peroxidase and a TBM/M substrate (FIG. 1).

Cytotoxicity Assay: Murine macrophage-like cells RAW 264.7 were grown to confluence in wells of a 48-well plate in DMEM supplemented with 10% fetal calf serum. The cells were replenished with fresh medium (0.1 ml/per well) and then incubated with inhibitors for 4 h. To protect the peptide from proteolysis in vivo, the TPRARRRKKRT (SEQ ID NO:212) peptide sequence was amidated at the C-terminus and had β-Ala at the N-terminus. PA83 and LF were then added to the final concentration of 500 ng/ml and 25 ng/ml, respectively. After incubation for an additional hour, cell viability was assessed by 3,[4,5-dimethylthiazol-2-yl]-2,5-diphenyltetrazolium bromide (MTT) staining. Cells were incubated with 0.5 mg/ml MTT in DMEM for 45 min at 37° C.; the medium was aspirated, and the blue pigment produced by the viable cells was solubilized with 0.5% SDS/25 mM HCl in 90% isopropyl alcohol. The concentration of oxidized MTT in the samples was measured at 570 nm using a microplate reader. Each datum point represents the results of at least three independent experiments performed in duplicate. The percentage of viable cells was calculated by using the following equation: (A570 of cells treated with LF, PA83 and inhibitor)−(A570 of cells treated with LF and PA83) (A570 of cells treated with LF alone)−(A570 of cells treated with LF and PA83) (FIG. 1).

The TPRARRRKKRT (SEQ ID NO:212) peptide alone when incubated with cells in concentrations up to 0.5 mM had no effect on cell viability.

Animal experiments with anthrax and Preudomonas PEx: To protect the peptide from proteolysis in vivo, the TPRARRRKKRT (SEQ ID NO:212) peptide sequence was amidated at the C-terminus and had β-Ala at the N-terminus. Purification of anthrax spores and the inhalation model of anthrax using A/J mice was described previously (Sabet, M., et al. 2006; Wu, C.C. N. et al. 2007). A/J mice (8 mice/group) received *B. anthracis* Sterne spores ($4 \times 10^5$/animal in 20 μl PBS). On the day following infection, mice received the TPRARRRKKRT (SEQ ID NO:212) peptide (12.5 mg/kg i.p.) in PBS and then continue to receive injections once daily for the remainder of the experiment. Control mice received an equal volume of PBS. Mice treated with Cipro received 25 mg/kg subcutaneously daily beginning on the fourth day following infection (FIG. 1).

C57/BL6 mice (5 mice/group) received one intramuscular injection of PEx (500 ng/animal; $2 \times LD_{50}$; Fogle, M. R., et al. 2002). Mice received one injection of the TPRARRRKKRT (SEQ ID NO:212) peptide (12.5 mg/kg i.p.) either 24 h prior to toxin injection or simultaneously with toxin. Additional group of mice after receiving one injection of the peptide 24 h prior to toxin injection continued to receive daily injections of the peptide for the remainder of the experiment (FIG. 3B).

Peptides synthesis: A 96-well format centrifugal peptide synthesizer and the techniques for purification and characterization of the peptides were described in detail earlier (Hachmann, J. & Lebl, M. 2006; Kozlov, I. A. et al. 2006; Shiryaev, S. A. et al. 2007). Peptide synthesis was performed in wells of a 96-well flat bottom polypropylene microtiter plate (Evergreen Scientific, Los Angeles, Calif.). The peptides were amidated at the carboxy-terminus. In addition to the C-end amidation, peptides used for their attachment to SNPs exhibited hydroxylaminoacetic acid at the amino-terminus (prepared by attachment of Boc-NHOCH$_2$—COOH at the last step of the synthesis). The use of freshly alumina-treated ether was critical to avoid the loss of the hydroxylamine functionality because of the carbonyl contaminations in ether. The purity of the peptides was confirmed by use of reverse-phase HPLC and also by massspectrometry.

The peptide for the cell-based assays and in vivo studies was synthesized manually in a plastic syringe equipped with a frit (CSPS Pharmaceuticals, San Diego, Calif.) using Rink resin (1 g, 0.45 mmol/g; Novabiochem, San Diego, Calif.). Diisopropylcarbodiimide was used for coupling (2×1 h) and 20% 4-methylpiperidine (Hachmann, J. & Lebl, M. 2006) for Fmoc group deprotection. Final deprotection and cleavage from the resin was performed by Mixture K (King, D. S., et al. 1990). The peptide sample was precipitated by ether, washed by ether (5×), dissolved in 0.1 M HCl and lyophilized. The peptide was then dissolved in 10 ml of 0.1 M HCl and purified on a Sephadex LH-20 column equilibrated in 0.1 M HCl. Fractions containing the peptide were pooled and lyophilized. HPLC (Waters, Milford Mass., USA; μBondapak C18, 10μ particles, 125 Å pore size, 3.9×150 mm, gradient 0.05% TFA in H$_2$0 to 40% acetonitrile, 0.05% TFA in 15 min, flow rate 1.5 ml/min, detection by UV at 217 nm) of the peptide determined the purity of the material to exceed 95%. MS analysis of the synthesized peptide (HT-Labs, San Diego, Calif., USA) confirmed the identity of the product (calculated molecular weight 1495.81 D, found M+H 1497 D).

Protease assays with fluorescence peptides: The assay for PC cleavage activity was performed using a Pyr-RTKR-AMC (SEQ ID NO:273) substrate (24 μM). Enzyme concentrations were 10 nM. The concentrations of the catalytically active proteinases were measured using a fluorescence assay by titration against a standard DEC-RVKR-CMK solution of a known concentration. The buffer for furin cleavage reactions was 100 mM HEPES, pH 7.5, containing 1 mM CaCl$_2$ and 0.5 mg/ml BSA. The buffer for PACE4, PC4, PC5/6 and PC7 was 20 mM Tris-HCl, pH 6.5, supplemented with 1 mM CaCl$_2$. The total assay volume was 0.1 ml. Increasing concentrations of the inhibitory peptides were pre-incubated with the enzymes for 30 min at ambient temperature. The steady state rate of substrate hydrolysis was monitored continuously ($\lambda_{ex}$=360 nm and $\lambda_{em}$=460 nm) using a Spectramax Gemini EM fluorescence spectrophotometer (Molecular Devices, Sunnyvale, Calif.) at 37° C. The IC$_{50}$ values were derived from fitting the V$_0$ vs. log [I]$_t$ plots with sigmoidal dose response curves and the inhibition constant (Ki) was derived using the Cheng-Prusoff equation: $K_i = IC_{50}/(1+[S]/K_m)$, where V$_0$ is the steady state velocity of substrate hydrolysis, [I]$_t$ is the total inhibitor concentration, [S] is the substrate concentration, K$_m$ is the Michaelis-Menten constant, and K$_{i(app)}$ is the apparent inhibition constant (FIG. 1).

Figure 4:
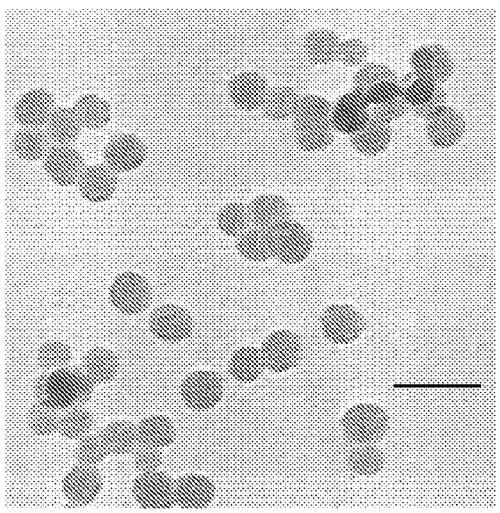
FIG. 4 shows transmission electron microscope image of the amino-functionalized SNPs. Scale bar, 30 nm.
Figure 5:
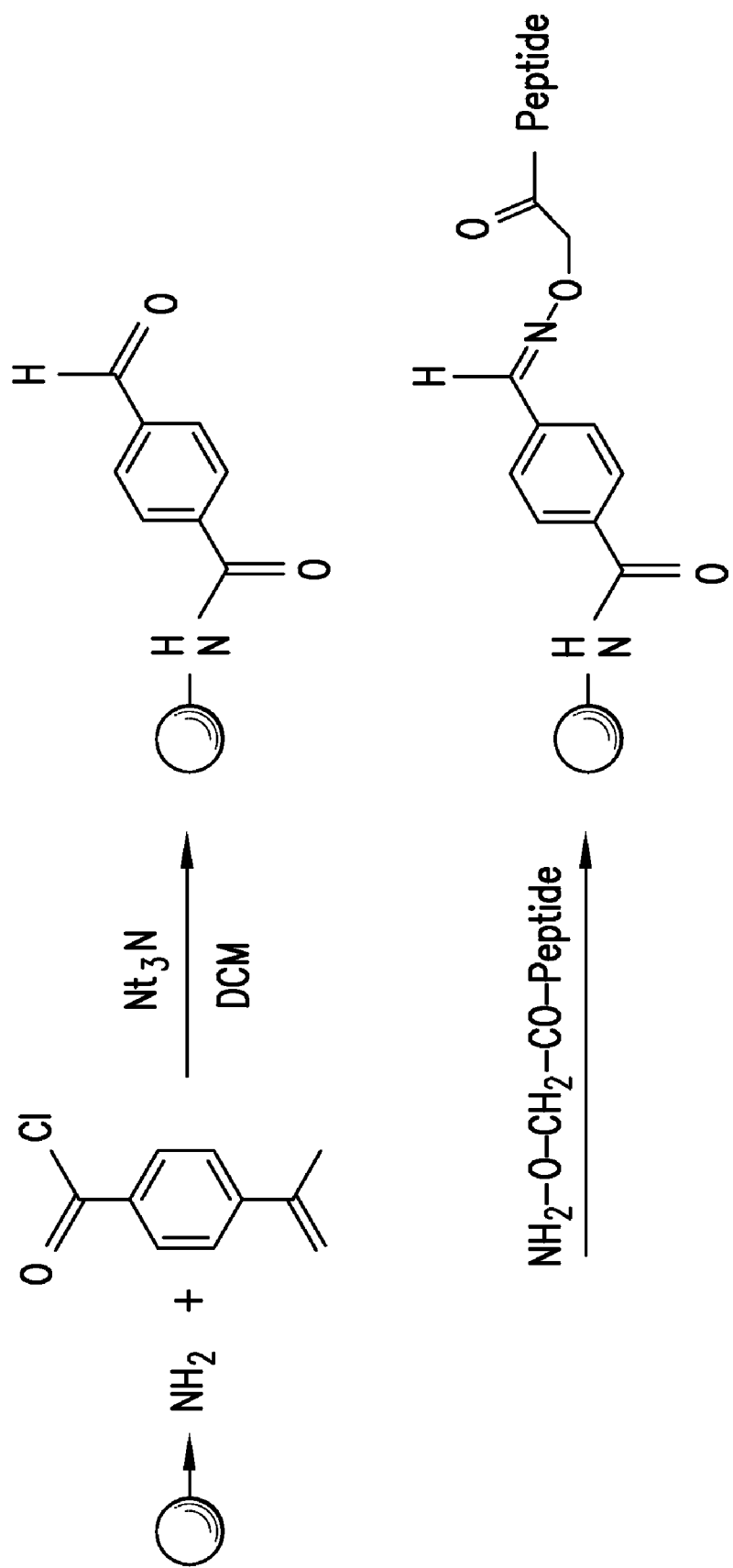
FIG. 5 shows coupling of 4-formylbenzoyl chloride and peptide inhibitors to amino-SNPs. DCM, dimethyl formamide; Et3N, triethylamine.

Preparation of nanoparticles (SNPs) and immobilization of peptides: a cyclohexane, Triton X-100 and n-hexanol 24.8 ml mixture (volume ratio 4.2:1:1) was converted to a nanoemulsion by stirring at room temperature for 1 h. Water (940 μl) and tetramethyl orthosilicate (100.5 μl) were added. The mixture was sonicated for 1 h to facilitate the diffusion of tetramethyl orthosilicate into the encapsulated water droplets in the nanoemulsion. 28% NH3 in water (59 μl) was added to catalyze the hydrolysis of tetramethyl orthosilicate and condensation to form the SNPs. The reaction mixture was stirred for 24 h, followed by the addition of tetramethyl orthosilicate (10.05 μl) and then, in 30 min, aminopropyl trimethoxysilane (11.8 μl). The mixture was stirred for an additional 24 h, and then the amino-SNPs were precipitated by 25 ml acetone washed with water and anhydrous ethanol. The presence of amino groups on SNPs was confirmed by using fluorescamine in methanol followed by sonication of the sample for 5 min at room temperature and fluorescence analysis ($\lambda_{ex}$=390 nm, $\lambda_{em}$=475 nm). An aliquot of SNPs in ethanol was placed on the lacey carbon film covering a 300-mesh copper grid (Ted Pella, Redding, Calif.) and ethanol was then allowed to evaporate. Transmission electron microscope images (FIG. 4) showed the uniform, 15±1 nm diameter, amino-SNPs. Assuming the density of the SNPs is equal to pure silica (1.96 g/cm$^3$), the molecular weight of SNPs was calculated to be 2000 kDa. 4-formylbenzoyl chloride/triethylamine (1:3 molar ratio) was allowed to react with amino-SNPs in dimethyl formamide for 40 min at 0° and then at room temperature overnight (FIG. 5). Aldehyde-SNPs were separated by the addition of water to the sample and extensively washed in water. To accomplish the binding of the peptides to aldehyde-SNPs, a suspension of aldehyde-SNPs (~0.2 mg/0.1 ml) was co-incubated for 48 h in a shaker with 1 mM solution of the peptides (which exhibited a hydroxylamine group) in 1 M citrate buffer, pH 5.1—DMSO mixture (1:1 v/v). Beads were then centrifuged and washed three times with water.

TABLE 2

Alanine scanning mutagenesis of the H5 furin cleavage sequence.

| Peptide | SEQ ID NO | $K_i$, μM | Peptide | SEQ ID NO | $K_i$, μM |
|---|---|---|---|---|---|
| TPRERRRKKR | SEQ ID NO: 1 | >0.1 | TPRERRRKKRV | SEQ ID NO: 47 | >0.1 |
| APRERRRKKR | SEQ ID NO: 2 | >0.1 | APRERRRKKRV | SEQ ID NO: 48 | >0.1 |

TABLE 2-continued

Alanine scanning mutagenesis of the H5 furin cleavage sequence.

| Peptide | SEQ ID NO | $K_i$, µM | Peptide | SEQ ID NO | $K_i$, µM |
|---|---|---|---|---|---|
| TARERRRKKR | SEQ ID NO: 3 | >0.1 | TARERRRKKRV | SEQ ID NO: 49 | >0.1 |
| TPAERRRKKR | SEQ ID NO: 4 | >0.1 | TPAERRRKKRV | SEQ ID NO: 50 | >0.1 |
| TPRARRRKKR | SEQ ID NO: 5 | 0.138 | TPRARRRKKRV | SEQ ID NO: 51 | 0.08 |
| TPREARRKKR | SEQ ID NO: 6 | >0.1 | TPREARRKKRV | SEQ ID NO: 52 | >0.1 |
| TPRERARKKR | SEQ ID NO: 7 | >0.1 | TPRERARKKRV | SEQ ID NO: 53 | >0.1 |
| TPRERRAKKR | SEQ ID NO: 8 | >0.1 | TPRERRAKKRV | SEQ ID NO: 54 | >0.1 |
| TPRERRRAKR | SEQ ID NO: 9 | >0.1 | TPRERRRAKRV | SEQ ID NO: 55 | >0.1 |
| TPRERRRKAR | SEQ ID NO: 10 | >0.1 | TPRERRRKARV | SEQ ID NO: 56 | >0.1 |
| TPRERRRKKA | SEQ ID NO: 11 | >0.1 | TPRERRRKKAV | SEQ ID NO: 57 | >0.1 |
| AARERRRKKR | SEQ ID NO: 12 | >0.1 | AARERRRKKRV | SEQ ID NO: 58 | >0.1 |
| TAAERRRKKR | SEQ ID NO: 13 | >0.1 | TAAERRRKKRV | SEQ ID NO: 59 | >0.1 |
| TPAARRRKKR | SEQ ID NO: 14 | >0.1 | TPAARRRKKRV | SEQ ID NO: 60 | >0.1 |
| TPRAARRKKR | SEQ ID NO: 15 | >0.1 | TPRAARRKKRV | SEQ ID NO: 61 | >0.1 |
| TPREAARKKR | SEQ ID NO: 16 | >0.1 | TPREAARKKRV | SEQ ID NO: 62 | >0.1 |
| TPRERAAKKR | SEQ ID NO: 17 | >0.1 | TPRERAAKKRV | SEQ ID NO: 63 | >0.1 |
| TPRERRAAKR | SEQ ID NO: 18 | >0.1 | TPRERRAAKRV | SEQ ID NO: 64 | >0.1 |
| TPRERRRAAR | SEQ ID NO: 19 | >0.1 | TPRERRRAARV | SEQ ID NO: 65 | >0.1 |
| TPRERRRKAA | SEQ ID NO: 20 | >0.1 | TPRERRRKAAV | SEQ ID NO: 66 | >0.1 |
| AAAERRRKKR | SEQ ID NO: 21 | >0.1 | AAAERRRKKRV | SEQ ID NO: 67 | >0.1 |
| TPAAARRKKR | SEQ ID NO: 22 | >0.1 | TPAAARRKKRV | SEQ ID NO: 68 | >0.1 |
| TPREAAAKKR | SEQ ID NO: 23 | >0.1 | TPREAAAKKRV | SEQ ID NO: 69 | >0.1 |
| TPRERRRKKRG | SEQ ID NO: 109 | >0.1 | TPRERRRKKRs | SEQ ID NO: 70 | >0.1 |
| APRERRRKKRG | SEQ ID NO: 25 | >0.1 | APRERRRKKRs | SEQ ID NO: 71 | >0.1 |
| TARERRRKKRG | SEQ ID NO: 26 | >0.1 | TARERRRKKRs | SEQ ID NO: 72 | >0.1 |
| TPAERRRKKRG | SEQ ID NO: 27 | >0.1 | TPAERRRKKRs | SEQ ID NO: 73 | >0.1 |
| TPRARRRKKRG | SEQ ID NO: 28 | 0.057 | TPRARRRKKRs | SEQ ID NO: 74 | >0.1 |
| TPREARRKKRG | SEQ ID NO: 29 | >0.1 | TPREARRKKRs | SEQ ID NO: 75 | >0.1 |
| TPRERARKKRG | SEQ ID NO: 30 | >0.1 | TPRERARKKRs | SEQ ID NO: 76 | >0.1 |
| TPRERRAKKRG | SEQ ID NO: 31 | >0.1 | TPRERRAKKRs | SEQ ID NO: 77 | >0.1 |
| TPRERRRAKRG | SEQ ID NO: 32 | >0.1 | TPRERRRAKRs | SEQ ID NO: 78 | >0.1 |
| TPRERRRKARG | SEQ ID NO: 33 | >0.1 | TPRERRRKARs | SEQ ID NO: 79 | >0.1 |
| TPRERRRKKAG | SEQ ID NO: 34 | >0.1 | TPRERRRKKAs | SEQ ID NO: 80 | >0.1 |
| AARERRRKKRG | SEQ ID NO: 35 | >0.1 | AARERRRKKRs | SEQ ID NO: 81 | >0.1 |
| TAAERRRKKRG | SEQ ID NO: 36 | >0.1 | TAAERRRKKRs | SEQ ID NO: 82 | >0.1 |
| TPAARRRKKRG | SEQ ID NO: 37 | >0.1 | TPAARRRKKRs | SEQ ID NO: 83 | >0.1 |
| TPRAARRKKRG | SEQ ID NO: 38 | >0.1 | TPRAARRKKRs | SEQ ID NO: 84 | >0.1 |
| TPREAARKKRG | SEQ ID NO: 39 | >0.1 | TPREAARKKRs | SEQ ID NO: 85 | >0.1 |
| TPRERAAKKRG | SEQ ID NO: 40 | >0.1 | TPRERAAKKRs | SEQ ID NO: 86 | >0.1 |

TABLE 2-continued

Alanine scanning mutagenesis of the H5 furin cleavage sequence.

| Peptide | SEQ ID NO | $K_i$, µM | Peptide | SEQ ID NO | $K_i$, µM |
|---|---|---|---|---|---|
| TPRERRAAKRG | SEQ ID NO: 41 | >0.1 | TPRERRAAKRs | SEQ ID NO: 87 | >0.1 |
| TPRERRRAARG | SEQ ID NO: 42 | >0.1 | TPRERRPAARs | SEQ ID NO: 88 | >0.1 |
| TPRERRRKAAG | SEQ ID NO: 43 | >0.1 | TPRERRRKAAs | SEQ ID NO: 89 | >0.1 |
| AAAERRRKKRG | SEQ ID NO: 44 | >0.1 | AAAERRRKKRs | SEQ ID NO: 90 | >0.1 |
| TPAAARRKKRG | SEQ ID NO: 45 | >0.1 | TPAAARRKKRs | SEQ ID NO: 91 | >0.1 |
| TPREAAAKKRG | SEQ ID NO: 46 | >0.1 | TPREAAAKKRs | SEQ ID NO: 92 | >0.1 |

The Ki values were measured with furin and a Pyr-RTKR-AMC (SEQ ID NO: 273) substrate. s, Sarcosin.

TABLE 3

Optimization of the inhibitory peptides.

| Peptide | SEQ ID | $K_i$, µM | Peptide | SEQ ID | $K_i$, µM |
|---|---|---|---|---|---|
| TPQRARRRKKRG | SEQ ID NO: 141 | >0.1 | <u>TPRARRRKKRG</u> | SEQ ID NO: 28 | 0.057 |
| TPQRARRRKKRA | SEQ ID NO: 142 | 0.115 | TPRARRRKKRA | SEQ ID NO: 203 | >0.1 |
| <u>TPQRARRRKKRV</u> | SEQ ID NO: 143 | 0.048 | <u>TPRARRRKKRV</u> | SEQ ID NO: 204 | 0.08 |
| TPQRARRRKKRL | SEQ ID NO: 144 | >0.1 | TPRARRRKKRL | SEQ ID NO: 205 | >0.1 |
| TPQRARRRKKRI | SEQ ID NO: 145 | >0.1 | <u>TPRARRRKKRI</u> | SEQ ID NO: 206 | 0.03 |
| TPQRARRRKKRP | SEQ ID NO: 146 | >0.1 | TPRARRRKKRP | SEQ ID NO: 207 | >0.1 |
| <u>TPQRARRRKKRF</u> | SEQ ID NO: 147 | 0.044 | TPRARRRKKRF | SEQ ID NO: 208 | 0.038 |
| <u>TPQRARRRKKRW</u> | SEQ ID NO: 148 | 0.034 | <u>TPRARRRKKRW</u> | SEQ ID NO: 209 | 0.059 |
| <u>TPQRARRRKKRM</u> | SEQ ID NO: 149 | 0.058 | TPRARRRKKRM | SEQ ID NO: 210 | >0.1 |
| TPQRARRRKKRS | SEQ ID NO: 150 | >0.1 | TRRARRRKKRS | SEQ ID NO: 211 | >0.1 |
| <u>TPQRARRRKKRT</u> | SEQ ID NO: 151 | 0.033 | <u>TPRARRRKKRT</u> | SEQ ID NO: 212 | 0.023 |
| TPQRARRRKKRC | SEQ ID NO: 152 | >0.1 | TPRARRRKKRC | SEQ ID NO: 213 | >0.1 |
| <u>TPQRARRRKKRY</u> | SEQ ID NO: 153 | 0.047 | <u>TPRARRRKKRY</u> | SEQ ID NO: 214 | 0.053 |
| TPQRARRRKKRN | SEQ ID NO: 154 | >0.1 | <u>TPRARRRKKRN</u> | SEQ ID NO: 215 | 0.045 |
| TPQRARRRKKRQ | SEQ ID NO: 155 | >0.1 | <u>TPRARRRKKRQ</u> | SEQ ID NO: 216 | 0.047 |
| <u>TPQRARRRKKRD</u> | SEQ ID NO: 156 | 0.05 | TRRARRRKKRD | SEQ ID NO: 217 | 0.056 |
| TPQRARRRKKRE | SEQ ID NO: 157 | 0.103 | TPRARRRKKRE | SEQ ID NO: 218 | >0.1 |
| TPQRARRRKKRH | SEQ ID NO: 158 | >0.1 | TPRARRRKKRH | SEQ ID NO: 219 | >0.1 |
| TPQRARRRKKRK | SEQ ID NO: 159 | >0.1 | TPRARRRKKRK | SEQ ID NO: 220 | >0.1 |
| TPQRARRRKKRR | SEQ ID NO: 160 | >0.1 | TPRARRRKKRR | SEQ ID NO: 221 | >0.1 |
| TPQRARRRKKR1 | SEQ ID NO: 161 | >0.1 | | | |
| TPQRARRRKKR2 | SEQ ID NO: 162 | >0.1 | | | |
| TPQRARRRKKR3 | SEQ ID NO: 163 | >0.1 | <u>TPRARRRKKR5</u> | SEQ ID NO: 222 | 0.065 |
| <u>TPQRARRRKKR5</u> | SEQ ID NO: 164 | 0.093 | <u>TPRARRRKKR6</u> | SEQ ID NO: 223 | 0.081 |
| TPQRARRRKKR6 | SEQ ID NO: 165 | >0.1 | | | |
| TPQRARRRKKRk | SEQ ID NO: 166 | >0.1 | | | |
| TPQRARRRKKRr | SEQ ID NO: 167 | >0.1 | | | |

TABLE 3-continued

Optimization of the inhibitory peptides.

| Peptide | SEQ ID | $K_i$, μM | Peptide | SEQ ID | $K_i$, μM |
|---|---|---|---|---|---|
| TPQRARRRKKrG | SEQ ID NO: 168 | >0.1 | | | |
| TPQRARRRKKkG | SEQ ID NO: 169 | >0.1 | | | |
| TPQRARRRKK4G | SEQ ID NO: 170 | >0.1 | <u>TPRARRRKKRG</u> | SEQ ID NO: 28 | 0.057 |
| TPQRARRRKKRG | SEQ ID NO: 171 | >0.1 | TPRCRRRKKRG | SEQ ID NO: 104 | >0.1 |
| TPQRCRRRKKRG | SEQ ID NO: 172 | >0.1 | TPRDRRRKKRG | SEQ ID NO: 108 | >0.1 |
| TPQRDRRRKKRG | SEQ ID NO: 173 | >0.1 | TPRERRRKKRG | SEQ ID NO: 109 | >0.1 |
| TPQRERRRKKRG | SEQ ID NO: 174 | >0.1 | TPRFRRRKKRG | SEQ ID NO: 99 | >0.1 |
| TPQRFRRRKKRG | SEQ ID NO: 175 | >0.1 | <u>TPRGRRRKKRG</u> | SEQ ID NO: 94 | 0.047 |
| TPQRGRRRKKRG | SEQ ID NO: 176 | >0.1 | TPRHRRRKKRG | SEQ ID NO: 111 | >0.1 |
| TPQRHRRRKKRG | SEQ ID NO: 177 | >0.1 | TPRIRRRKKRG | SEQ ID NO: 97 | >0.1 |
| TPQRIRRRKKRG | SEQ ID NO: 178 | >0.1 | TPRKRRRKKRG | SEQ ID NO: 112 | >0.1 |
| TPQRKRRRKKRG | SEQ ID NO: 179 | >0.1 | TPRLRRRKKRG | SEQ ID NO: 96 | >0.1 |
| TPQRLRRRKKRG | SEQ ID NO: 180 | >0.1 | TPRMRRRKKRG | SEQ ID NO: 101 | >0.1 |
| TPQRMRRRKKRG | SEQ ID NO: 181 | >0.1 | TPRNRRRKKRG | SEQ ID NO: 106 | >0.1 |
| TPQRNRRRKKRG | SEQ ID NO: 182 | >0.1 | TPRPRRRKKRG | SEQ ID NO: 98 | >0.1 |
| TPQRPRRRKKRG | SEQ ID NO: 183 | >0.1 | TPRQRRRKKRG | SEQ ID NO: 107 | >0.1 |
| TPQRQRRRKKRG | SEQ ID NO: 184 | >0.1 | TPRRRRRKKRG | SEQ ID NO: 113 | >0.1 |
| TPQRRRRRKKRG | SEQ ID NO: 185 | >0.1 | TPRSRRRKKRG | SEQ ID NO: 102 | >0.1 |
| TPQRSRRRKKRG | SEQ ID NO: 186 | >0.1 | TPRTRRRKKRG | SEQ ID NO: 103 | >0.1 |
| TPQRTRRRKKRG | SEQ ID NO: 187 | >0.1 | TPRVRRRKKRG | SEQ ID NO: 95 | >0.1 |
| TPQRVRRRKKRG | SEQ ID NO: 188 | >0.1 | TPRWRRRKKRG | SEQ ID NO: 100 | >0.1 |
| TPQRWRRRKKRG | SEQ ID NO: 189 | >0.1 | TPRYRRRKKRG | SEQ ID NO: 105 | >0.1 |
| TPQRYRRRKKRG | SEQ ID NO: 190 | >0.1 | TPR1RRRKKRG | SEQ ID NO: 114 | >0.1 |
| TPQR1RRRKKRG | SEQ ID NO: 191 | >0.1 | TPR2RRRKKRG | SEQ ID NO: 115 | >0.1 |
| TPQR2RRRKKRG | SEQ ID NO: 192 | >0.1 | TPR3RRRKKRG | SEQ ID NO: 116 | >0.1 |
| TPQR3RRRKKRG | SEQ ID NO: 193 | >0.1 | TPR4RRRKKRG | SEQ ID NO: 117 | >0.1 |
| TPQR4RRRKKRG | SEQ ID NO: 194 | >0.1 | TPReRRRKKRG | SEQ ID NO: 118 | >0.1 |
| TPQReRRRKKRG | SEQ ID NO: 195 | >0.1 | TPRkRRRKKRG | SEQ ID NO: 119 | >0.1 |
| TPQRkRRRKKRG | SEQ ID NO: 196 | >0.1 | | | |
| TPQRrRRRKKRG | SEQ ID NO: 197 | >0.1 | | | |
| TPQR5RRRKKRG | SEQ ID NO: 198 | >0.1 | | | |
| TPQR6RRRKKRG | SEQ ID NO: 199 | >0.1 | | | |
| TPQR7RRRKKRG | SEQ ID NO: 200 | >0.1 | | | |
| TPQR8RRRKKRG | SEQ ID NO: 201 | >0.1 | | | |
| TPQR4RRRKK4G | SEQ ID NO: 202 | >0.1 | | | |

The $K_i$ values were measured with furin and a Pyr-RTKR-AMC (SEQ ID NO: 273) substrate.
The most efficient inhibitory peptides are underlined. e, D-Glu; k, D-Lys; r, D-Arg; s, Sarcosin; 1, β-Ala; 2, ε-aminohexanoic acid; 3, aminocyclopentanecarboxylic acid; 4, Citrullin; 5, Cys(Me); 6, Nle; 7, cyclohexylalanine; 8, α-amino-butyric acid.

TABLE 4

Furin Targets

| | | P6 P4' | SEQ ID | Site |
|---|---|---|---|---|
| FURIN | Furin, two autolytic cleavage sites | RGVTKRSLSP | SEQ ID NO: 229 | 75-76 |
| FUIRIN | Furin, two autolytic cleavage sites | KRRTKRDVYQ | SEQ ID NO: 230 | 107-108 |
| MMP-1 | Matrix metalloproteinase 1, collagenase-1 | VMKQKRCGVP | SEQ ID NO: 231 | 91-92 |
| MMP-2 | Matrix metalloproteinase 2, gelatinase A | TMRKPRCGNP | SEQ ID NO: 232 | 101-102 |
| MMP-3 | Matrix metalloproteinase 3, stromelysin-1 | VMRKPRCGVP | SEQ ID NO: 233 | 91-92 |
| MMP-8 | Matrix metalloproteinase 8, collagenase-2 | MMKKPRCGVP | SEQ ID NO: 234 | 90-91 |
| MMP-9 | Matrix metalloproteinase 9, gelatinase B | AMRTPRCGVP | SEQ ID NO: 235 | 98-99 |
| MMP-10 | Matrix metalloproteinase 10, stromelysin-2 | VMRKPRCGVP | SEQ ID NO: 236 | 90-91 |
| MMP-11 | Matrix metalloproteinase 11, stromelysin-3 | RNRQKRFVLS | SEQ ID NO: 237 | 97-98 |
| MMP-13 | Matrix metalloproteinase 13, collagenase-3 | VMKKPRCGVP | SEQ ID NO: 238 | 95-96 |
| MMP-14 | Matrix metalloproteinase 14, MT1-MMP | NVRRKRYAIQ | SEQ ID NO: 239 | 111-112 |
| MMP-15 | Matrix metalloproteinase 15, MT2-MMIP | RRRRKRYALT | SEQ ID NO: 240 | 131-132 |
| MMP-16 | Matrix metalloproteinase 16, MT3-MMP | HTRRKRYALT | SEQ ID NO: 241 | 119-120 |
| MMP-17 | Matrix metalloproteinase 17, MT4-MMP | QARRRQAPA | SEQ ID NO: 242 | 125-126 |
| MMP-24 | Matrix metalloproteinase 24, MT5-MMP | RRRNKRYALT | SEQ ID NO: 243 | 155-156 |
| MMP-25 | Matrix metalloproteinase 25, MT6-MMP | VRRRRRYALS | SEQ ID NO: 244 | 107-108 |
| MMP-21 | Matrix metalloproteinase 21 | RARSRRSPRA | SEQ ID NO: 245 | 144-145 |
| MMP-28 | Matrix metalloproteinase 28 | MRRKRRFAKQ | SEQ ID NO: 246 | 122-123 |
| ADAM-1 | A desintegrin and metallopeptidase domain 1 | PPRSRKPDDL | SEQ ID NO: 247 | murine |
| ADAM-8 | A desintegrin and metallopeptidase domain 8 | PSRETRYVEL | SEQ ID NO: 248 | 200-201 |
| ADAM-9 | A desintegrin and metallopeptidase domain 9 | LLRRRAVLE | SEQ ID NO: 249 | 205-206 |
| ADAM-10 | A desintegrin and metallopeptidase domain 10 | LLRKKRTTSA | SEQ ID NO: 250 | 213-214 |
| ADAM-12 | A desintegrin and metallopeptidase domain 12 | ARRHKRETLK | SEQ ID NO: 251 | 207-208 |
| ADAM-15 | A desintegrin and metallopeptidase domain 15 | HIRRRRDVVT | SEQ ID NO: 252 | 206-207 |
| ADAM-17 | TACE (TNFalpha coverting enzyme) | VHRVKRRADP | SEQ ID NO: 253 | 214-215 |
| ADAM-19 | A desintegrin and metallopeptidase domain 19 | PRRMKREDLN | SEQ ID NO: 254 | 105-106 |
| ADAMTS1 | A desintegrin and metalloproteinase with thrombospondin type-1 motif, 1 | SIRKKRFVSS | SEQ ID NO: 255 | 252-253 |
| ADAMTS-2 | A desintegrin and metalloproteinase with thrombospondin type-1 motif, 2, isoform 1/2 | GVRARRAAPA | SEQ ID NO: 256 | 88-89 |
| ADAMTS-2 | A desintegrin and metalloproteinase with thrombospondin type-i motif, 2, isoform 1 | RRRARRHAAD | SEQ ID NO: 257 | 259-260 |
| ADAMTS-3 | A desintegrin and metalloproteinase with thrombospondin type-i motif, 3 | TMRRRRHAGE | SEQ ID NO: 258 | 249-250 |
| ADAMTS4 | A desintegrin and metalloproteinase with thrombospondin type-1 motif (aggrecanase-1), 4 | PRRAKRFASL | SEQ ID NO: 259 | 212-213 |
| ADAMTS-5/11 | A desintegrin and metalloproteinase with thrombospondin type-i motif, 5/11 | WRRRRRSISR | SEQ ID NO: 260 | 261-262 |

TABLE 4-continued

Furin Targets

| Gene | Name | P6 P4' | SEQ ID | Site |
|---|---|---|---|---|
| ADAMTS13 | A desintegrin and metalloproteinase with thrombospondin type-1 motif. 13 | RQRQRPAAGG | SEQ ID NO: 261 | 74-75 |
| BMP1 | Bone morphogenetic protein 1 | RSRSPPAATS | SEQ ID NO: 262 | 120-121 |
| BMP4 | Bone morphogenetic protein 4 | RRPAKRSPKH | SEQ ID NO: 263 | 292-293 |
| Meprin-A | Meprin A alpha | PSRQKRSVEN | SEQ ID NO: 264 | 653-654 |
| BACE1 | Beta-site APP-cleaving enzyme 1 | GLRLPRETDE | SEQ ID NO: 265 | 45-46 |
|  | Albumin | RGVFRRDAHK | SEQ ID NO: 266 | 24-25 |
| VWF | von Willebrand factor | SHRSKRSLSC | SEQ ID NO: 267 | 763-764 |
| F9 | Coagulation factor IX | LNRPKRYNSG | SEQ ID NO: 268 | 46-47 |
| PROC | Protein C | RSHLKRDTED | SEQ ID NO: 269 | 199-200 |
| FBN1 | Fibrillin 1 | RGRKRRSTNE | SEQ ID NO: 270 | 2731-2732 |
| ZPC3 | Zona pellucida glycoprotein 3 | ASRNRRHVTE | SEQ ID NO: 271 | 301-302 |
| 7B2 | Secretogranin V | QRRKRRSVNP | SEQ ID NO: 272 | 181-182 |
| ITGA3 | Integrin alpha chain, alpha 3 | PQRRRRQLDP | SEQ ID NO: 274 | 875-876 |
| ITGA4 | Integrin alpha chain, alpha 4 | HVISKRSTEE | SEQ ID NO: 275 | 591-592 |
| ITGA5 | integrin alpha chain, alpha 5 | HHQQKREAPS | SEQ ID NO: 276 | 894-895 |
| ITGA6 | Integrin alpha chain, alpha 6 | NSRKKREITE | SEQ ID NO: 277 | 902-903 |
| ITGA7 | Integrin alpha chain, alpha 7 | RDRRRRELEP | SEQ ID NO: 278 | 914-915 |
| ITGA8 | Integrin alpha chain, alpha 8 | HLVRKRDVHV | SEQ ID NO: 279 | 906-907 |
| ITGAV | Integrin alpha chain, alpha V | HLITKRDLAL | SEQ ID NO: 280 | 940-941 |
| ITGAIIB | Integrin alpha IIb precursor | NKRDRRQIFL | SEQ ID NO: 281 | 890-891 |
| LRP1 | Low density lipoprotein-related protein 1 | SNRHRRQIDR | SEQ ID NO: 282 | 3943-3944 |
| NOTCH1 | Notch1 | GGRRRRELDP | SEQ ID NO: 283 | 1665-1666 |
| INSR | Insulin receptor | PSRKRRSLGD | SEQ ID NO: 284 | 762-763 |
| DSG3 | Desmoglein 3 | KRRQKREWVK | SEQ ID NO: 285 | 49-50 |
| CUBN | Cubilin/ Vitamin B-12 receptor | LQRQKRSINL | SEQ ID NO: 286 | 35-36 |
| SORL1 | Sortilin-related receptor | PLRRKRSAAL | SEQ ID NO: 287 | 81-82 |
| HGFR | Hepatocyte growth factor c-met/Scatter factor receptor | EKRKKRSTKK | SEQ ID NO: 288 | 307-308 |
| IGE-1a | Insulin-like growth factor 1a/somatomedin C | PAKSARSVPA | SEQ ID NO: 289 | 119-120 |
| IGF-2 | Insulin-like growth factor 2 | PAKSERDVST | SEQ ID NO: 290 | 92-93 |
| PDGF-A | Platelet-derived growth factor A | PIRRKRSIEE | SEQ ID NO: 291 | 86-87 |
| PDGF-B | Platelet-derived growth factor B isoform 1 | LARGRRSLGS | SEQ ID NO: 292 | 81-82 |
| PDGF-B | Platelet-derived growth factor B isoform 2 | LARGRRSLGS | SEQ ID NO: 293 | 66-67 |
| PDGF-C | Platelet-derived growth factor C | FGRKSRVVDL | SEQ ID NO: 294 | 234-235 |
| PDGF-D | Platelet-derived growth factor D, isoform 1 | HDRKSKVDLD | SEQ ID NO: 295 | 257-258 |
| PDGF-D | Platelet-derived growth factor D, isoform 2 | HDRKSKVDLD | SEQ ID NO: 296 | 251-252 |
| NTF3 | Neurotrophin 3 | TSRRKRYAEH | SEQ ID NO: 297 | 138-139 |
| NTF4/5 | Neurotrophin 4/5 | ANRSRRGVSE | SEQ ID NO: 298 | 79-80 |
| VEGFC | Vascular endothelial growth factor C | HSIIRRSLPA | SEQ ID NO: 299 | 227-228 |

TABLE 4-continued

Furin Targets

| | | P6 P4' | SEQ ID | Site |
|---|---|---|---|---|
| VEGFD | Vascular endothelial growth factor D | YSIIRRSIQI | SEQ ID NO: 300 | 205-206 |
| FGF-23 | Fibroblast growth factor 23 | PRRHTRSAED | SEQ ID NO: 301 | 179-180 |
| NPPB | Natriuretic peptide B | TLRAPRSPKM | SEQ ID NO: 302 | 102-103 |
| PTH | Parathyroid hormone | KSVKKRSVSE | SEQ ID NO: 303 | 31-32 |
| TGFB1 | Transforming growth factor, beta 1 | SSRHRRALDT | SEQ ID NO: 304 | 278-279 |
| TNFSF12-TNFSF13 | Tumor necrosis factor (ligand) member 12-member 13/ proliferation-inducing ligand APRIL | RSRKRRAVLT | SEQ ID NO: 305 | 104-105 |
| EDA-A2 | Ectodysplasin a isoform | VRRNKRSKSN | SEQ ID NO: 306 | 159-160 |
| NGFB | b-Nerve growth factor | THRSKRSSSH | SEQ ID NO: 307 | 179-180 |
| | Semaphorin 3A | KRRTRRQDIR | SEQ ID NO: 308 | 555-556 |
| END | Endothelin-1 | LRRSKRCSCS | SEQ ID NO: 309 | 52-53 |
| PTHRP | Parathyroid hormone-related protein precursor | SRRLKRAVSE | SEQ ID NO: 310 | 36-37 |
| TGFB4 | Lefty protein/endometrial bleeding associated factor | RSRGKRFSQS | SEQ ID NO: 311 | 77-78 |
| BDNF | Brain-derived neurotrophic factor | SMRVRRHSDP | SEQ ID NO: 312 | 128-129 |
| APRIL | A proliferation inducing ligand | RSRKRRAVLT | SEQ ID NO: 313 | 104-105 |
| BAFF | Tumor necrosis factor ligand superfamily member 13B (TALL-1)/B cell-activating factor (BAFF) | NSRNKRAVQG | SEQ ID NO: 314 | 133-134 |
| HB-EGF | Heparin-binding EGF-like growth factor | RDRKVRDLQE | SEQ ID NO: 315 | 62-63 |
| HGF | Hepatocyte growth factor isoform 1 | KTKQLRVVNG | SEQ ID NO: 316 | 494-495 |
| | PANCREATIC POLYPEPTIDE | PRYGKRHKED | SEQ ID NO: 317 | 68-69 |
| | GASTRIN | ASHHRRQLGP | SEQ ID NO: 318 | 58-59 |
| | PROENKEPHALIN | GGFMKKDAEE | SEQ ID NO: 319 | 142-143 |
| | PROENKEPHALTIN | MRGLKRSPQL | SEQ ID NO: 320 | 195-196 |
| | PROENKEPHALIN PEPTIDE B | GGFLKRFAEA | SEQ ID NO: 321 | 236-237 |
| | beta-neoendorphin-dynorphin A 1-17 (C-terminal) | WDNQKRYGGF | SEQ ID NO: 322 | 225-226 |
| | beta-neoendorphin-dynorphin A 1-18 (C-terminal) | FLRRTRPKLK | SEQ ID NO: 323 | 215-216 |
| POMC | Proopiomelanocortin, a-MSH (C-terminal) | VGKKRRPVKV | SEQ ID NO: 324 | 155-156 |
| POMC | Proopiomelanocortin, b-ENDORPHIN (N terminal) | PPKDKRYGGF | SEQ ID NO: 325 | 236-237 |
| POMC | Proopiomelanocortin, ACTH (C-terminal) | PLEFKRELTG | SEQ ID NO: 326 | 178-179 |
| HO | Hemagglutinin type H5 | RRRKKRGLFG | SEQ ID NO: 327 | 344-345 |
| F | Newcastle disease virus F fusion protein | GRRQKRLIGA | SEQ ID NO: 328 | 116-117 |
| F | Parainfluenza HPIV3 F fusion protein | DPRTKRFFGG | SEQ ID NO: 329 | 109-110 |
| P130 | Sindbis virus structural polyprotein p130 | SGRSKRSVID | SEQ ID NO: 330 | 328-329 |
| prm | Flaviviral prM protein (Dengue type 2) | HRREKRSVAL | SEQ ID NO: 331 | 205-206 |
| prM | Flaviviral prM protein (West Nile) | SRRSRRSLTV | SEQ ID NO: 332 | 215-216 |
| UL55 | Cytomegalovirus/Herpesvirus S protein ULSS/glycoprotein B | THRTKRSTDG | SEQ ID NO: 333 | 460-461 |
| gp160 | HIV-1 glycoprotein-160 | VQREKRAVGL | SEQ ID NO: 334 | 498-499 |
| Fo | Measles virus fusion protein | SRRHKRFAGV | SEQ ID NO: 335 | 115-116 |
| E2 | Infectious bronchitis spike protein | TRRFRRSITE | SEQ ID NO: 336 | 537-538 |

TABLE 4-continued

Furin Targets

| | | P6 P4' | SEQ ID | Site |
|---|---|---|---|---|
| GP | Marburg virus spike glycoprotein | YFRRKRSILW | SEQ ID NO: 337 | 435-436 |
| env | Ebola envelope glycoprotein | GRRTRREAIV | SEQ ID NO: 338 | 501-502 |
| BALF4/GP110 | Epstein-Barr virus/herpesvirus 4 | LRRRRRDAGN | SEQ ID NO: 339 | 432-433 |
| ExoA | *Pseudomonas aeruginosa* exotoxin A | RHRQPRGWEQ | SEQ ID NO: 340 | 304-305 |
| PA83 | Anthrax protective antigen | NSRKKRSTSA | SEQ ID NO: 341 | 196-197 |
| a-toxin | *Clostridium* alpha-toxin | KRRGKRSVDS | SEQ ID NO: 342 | 398-399 |
| DT | Diphtheria toxin | GNRVRRSVGS | SEQ ID NO: 343 | 218-219 |
| Aerolysin | *Aeromonas* aerolysin | KVRRARSVDG | SEQ ID NO: 344 | 455-456 |
| Shiga toxin | *Shigella* shiga toxin I subunit A | ASRVARMASD | SEQ ID NO: 345 | 273-274 |

TABLE 5

Peptides shown to be effective

| Peptide | SEQ ID | Comments |
|---|---|---|
| X1 -RX2RRRKKR-X3 | SEQ ID NOs: 346, 371, 372, and 373 | X1 = TP or TPQ<br>X2 = A or G<br>X3 = any or none |
| TP -RARRRKKR | SEQ ID NO: 5 | |
| TP -RARRRKKR-G | SEQ ID NO: 28 | |
| TP -RARRRKKR-V | SEQ ID NO: 51 | |
| TP -RGRRRKKR-G | SEQ ID NO: 94 | |
| TPQ-RARRRKKR-A | SEQ ID NO: 142 | |
| TPQ-RARRRKKR-V | SEQ ID NO: 143 | |
| TPQ-RARRRKKR-F | SEQ ID NO: 147 | |
| TPQ-RARRRKKR-W | SEQ ID NO: 148 | |
| TPQ-RARRRKKR-M | SEQ ID NO: 149 | |
| TPQ-RARRRKKR-T | SEQ ID NO: 151 | |
| TPQ-RARRRKKR-Y | SEQ ID NO: 153 | |
| TPQ-RARRRKKR-D | SEQ ID NO: 156 | |
| TPQ-RARRRKKR-5 | SEQ ID NO: 164 | 5 = Cys (Me) |
| TP -RARRRKKR-V | SEQ ID NO: 204 | |
| TP -RARRRKKR-I | SEQ ID NO: 206 | |
| TP -RARRRKKR-F | SEQ ID NO: 208 | |
| TP -RARRRKKR-W | SEQ ID NO: 209 | |
| TP -RARRRKKR-T | SEQ ID NO: 212 | |
| TP -RARRRKKR-Y | SEQ ID NO: 214 | |
| TP -RARRRKKR-N | SEQ ID NO: 215 | |
| TP -RARRRKKR-Q | SEQ ID NO: 216 | |
| TP -RARRRKKR-D | SEQ ID NO: 217 | |
| TP -RARRRKKR-5 | SEQ ID NO: 222 | 5 = Cys (Me) |
| TP -RARRRKKR-6 | SEQ ID NO: 223 | 6 = Nle |

2. Example 2

N-terminal Truncations

The best inhibitory peptide (TPRARRRKKRT, Ki=15.8 nM against furin) was further shortened from the N-end. The table data show the Ki values of the N-end deletions of this peptide against furin using pyroglutamic acid-Arg-Thr-Lys-Arg-methyl-coumaryl-7-amide (Pyr-RTKR-AMC; SEQ ID NO:273) as a substrate. The deletion of both Thr and Pro results in RARRRKKRT (SEQ ID NO:366) that has the Ki=8 nM. The further deletions made the Ki worse.

TABLE 6

N-terminal deletions

| PEPTIDE | SEQ ID NO | Ki (nM) |
|---|---|---|
| TPRARRRKKRT | SEQ ID NO: 212 | 15.8 |
| PRARRRKKRT | SEQ ID NO: 365 | 16.6 |
| RARRRKKRT | SEQ ID NO: 366 | 8.0 |
| ARRRKKRT | SEQ ID NO: 367 | 11.1 |
| RRRKKRT | SEQ ID NO: 368 | 17.6 |
| RRKKRT | SEQ ID NO: 369 | 32.5 |
| RKKRT | SEQ ID NO: 370 | 1000 |

H. REFERENCES

Basak, A., Zhong, M., Munzer, J. S., Chretien, M. & Seidah, N. G. Biochem J 353, 537-45 (2001).

Chen, J. et al. Cell 95, 409-17 (1998).

Chiron, M. F., Fryling, C. M. & FitzGerald, D. J Biol Chem 272, 31707-11 (1997).

Collier, R. J. & Young, J. A. Annu Rev Cell Dev Biol 19, 45-70 (2003).

Fogle, M. R., Griswold, J. A., Oliver, J. W. & Hamood, A. N. Anti-ETA IgG neutralizes the effects of Pseudomonas aeruginosa exotoxin A. J Surg Res 106, 86-98 (2002).

Forino, M. et al. Proc Natl Acad Sci USA 102, 9499-504 (2005).

Fugere, M. & Day, R. Trends Pharmacol Sci 26, 294-301 (2005).

Fugere, M. et al. Inhibitory potency and specificity of subtilase-like pro-protein convertase (SPC) prodomains. J Biol Chem 277, 7648-56 (2002).

Hachmann, J. & Lebl, M. Alternative to piperidine in Fmoc solid-phase synthesis. J Comb Chem 8, 149 (2006).

Hachmann, J. & Lebl, M. Search for optimal coupling reagent in multiple peptide synthesizer. Biopolymers 84, 340-7 (2006).

Jiao, G. S. et al. Proc Natl Acad Sci USA 103, 19707-12 (2006).

King, D. S., Fields, C. G. & Fields, G. B. A cleavage method which minimizes side reactions following Fmoc solid phase peptide synthesis. Int J Pept Protein Res 36, 255-66 (1990).

Kozlov, I. A. et al. A method for rapid protease substrate evaluation and optimization. Comb Chem High Throughput Screen 9, 481-7 (2006).

Lin, Y. W., Liu, C. W. & Chang, H. T. J Nanosci Nanotechnol 6, 1092-100 (2006).

Remacle, A. G., Rozanov, D. V., Fugere, M., Day, R. & Strongin, A. Y. Oncogene 25, 5648-55 (2006).

Sabet, M., Cottam, H. B. & Guiney, D. G. Modulation of cytokine production and enhancement of cell viability by TLR7 and TLR9 ligands during anthrax infection of macrophages. FEMS Immunol Med Microbiol 47, 369-79 (2006).

Scamuffa, N., Calvo, F., Chretien, M., Seidah, N. G. & Khatib, A. M. Faseb J 20, 1954-63 (2006).

Shiryaev, S. A. et al. Cleavage preference distinguishes the two-component NS2B-NS3 serine proteinases of Dengue and West Nile viruses. Biochem J 401, 743-52 (2007).

Stevens, J. et al. Science 303, 1866-70 (2004).

Subbarao, K. et al. Science 279, 393-6 (1998).

Wu, C. C. N. et al. Immunotherapeutic activity of a novel conjugate of a toll-like receptor 7 ligand. Proc Natl Acad Sci USA in press (2007).

Yang, H. H. et al. Anal Chem 77, 354 (2005).

What is claimed is:

1. An isolated peptide comprising the amino acid sequence $X_1RX_2RRRKKRX_3$, wherein $X_1$ is TP or TPQ, wherein $X_2$ is A or G, and $X_3$ is any or no amino acid (SEQ ID NOs: 346, 371, 372 and 373), wherein the peptide is less than or equal to 200 amino acids in length.

2. The isolated peptide of claim 1 comprising the amino acid sequence SEQ ID NO:5, SEQ ID NO:28, SEQ ID NO:51, SEQ ID NO:94, SEQ ID NO:142, SEQ ID NO:143, SEQ ID NO:147, SEQ ID NO:148, SEQ ID NO:149, SEQ ID NO:151, SEQ ID NO:153, SEQ ID NO:156, SEQ ID NO:164, SEQ ID NO:204, SEQ ID NO:206, SEQ ID NO:208, SEQ ID NO:209, SEQ ID NO:212, SEQ ID NO:214, SEQ ID NO:215, SEQ ID NO:216, SEQ ID NO:217, SEQ ID NO:222, or SEQ ID NO:223.

3. An isolated nucleic acid encoding the peptide of claim 1 or 2.

4. The isolated peptide of claim 1, wherein the peptide is less than about 100 amino acids in length.

5. The isolated peptide of claim 1, wherein the peptide is less than about 95 amino acids in length.

6. The isolated peptide of claim 1, wherein the peptide is less than about 90 amino acids in length.

7. The isolated peptide of claim 1, wherein the peptide is less than about 85 amino acids in length.

8. The isolated peptide of claim 1, wherein the peptide is less than about 80 amino acids in length.

9. The isolated peptide of claim 1, wherein the peptide is less than about 75 amino acids in length.

10. The isolated peptide of claim 1, wherein the peptide is less than about 70 amino acids in length.

11. The isolated peptide of claim 1, wherein the peptide is less than about 65 amino acids in length.

12. The isolated peptide of claim 1, wherein the peptide is less than about 60 amino acids in length.

13. The isolated peptide of claim 1, wherein the peptide is less than about 55 amino acids in length.

14. The isolated peptide of claim 1, wherein the peptide is less than about 50 amino acids in length.

15. The isolated peptide of claim 1, wherein the peptide is less than about 45 amino acids in length.

16. The isolated peptide of claim 1, wherein the peptide is less than about 40 amino acids in length.

17. The isolated peptide of claim 1, wherein the peptide is less than about 35 amino acids in length.

18. The isolated peptide of claim 1, wherein the peptide is less than about 30 amino acids in length.

19. The isolated peptide of claim 1, wherein the peptide is less than about 25 amino acids in length.

20. The isolated peptide of claim 1, wherein the peptide is less than about 20 amino acids in length.

21. The isolated peptide of claim 1, wherein the peptide is less than about 15 amino acids in length.

* * * * *

UNITED STATES PATENT AND TRADEMARK OFFICE
CERTIFICATE OF CORRECTION

| | | |
|---|---|---|
| PATENT NO. | : 8,053,553 B2 | Page 1 of 1 |
| APPLICATION NO. | : 12/115083 | |
| DATED | : November 8, 2011 | |
| INVENTOR(S) | : Stongin et al. | |

It is certified that error appears in the above-identified patent and that said Letters Patent is hereby corrected as shown below:

Title sheet, item (75) Inventors, replace "Robert Day, Lonchamp (CA)" with --Robert Day, Sherbrooke (CA)--

Signed and Sealed this
Nineteenth Day of June, 2012

David J. Kappos
*Director of the United States Patent and Trademark Office*

```
                        SEQUENCE LISTING

<160> NUMBER OF SEQ ID NOS: 373

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 1

Thr Pro Arg Glu Arg Arg Arg Lys Lys Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 2

Ala Pro Arg Glu Arg Arg Arg Lys Lys Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 3

Thr Ala Arg Glu Arg Arg Arg Lys Lys Arg
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 4

Thr Pro Ala Glu Arg Arg Arg Lys Lys Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 5

Thr Pro Arg Ala Arg Arg Arg Lys Lys Arg
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 6

Thr Pro Arg Glu Ala Arg Arg Lys Lys Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 7

Thr Pro Arg Glu Arg Ala Arg Lys Lys Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 8

Thr Pro Arg Glu Arg Arg Ala Lys Lys Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 9

Thr Pro Arg Glu Arg Arg Arg Ala Lys Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 10

Thr Pro Arg Glu Arg Arg Arg Lys Ala Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 11

Thr Pro Arg Glu Arg Arg Arg Lys Lys Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 12

Ala Ala Arg Glu Arg Arg Arg Lys Lys Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 13

Thr Ala Ala Glu Arg Arg Arg Lys Lys Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 14

Thr Pro Ala Ala Arg Arg Arg Lys Lys Arg
1               5                   10

<210> SEQ ID NO 15
<211> LENGTH: 10
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 15

Thr Pro Arg Ala Ala Arg Arg Lys Lys Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 16

Thr Pro Arg Glu Ala Ala Arg Lys Lys Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 17

Thr Pro Arg Glu Arg Ala Ala Lys Lys Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 18

Thr Pro Arg Glu Arg Arg Ala Ala Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 19

Thr Pro Arg Glu Arg Arg Arg Ala Ala Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 20

Thr Pro Arg Glu Arg Arg Arg Lys Ala Ala
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 21

Ala Ala Ala Glu Arg Arg Arg Lys Lys Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 22

Thr Pro Ala Ala Ala Arg Arg Lys Lys Arg
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 23

Thr Pro Arg Glu Ala Ala Ala Lys Lys Arg
1               5                   10

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (2)..(2)
<223> OTHER INFORMATION: Xaa = Any amino acid
<220> FEATURE:
<221> NAME/KEY: VARIANT
<222> LOCATION: (3)..(3)
<223> OTHER INFORMATION: Xaa = R or K

<400> SEQUENCE: 24

Arg Xaa Xaa Arg
1

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 25

Ala Pro Arg Glu Arg Arg Arg Lys Lys Arg Gly
1               5                   10

<210> SEQ ID NO 26
<211> LENGTH: 11
```

```
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 26

Thr Ala Arg Glu Arg Arg Arg Lys Lys Arg Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 27

Thr Pro Ala Glu Arg Arg Arg Lys Lys Arg Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 28

Thr Pro Arg Ala Arg Arg Arg Lys Lys Arg Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 29

Thr Pro Arg Glu Ala Arg Arg Lys Lys Arg Gly
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 30

Thr Pro Arg Glu Arg Ala Arg Lys Lys Arg Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 31

Thr Pro Arg Glu Arg Arg Ala Lys Lys Arg Gly
1               5                   10
```

```
<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 32

Thr Pro Arg Glu Arg Arg Arg Ala Lys Arg Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 33

Thr Pro Arg Glu Arg Arg Arg Lys Ala Arg Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 34

Thr Pro Arg Glu Arg Arg Arg Lys Lys Ala Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 35

Ala Ala Arg Glu Arg Arg Arg Lys Lys Arg Gly
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 36

Thr Ala Ala Glu Arg Arg Arg Lys Lys Arg Gly
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 37

Thr Pro Ala Ala Arg Arg Lys Lys Arg Gly
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 38

Thr Pro Arg Ala Ala Arg Arg Lys Lys Arg Gly
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 39

Thr Pro Arg Glu Ala Ala Arg Lys Lys Arg Gly
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 40

Thr Pro Arg Glu Arg Ala Ala Lys Lys Arg Gly
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 41

Thr Pro Arg Glu Arg Arg Ala Ala Lys Arg Gly
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 42

Thr Pro Arg Glu Arg Arg Arg Ala Ala Arg Gly
1               5                   10

<210> SEQ ID NO 43
<211> LENGTH: 11
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 43

Thr Pro Arg Glu Arg Arg Arg Lys Ala Ala Gly
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 44

Ala Ala Ala Glu Arg Arg Arg Lys Lys Arg Gly
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 45

Thr Pro Ala Ala Ala Arg Arg Lys Lys Arg Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 46

Thr Pro Arg Glu Ala Ala Ala Lys Lys Arg Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 47

Thr Pro Arg Glu Arg Arg Arg Lys Lys Arg Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 48

Ala Pro Arg Glu Arg Arg Arg Lys Lys Arg Val
1               5                   10
```

```
<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 49

Thr Ala Arg Glu Arg Arg Arg Lys Lys Arg Val
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 50

Thr Pro Ala Glu Arg Arg Arg Lys Lys Arg Val
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 51

Thr Pro Arg Ala Arg Arg Arg Lys Lys Arg Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 52

Thr Pro Arg Glu Ala Arg Arg Lys Lys Arg Val
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 53

Thr Pro Arg Glu Arg Ala Arg Lys Lys Arg Val
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 54
```

Thr Pro Arg Glu Arg Arg Ala Lys Lys Arg Val
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 55

Thr Pro Arg Glu Arg Arg Arg Ala Lys Arg Val
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 56

Thr Pro Arg Glu Arg Arg Arg Lys Ala Arg Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 57

Thr Pro Arg Glu Arg Arg Arg Lys Lys Ala Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 58

Ala Ala Arg Glu Arg Arg Arg Lys Lys Arg Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 59

Thr Ala Ala Glu Arg Arg Arg Lys Lys Arg Val
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: note =

Synthetic Construct

<400> SEQUENCE: 60

Thr Pro Ala Ala Arg Arg Lys Lys Arg Val
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 61

Thr Pro Arg Ala Ala Arg Arg Lys Lys Arg Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 62

Thr Pro Arg Glu Ala Ala Arg Lys Lys Arg Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 63

Thr Pro Arg Glu Arg Ala Ala Lys Lys Arg Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 64

Thr Pro Arg Glu Arg Arg Ala Ala Lys Arg Val
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 65

Thr Pro Arg Glu Arg Arg Arg Ala Ala Arg Val
1               5                   10

<210> SEQ ID NO 66
<211> LENGTH: 11

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 66

Thr Pro Arg Glu Arg Arg Arg Lys Ala Ala Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 67

Ala Ala Ala Glu Arg Arg Arg Lys Lys Arg Val
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 68

Thr Pro Ala Ala Ala Arg Arg Lys Lys Arg Val
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 69

Thr Pro Arg Glu Ala Ala Ala Lys Lys Arg Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 70

Thr Pro Arg Glu Arg Arg Arg Lys Lys Arg Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 71

Ala Pro Arg Glu Arg Arg Arg Lys Lys Arg Ser
1               5                   10
```

```
<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 72

Thr Ala Arg Glu Arg Arg Arg Lys Lys Arg Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 73

Thr Pro Ala Glu Arg Arg Arg Lys Lys Arg Ser
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 74

Thr Pro Arg Ala Arg Arg Arg Lys Lys Arg Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 75

Thr Pro Arg Glu Ala Arg Arg Lys Lys Arg Ser
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 76

Thr Pro Arg Glu Arg Ala Arg Lys Lys Arg Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 77

Thr Pro Arg Glu Arg Arg Ala Lys Lys Arg Ser
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 78

Thr Pro Arg Glu Arg Arg Arg Ala Lys Arg Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 79

Thr Pro Arg Glu Arg Arg Arg Lys Ala Arg Ser
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 80

Thr Pro Arg Glu Arg Arg Arg Lys Lys Ala Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 81

Ala Ala Arg Glu Arg Arg Arg Lys Lys Arg Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 82

Thr Ala Ala Glu Arg Arg Arg Lys Lys Arg Ser
1               5                   10

<210> SEQ ID NO 83
<211> LENGTH: 11
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 83

Thr Pro Ala Ala Arg Arg Lys Lys Arg Ser
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 84

Thr Pro Arg Ala Ala Arg Arg Lys Lys Arg Ser
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 85

Thr Pro Arg Glu Ala Ala Arg Lys Lys Arg Ser
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 86

Thr Pro Arg Glu Arg Ala Ala Lys Lys Arg Ser
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 87

Thr Pro Arg Glu Arg Arg Ala Ala Lys Arg Ser
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 88

Thr Pro Arg Glu Arg Arg Arg Ala Ala Arg Ser
1               5                   10
```

```
<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 89

Thr Pro Arg Glu Arg Arg Arg Lys Ala Ala Ser
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 90

Ala Ala Ala Glu Arg Arg Arg Lys Lys Arg Ser
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 91

Thr Pro Ala Ala Ala Arg Arg Lys Lys Arg Ser
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 92

Thr Pro Arg Glu Ala Ala Ala Lys Lys Arg Ser
1               5                   10

<210> SEQ ID NO 93
<211> LENGTH: 45
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 93

Arg Ser Leu Val Pro Arg Gly Ser Pro Gly Ser Gly Tyr Ile Pro Glu
1               5                   10                  15

Ala Pro Arg Asp Gly Gln Ala Tyr Val Arg Lys Asp Gly Glu Trp Val
            20                  25                  30

Leu Leu Ser Thr Phe Leu Gly His His His His His His
        35                  40                  45

<210> SEQ ID NO 94
<211> LENGTH: 11
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 94

Thr Pro Arg Gly Arg Arg Arg Lys Lys Arg Gly
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 95

Thr Pro Arg Val Arg Arg Arg Lys Lys Arg Gly
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 96

Thr Pro Arg Leu Arg Arg Arg Lys Lys Arg Gly
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 97

Thr Pro Arg Ile Arg Arg Arg Lys Lys Arg Gly
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 98

Thr Pro Arg Pro Arg Arg Arg Lys Lys Arg Gly
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 99

Thr Pro Arg Phe Arg Arg Arg Lys Lys Arg Gly
1               5                   10
```

```
<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 100

Thr Pro Arg Trp Arg Arg Arg Lys Lys Arg Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 101

Thr Pro Arg Met Arg Arg Arg Lys Lys Arg Gly
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 102

Thr Pro Arg Ser Arg Arg Arg Lys Lys Arg Gly
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 103

Thr Pro Arg Thr Arg Arg Arg Lys Lys Arg Gly
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 104

Thr Pro Arg Cys Arg Arg Arg Lys Lys Arg Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 105
```

Thr Pro Arg Tyr Arg Arg Arg Lys Lys Arg Gly
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 106

Thr Pro Arg Asn Arg Arg Arg Lys Lys Arg Gly
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 107

Thr Pro Arg Gln Arg Arg Arg Lys Lys Arg Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 108

Thr Pro Arg Asp Arg Arg Arg Lys Lys Arg Gly
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 109

Thr Pro Arg Glu Arg Arg Arg Lys Lys Arg Gly
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 110

Thr Pro Arg His Arg Arg Arg Lys Lys Arg Gly
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence:  note =

Synthetic Construct

<400> SEQUENCE: 111

Thr Pro Arg Lys Arg Arg Arg Lys Lys Arg Gly
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 112

Thr Pro Arg Lys Arg Arg Arg Lys Lys Arg Gly
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 113

Thr Pro Arg Arg Arg Arg Arg Lys Lys Arg Gly
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = bAla

<400> SEQUENCE: 114

Thr Pro Arg Xaa Arg Arg Arg Lys Lys Arg Gly
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = Epsilon-aminohexanoic acid

<400> SEQUENCE: 115

Thr Pro Arg Xaa Arg Arg Arg Lys Lys Arg Gly
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:

```
<221> NAME/KEY: VARIANT
<222> LOCATION: (4)..(4)
<223> OTHER INFORMATION: Xaa = Aminocylopenta carboxylic acid

<400> SEQUENCE: 116

Thr Pro Arg Xaa Arg Arg Arg Lys Lys Arg Gly
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = Citrullin

<400> SEQUENCE: 117

Thr Pro Arg Xaa Arg Arg Arg Lys Lys Arg Gly
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = D-Glu

<400> SEQUENCE: 118

Thr Pro Arg Xaa Arg Arg Arg Lys Lys Arg Gly
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = D-Lys

<400> SEQUENCE: 119

Thr Pro Arg Xaa Arg Arg Arg Lys Lys Arg Gly
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 120

Thr Pro Ala Glu Arg Arg Arg Lys Lys Arg Ala
1               5                   10

<210> SEQ ID NO 121
<211> LENGTH: 11
```

<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 121

Thr Pro Ala Glu Arg Arg Arg Lys Lys Arg Val
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 122

Thr Pro Ala Glu Arg Arg Arg Lys Lys Arg Leu
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 123

Thr Pro Ala Glu Arg Arg Arg Lys Lys Arg Ile
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 124

Thr Pro Ala Glu Arg Arg Arg Lys Lys Arg Pro
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 125

Thr Pro Ala Glu Arg Arg Arg Lys Lys Arg Phe
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 126

Thr Pro Ala Glu Arg Arg Arg Lys Lys Arg Trp
1               5                   10

```
<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 127

Thr Pro Ala Glu Arg Arg Arg Lys Lys Arg Met
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 128

Thr Pro Ala Glu Arg Arg Arg Lys Lys Arg Ser
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 129

Thr Pro Ala Glu Arg Arg Arg Lys Lys Arg Thr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 130

Thr Pro Ala Glu Arg Arg Arg Lys Lys Arg Cys
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 131

Thr Pro Ala Glu Arg Arg Arg Lys Lys Arg Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 132

Thr Pro Ala Glu Arg Arg Arg Lys Lys Arg Asn
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 133

Thr Pro Ala Glu Arg Arg Arg Lys Lys Arg Gln
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 134

Thr Pro Ala Glu Arg Arg Arg Lys Lys Arg Asp
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 135

Thr Pro Ala Glu Arg Arg Arg Lys Lys Arg Glu
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 136

Thr Pro Ala Glu Arg Arg Arg Lys Lys Arg His
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 137

Thr Pro Ala Glu Arg Arg Arg Lys Lys Arg Lys
1               5                   10

<210> SEQ ID NO 138
<211> LENGTH: 11
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 138

Thr Pro Ala Glu Arg Arg Arg Lys Lys Arg Arg
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (11)..(11)
<223> OTHER INFORMATION: Xaa = Cys(Me)

<400> SEQUENCE: 139

Thr Pro Ala Glu Arg Arg Arg Lys Lys Arg Xaa
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (11)..(11)
<223> OTHER INFORMATION: Xaa = Norleucine

<400> SEQUENCE: 140

Thr Pro Ala Glu Arg Arg Arg Lys Lys Arg Xaa
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 141

Thr Pro Gln Arg Ala Arg Arg Arg Lys Lys Arg Gly
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 142

Thr Pro Gln Arg Ala Arg Arg Arg Lys Lys Arg Ala
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence:  note =
```

```
Synthetic Construct

<400> SEQUENCE: 143

Thr Pro Gln Arg Ala Arg Arg Arg Lys Lys Arg Val
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 144

Thr Pro Gln Arg Ala Arg Arg Arg Lys Lys Arg Leu
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 145

Thr Pro Gln Arg Ala Arg Arg Arg Lys Lys Arg Ile
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 146

Thr Pro Gln Arg Ala Arg Arg Arg Lys Lys Arg Pro
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 147

Thr Pro Gln Arg Ala Arg Arg Arg Lys Lys Arg Phe
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 148

Thr Pro Gln Arg Ala Arg Arg Arg Lys Lys Arg Trp
1               5                   10

<210> SEQ ID NO 149
<211> LENGTH: 12
```

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 149

Thr Pro Gln Arg Ala Arg Arg Arg Lys Lys Arg Met
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 150

Thr Pro Gln Arg Ala Arg Arg Arg Lys Lys Arg Ser
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 151

Thr Pro Gln Arg Ala Arg Arg Arg Lys Lys Arg Thr
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 152

Thr Pro Gln Arg Ala Arg Arg Arg Lys Lys Arg Cys
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 153

Thr Pro Gln Arg Ala Arg Arg Arg Lys Lys Arg Tyr
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 154

Thr Pro Gln Arg Ala Arg Arg Arg Lys Lys Arg Asn
1               5                   10
```

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 155

Thr Pro Gln Arg Ala Arg Arg Arg Lys Lys Arg Gln
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 156

Thr Pro Gln Arg Ala Arg Arg Arg Lys Lys Arg Asp
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 157

Thr Pro Gln Arg Ala Arg Arg Arg Lys Lys Arg Glu
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 158

Thr Pro Gln Arg Ala Arg Arg Arg Lys Lys Arg His
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 159

Thr Pro Gln Arg Ala Arg Arg Arg Lys Lys Arg Lys
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

```
<400> SEQUENCE: 160

Thr Pro Gln Arg Ala Arg Arg Arg Lys Lys Arg Arg
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = bAla

<400> SEQUENCE: 161

Thr Pro Gln Arg Ala Arg Arg Arg Lys Lys Arg Xaa
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = Epsilon-aminohexanoic acid

<400> SEQUENCE: 162

Thr Pro Gln Arg Ala Arg Arg Arg Lys Lys Arg Xaa
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = Amino cylopentacaroxylic acid

<400> SEQUENCE: 163

Thr Pro Gln Arg Ala Arg Arg Arg Lys Lys Arg Xaa
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = Cys(Me)

<400> SEQUENCE: 164

Thr Pro Gln Arg Ala Arg Arg Arg Lys Lys Arg Xaa
1               5                   10

<210> SEQ ID NO 165
<211> LENGTH: 12
```

```
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = Norleucine

<400> SEQUENCE: 165

Thr Pro Gln Arg Ala Arg Arg Arg Lys Lys Arg Xaa
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = D-Lys

<400> SEQUENCE: 166

Thr Pro Gln Arg Ala Arg Arg Arg Lys Lys Arg Xaa
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
<223> OTHER INFORMATION: Xaa = D-Arg

<400> SEQUENCE: 167

Thr Pro Gln Arg Ala Arg Arg Arg Lys Lys Arg Xaa
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (11)..(11)
<223> OTHER INFORMATION: Xaa = D-Arg

<400> SEQUENCE: 168

Thr Pro Gln Arg Ala Arg Arg Arg Lys Lys Xaa Gly
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: note =
      Synthetic Construct
<220> FEATURE:
<221> NAME/KEY: VARIANT
<222> LOCATION: (12)..(12)
```

<223> OTHER INFORMATION: Xaa = Citrullin

<400> SEQUENCE: 169

Thr Pro Gln Arg Ala Arg Arg Arg Lys Lys Xaa Gly
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 170

Thr Pro Gln Arg Ala Arg Arg Arg Lys Lys Gly
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 171

Thr Pro Gln Arg Ala Arg Arg Arg Lys Lys Arg Gly
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 172

Thr Pro Gln Arg Cys Arg Arg Arg Lys Lys Arg Gly
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 173

Thr Pro Gln Arg Asp Arg Arg Arg Lys Lys Arg Gly
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 174

Thr Pro Gln Arg Glu Arg Arg Arg Lys Lys Arg Gly
1               5                   10

<210> SEQ ID NO 175
<211> LENGTH: 12

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 175

Thr Pro Gln Arg Phe Arg Arg Arg Lys Lys Arg Gly
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 176

Thr Pro Gln Arg Gly Arg Arg Arg Lys Lys Arg Gly
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 177

Thr Pro Gln Arg His Arg Arg Arg Lys Lys Arg Gly
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 178

Thr Pro Gln Arg Ile Arg Arg Arg Lys Lys Arg Gly
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 179

Thr Pro Gln Arg Lys Arg Arg Arg Lys Lys Arg Gly
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 180

Thr Pro Gln Arg Leu Arg Arg Arg Lys Lys Arg Gly
1               5                   10
```

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 181

Thr Pro Gln Arg Met Arg Arg Arg Lys Lys Arg Gly
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 182

Thr Pro Gln Arg Asn Arg Arg Arg Lys Lys Arg Gly
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 183

Thr Pro Gln Arg Pro Arg Arg Arg Lys Lys Arg Gly
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 184

Thr Pro Gln Arg Gln Arg Arg Arg Lys Lys Arg Gly
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 185

Thr Pro Gln Arg Arg Arg Arg Arg Lys Lys Arg Gly
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

```
<400> SEQUENCE: 186

Thr Pro Gln Arg Ser Arg Arg Arg Lys Lys Arg Gly
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 187

Thr Pro Gln Arg Thr Arg Arg Arg Lys Lys Arg Gly
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 188

Thr Pro Gln Arg Val Arg Arg Arg Lys Lys Arg Gly
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 189

Thr Pro Gln Arg Trp Arg Arg Arg Lys Lys Arg Gly
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 190

Thr Pro Gln Arg Tyr Arg Arg Arg Lys Lys Arg Gly
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = bAla

<400> SEQUENCE: 191

Thr Pro Gln Arg Xaa Arg Arg Arg Lys Lys Arg Gly
1               5                   10
```

```
<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = Epsilon - aminohexanoic acid

<400> SEQUENCE: 192

Thr Pro Gln Arg Xaa Arg Arg Arg Lys Lys Arg Gly
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa =Aminocylopenta carboxylic acid

<400> SEQUENCE: 193

Thr Pro Gln Arg Xaa Arg Arg Arg Lys Lys Arg Gly
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = Citrullin

<400> SEQUENCE: 194

Thr Pro Gln Arg Xaa Arg Arg Arg Lys Lys Arg Gly
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = D-Glu

<400> SEQUENCE: 195

Thr Pro Gln Arg Xaa Arg Arg Arg Lys Lys Arg Gly
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
```

```
<221> NAME/KEY: VARIANT
<222> LOCATION: (5)..(5)
<223> OTHER INFORMATION: Xaa - D-Lys

<400> SEQUENCE: 196

Thr Pro Gln Arg Xaa Arg Arg Arg Lys Lys Arg Gly
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = D-Arg

<400> SEQUENCE: 197

Thr Pro Gln Arg Xaa Arg Arg Arg Lys Lys Arg Gly
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = Cys(Me)

<400> SEQUENCE: 198

Thr Pro Gln Arg Xaa Arg Arg Lys Lys Arg Gly
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = Norleucine

<400> SEQUENCE: 199

Thr Pro Gln Arg Xaa Arg Arg Lys Lys Arg Gly
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (5)..(5)
<223> OTHER INFORMATION: Xaa = cyclohexalanine

<400> SEQUENCE: 200

Thr Pro Gln Arg Xaa Arg Arg Arg Lys Lys Arg Gly
1               5                   10
```

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence:  note = Synthetic Construct
<220> FEATURE:
<221> NAME/KEY: VARIANT
<222> LOCATION: (5)..(5)
<223> OTHER INFORMATION: Xaa = d-amino-butyric acid

<400> SEQUENCE: 201

Thr Pro Gln Arg Xaa Arg Arg Arg Lys Lys Arg Gly
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence:  note = Synthetic Construct
<220> FEATURE:
<221> NAME/KEY: VARIANT
<222> LOCATION: (5)..(5)
<223> OTHER INFORMATION: Xaa = Citrullin
<220> FEATURE:
<221> NAME/KEY: VARIANT
<222> LOCATION: (11)..(11)
<223> OTHER INFORMATION: Xaa = Citrullin

<400> SEQUENCE: 202

Thr Pro Gln Arg Xaa Arg Arg Lys Lys Gly Xaa
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence:  note = Synthetic Construct

<400> SEQUENCE: 203

Thr Pro Arg Ala Arg Arg Arg Lys Lys Arg Ala
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence:  note = Synthetic Construct

<400> SEQUENCE: 204

Thr Pro Arg Ala Arg Arg Arg Lys Lys Arg Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence:  note = Synthetic Construct

<400> SEQUENCE: 205

```
Thr Pro Arg Ala Arg Arg Arg Lys Lys Arg Leu
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 206

Thr Pro Arg Ala Arg Arg Arg Lys Lys Arg Ile
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 207

Thr Pro Arg Ala Arg Arg Arg Lys Lys Arg Pro
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 208

Thr Pro Arg Ala Arg Arg Arg Lys Lys Arg Phe
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 209

Thr Pro Arg Ala Arg Arg Arg Lys Lys Arg Trp
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 210

Thr Pro Arg Ala Arg Arg Arg Lys Lys Arg Met
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: note =
```

Synthetic Construct

<400> SEQUENCE: 211

Thr Pro Arg Ala Arg Arg Arg Lys Lys Arg Ser
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 212

Thr Pro Arg Ala Arg Arg Arg Lys Lys Arg Thr
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 213

Thr Pro Arg Ala Arg Arg Arg Lys Lys Arg Cys
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 214

Thr Pro Arg Ala Arg Arg Arg Lys Lys Arg Tyr
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 215

Thr Pro Arg Ala Arg Arg Arg Lys Lys Arg Asn
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 216

Thr Pro Arg Ala Arg Arg Arg Lys Lys Arg Gln
1               5                   10

<210> SEQ ID NO 217
<211> LENGTH: 11

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 217

Thr Pro Arg Ala Arg Arg Arg Lys Lys Arg Asp
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 218

Thr Pro Arg Ala Arg Arg Arg Lys Lys Arg Glu
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 219

Thr Pro Arg Ala Arg Arg Arg Lys Lys Arg His
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 220

Thr Pro Arg Ala Arg Arg Arg Lys Lys Arg Lys
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 221

Thr Pro Arg Ala Arg Arg Arg Lys Lys Arg Arg
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (11)..(11)
<223> OTHER INFORMATION: Xaa = Cys (Me)
```

```
<400> SEQUENCE: 222

Thr Pro Arg Ala Arg Arg Arg Lys Lys Arg Xaa
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (11)..(11)
<223> OTHER INFORMATION: Xaa = Norleucine

<400> SEQUENCE: 223

Thr Pro Arg Ala Arg Arg Arg Lys Lys Arg Xaa
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 224

Thr Pro Gln Arg Glu Arg Arg Arg Lys Lys Arg Gly Leu
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (11)..(11)
<223> OTHER INFORMATION: Xaa = F, W, T or Y

<400> SEQUENCE: 225

Thr Pro Arg Ala Arg Arg Arg Lys Lys Arg Xaa
1               5                   10

<210> SEQ ID NO 226
<211> LENGTH: 3
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 226

Gly Gly Gly
1

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 227
```

```
Gly Gly Gly Gly Gly Gly
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 228

Gly Ala Gly Ala Gly Ala
1               5

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 229

Arg Gly Val Thr Lys Arg Ser Leu Ser Pro
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 230

Lys Arg Arg Thr Lys Arg Asp Val Tyr Gln
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 231

Val Met Lys Gln Lys Arg Cys Gly Val Pro
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 232

Thr Met Arg Lys Pro Arg Cys Gly Asn Pro
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence:  note =
```

-continued

Synthetic Construct

<400> SEQUENCE: 233

Val Met Arg Lys Pro Arg Cys Gly Val Pro
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 234

Met Met Lys Lys Pro Arg Cys Gly Val Pro
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 235

Ala Met Arg Thr Pro Arg Cys Gly Val Pro
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 236

Val Met Arg Lys Pro Arg Cys Gly Val Pro
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 237

Arg Asn Arg Gln Lys Arg Phe Val Leu Ser
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 238

Val Met Lys Lys Pro Arg Cys Gly Val Pro
1               5                   10

<210> SEQ ID NO 239
<211> LENGTH: 10

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 239

Asn Val Arg Arg Lys Arg Tyr Ala Ile Gln
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 240

Arg Arg Arg Arg Lys Arg Tyr Ala Leu Thr
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 241

His Ile Arg Arg Lys Arg Tyr Ala Leu Thr
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 242

Gln Ala Arg Arg Arg Arg Gln Ala Pro Ala
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 243

Arg Arg Arg Asn Lys Arg Tyr Ala Leu Thr
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 244

Val Arg Arg Arg Arg Arg Tyr Ala Leu Ser
1               5                   10
```

```
<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 245

Arg Ala Arg Ser Arg Arg Ser Pro Arg Ala
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 246

Met Arg Arg Lys Arg Arg Phe Ala Lys Gln
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 247

Pro Pro Arg Ser Arg Lys Pro Asp Asp Leu
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 248

Pro Ser Arg Glu Thr Arg Tyr Val Glu Leu
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 249

Leu Leu Arg Arg Arg Arg Ala Val Leu Glu
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct
```

-continued

```
<400> SEQUENCE: 250

Leu Leu Arg Lys Lys Arg Thr Thr Ser Ala
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 251

Ala Arg Arg His Lys Arg Glu Thr Leu Lys
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 252

His Ile Arg Arg Arg Arg Asp Val Val Thr
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 253

Val His Arg Val Lys Arg Arg Ala Asp Pro
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 254

Pro Arg Arg Met Lys Arg Glu Asp Leu Asn
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 255

Ser Ile Arg Lys Lys Arg Phe Val Ser Ser
1               5                   10

<210> SEQ ID NO 256
<211> LENGTH: 10
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 256

Gly Val Arg Ala Arg Arg Ala Ala Pro Ala
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 257

Arg Arg Arg Ala Arg Arg His Ala Ala Asp
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 258

Thr Met Arg Arg Arg Arg His Ala Gly Glu
1               5                   10

<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 259

Pro Arg Arg Ala Lys Arg Phe Ala Ser Leu
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 260

Trp Arg Arg Arg Arg Arg Ser Ile Ser Arg
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 261

Arg Gln Arg Gln Arg Arg Ala Ala Gly Gly
1               5                   10
```

```
<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 262

Arg Ser Arg Ser Arg Arg Ala Ala Thr Ser
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 263

Arg Arg Arg Ala Lys Arg Ser Pro Lys His
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 264

Pro Ser Arg Gln Lys Arg Ser Val Glu Asn
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 265

Gly Leu Arg Leu Pro Arg Glu Thr Asp Glu
1               5                   10

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 266

Arg Gly Val Phe Arg Arg Asp Ala His Lys
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 267
```

Ser His Arg Ser Lys Arg Ser Leu Ser Cys
1               5                   10

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 268

Leu Asn Arg Pro Lys Arg Tyr Asn Ser Gly
1               5                   10

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 269

Arg Ser His Leu Lys Arg Asp Thr Glu Asp
1               5                   10

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 270

Arg Gly Arg Lys Arg Arg Ser Thr Asn Glu
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 271

Ala Ser Arg Asn Arg Arg His Val Thr Glu
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 272

Gln Arg Arg Lys Arg Arg Ser Val Asn Pro
1               5                   10

<210> SEQ ID NO 273
<211> LENGTH: 5
<212> TYPE: PRT
<213> ORGANISM: Artificial Sequence
<220> FEATURE:
<223> OTHER INFORMATION: Description of Artificial Sequence: note =

Synthetic Construct
<220> FEATURE:
<221> NAME/KEY: VARIANT
<222> LOCATION: (1)..(1)
<223> OTHER INFORMATION: Xaa = Pyroglutamic acid

<400> SEQUENCE: 273

Xaa Arg Thr Lys Arg
1               5

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 274

Pro Gln Arg Arg Arg Arg Gln Leu Asp Pro
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 275

His Val Ile Ser Lys Arg Ser Thr Glu Glu
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 276

His His Gln Gln Lys Arg Glu Ala Pro Ser
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 277

Asn Ser Arg Lys Lys Arg Glu Ile Thr Glu
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 278

Arg Asp Arg Arg Arg Arg Glu Leu Glu Pro
1               5                   10

```
<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 279

His Leu Val Arg Lys Arg Asp Val His Val
1               5                   10

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 280

His Leu Ile Thr Lys Arg Asp Leu Ala Leu
1               5                   10

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 281

His Lys Arg Asp Arg Arg Gln Ile Phe Leu
1               5                   10

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 282

Ser Asn Arg His Arg Arg Gln Ile Asp Arg
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 283

Gly Gly Arg Arg Arg Arg Glu Leu Asp Pro
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 284

Pro Ser Arg Lys Arg Arg Ser Leu Gly Asp
1               5                   10

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 285

Lys Arg Arg Gln Lys Arg Glu Trp Val Lys
1               5                   10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 286

Leu Gln Arg Gln Lys Arg Ser Ile Asn Leu
1               5                   10

<210> SEQ ID NO 287
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 287

Pro Leu Arg Arg Lys Arg Ser Ala Ala Leu
1               5                   10

<210> SEQ ID NO 288
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 288

Glu Lys Arg Lys Lys Arg Ser Thr Lys Lys
1               5                   10

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 289

Pro Ala Lys Ser Ala Arg Ser Val Arg Ala
1               5                   10

<210> SEQ ID NO 290
<211> LENGTH: 10
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 290

Pro Ala Lys Ser Glu Arg Asp Val Ser Thr
1               5                   10

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 291

Pro Ile Arg Arg Lys Arg Ser Ile Glu Glu
1               5                   10

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 292

Leu Ala Arg Gly Arg Arg Ser Leu Gly Ser
1               5                   10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 293

Leu Ala Arg Gly Arg Arg Ser Leu Gly Ser
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 294

Phe Gly Arg Lys Ser Arg Val Val Asp Leu
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 295

His Asp Arg Lys Ser Lys Val Asp Leu Asp
1               5                   10
```

```
<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 296

His Asp Arg Lys Ser Lys Val Asp Leu Asp
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 297

Thr Ser Arg Arg Lys Arg Tyr Ala Glu His
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 298

Ala Asn Arg Ser Arg Arg Gly Val Ser Glu
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 299

His Ser Ile Ile Arg Arg Ser Leu Pro Ala
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 300

Tyr Ser Ile Ile Arg Arg Ser Ile Gln Ile
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 301
```

-continued

Pro Arg Arg His Thr Arg Ser Ala Glu Asp
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 302

Thr Leu Arg Ala Pro Arg Ser Pro Lys Met
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 303

Lys Ser Val Lys Lys Arg Ser Val Ser Glu
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 304

Ser Ser Arg His Arg Arg Ala Leu Asp Thr
1               5                   10

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 305

Arg Ser Arg Lys Arg Arg Ala Val Leu Thr
1               5                   10

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 306

Val Arg Arg Asn Lys Arg Ser Lys Ser Asn
1               5                   10

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: note =

Synthetic Construct

<400> SEQUENCE: 307

Thr His Arg Ser Lys Arg Ser Ser His
1               5                  10

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 308

Lys Arg Arg Thr Arg Arg Gln Asp Ile Arg
1               5                  10

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 309

Leu Arg Arg Ser Lys Arg Cys Ser Cys Ser
1               5                  10

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 310

Ser Arg Arg Leu Lys Arg Ala Val Ser Glu
1               5                  10

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 311

Arg Ser Arg Gly Lys Arg Phe Ser Gln Ser
1               5                  10

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 312

Ser Met Arg Val Arg Arg His Ser Asp Pro
1               5                  10

<210> SEQ ID NO 313
<211> LENGTH: 10

```
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 313

Arg Ser Arg Lys Arg Arg Ala Val Leu Thr
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 314

Asn Ser Arg Asn Lys Arg Ala Val Gln Gly
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 315

Arg Asp Arg Lys Val Arg Asp Leu Gln Glu
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 316

Lys Thr Lys Gln Leu Arg Val Val Asn Gly
1               5                   10

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 317

Pro Arg Tyr Gly Lys Arg His Lys Glu Asp
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 318

Ala Ser His His Arg Arg Gln Leu Gly Pro
1               5                   10
```

```
<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 319

Gly Gly Phe Met Lys Lys Asp Ala Glu Glu
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 320

Met Arg Gly Leu Lys Arg Ser Pro Gln Leu
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 321

Gly Gly Phe Leu Lys Arg Phe Ala Glu Ala
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 322

Trp Asp Asn Gln Lys Arg Tyr Gly Gly Phe
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 323

Phe Leu Arg Arg Ile Arg Pro Lys Leu Lys
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct
```

```
<400> SEQUENCE: 324

Val Gly Lys Lys Arg Arg Pro Val Lys Val
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 325

Pro Pro Lys Asp Lys Arg Tyr Gly Gly Phe
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 326

Pro Leu Glu Phe Lys Arg Glu Leu Thr Gly
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 327

Arg Arg Arg Lys Lys Arg Gly Leu Phe Gly
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 328

Gly Arg Arg Gln Lys Arg Leu Ile Gly Ala
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 329

Asp Pro Arg Thr Lys Arg Phe Phe Gly Gly
1               5                   10

<210> SEQ ID NO 330
<211> LENGTH: 10
<212> TYPE: PRT
<213> ORGANISM: Artificial Sequence
```

```
<220> FEATURE:
<223> OTHER INFORMATION: Description of Artificial Sequence:  note =
      Synthetic Construct

<400> SEQUENCE: 330

Ser Gly Arg Ser Lys Arg Ser Val Ile Asp
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 331

His Arg Arg Glu Lys Arg Ser Val Ala Leu
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 332

Ser Arg Arg Ser Arg Arg Ser Leu Thr Val
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 333

Thr His Arg Thr Lys Arg Ser Thr Asp Gly
1               5                   10

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 334

Val Gln Arg Glu Lys Arg Ala Val Gly Leu
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 335

Ser Arg Arg His Lys Arg Phe Ala Gly Val
1               5                   10
```

```
<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 336

Thr Arg Arg Phe Arg Arg Ser Ile Thr Glu
1               5                   10

<210> SEQ ID NO 337
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 337

Tyr Phe Arg Arg Lys Arg Ser Ile Leu Trp
1               5                   10

<210> SEQ ID NO 338
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 338

Gly Arg Arg Thr Arg Arg Glu Ala Ile Val
1               5                   10

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 339

Leu Arg Arg Arg Arg Arg Asp Ala Gly Asn
1               5                   10

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 340

Arg His Arg Gln Pro Arg Gly Trp Glu Gln
1               5                   10

<210> SEQ ID NO 341
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 341
```

```
Asn Ser Arg Lys Lys Arg Ser Thr Ser Ala
1               5                   10

<210> SEQ ID NO 342
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 342

Lys Arg Arg Gly Lys Arg Ser Val Asp Ser
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 343

Gly Asn Arg Val Arg Arg Ser Val Gly Ser
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 344

Lys Val Arg Arg Ala Arg Ser Val Asp Gly
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 345

Ala Ser Arg Val Ala Arg Met Ala Ser Asp
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence:  note =
      Synthetic Construct
<220> FEATURE:
<221> NAME/KEY: VARIANT
<222> LOCATION: (4)..(4)
<223> OTHER INFORMATION: Xaa = A or G
<220> FEATURE:
<221> NAME/KEY: VARIANT
<222> LOCATION: (11)..(11)
<223> OTHER INFORMATION: Xaa = any amino acid

<400> SEQUENCE: 346

Thr Pro Arg Xaa Arg Arg Arg Lys Lys Arg Xaa
1               5                   10
```

```
<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 347

Arg Gln Pro Lys Ile Trp Phe Pro Asn Arg Arg Lys Pro Trp Lys Lys
1               5                   10                  15

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 348

Gly Arg Lys Lys Arg Arg Gln Arg Pro Pro Gln
1               5                   10

<210> SEQ ID NO 349
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 349

Arg Gln Ile Lys Ile Trp Phe Gln Asn Arg Arg Met Lys Trp Lys Lys
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 350

Arg Gln Ile Ala Ile Trp Phe Gln Asn Arg Arg Met Lys Trp Ala Ala
1               5                   10                  15

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 351

Arg Lys Lys Arg Arg Gln Arg Arg Arg
1               5

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: note =
      Synthetic Construct
```

-continued

<400> SEQUENCE: 352

Thr Arg Ser Ser Arg Ala Gly Leu Gln Phe Pro Val Gly Arg Val His
1               5                   10                  15

Arg Leu Leu Arg Lys
            20

<210> SEQ ID NO 353
<211> LENGTH: 26
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 353

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 354
<211> LENGTH: 18
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 354

Lys Leu Ala Leu Lys Leu Ala Leu Lys Ala Leu Lys Ala Ala Leu Lys
1               5                   10                  15

Leu Ala

<210> SEQ ID NO 355
<211> LENGTH: 16
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 355

Ala Ala Val Ala Leu Leu Pro Ala Val Leu Leu Ala Leu Leu Ala Pro
1               5                   10                  15

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 356

Val Pro Met Leu Lys Pro Met Leu Lys Glu
1               5                   10

<210> SEQ ID NO 357
<211> LENGTH: 28
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 357

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25
```

<210> SEQ ID NO 358
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 358

```
Leu Leu Ile Ile Leu Arg Arg Arg Ile Arg Lys Gln Ala His Ala His
1               5                   10                  15

Ser Lys
```

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 359

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 360
<211> LENGTH: 18
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 360

```
Arg Gly Gly Arg Leu Ser Tyr Ser Arg Arg Arg Phe Ser Thr Ser Thr
1               5                   10                  15

Gly Arg
```

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 361

```
Ser Asp Leu Trp Glu Met Met Met Val Ser Leu Ala Cys Gln Tyr
1               5                   10                  15
```

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 362

```
Thr Ser Pro Leu Asn Ile His Asn Gly Gln Lys Leu
1               5                   10

<210> SEQ ID NO 363
<211> LENGTH: 794
<212> TYPE: PRT
<213> ORGANISM: Artificial Sequence
<220> FEATURE:
<223> OTHER INFORMATION: Description of Artificial Sequence:  note =
      Synthetic Construct

<400> SEQUENCE: 363

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350
```

```
Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
                420                 425                 430

Ala Met Val Ala Leu Ala Gln Asn Trp Thr Thr Val Ala Pro Gln Arg
                435                 440                 445

Lys Cys Ile Ile Asp Ile Leu Thr Glu Pro Lys Asp Ile Gly Lys Arg
        450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
                500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
        530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
                580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
        610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
                660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
        690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
                740                 745                 750

Asp Arg Gly Leu Ile Ser Tyr Lys Gly Leu Pro Pro Glu Ala Trp Gln
                755                 760                 765
```

-continued

Glu Glu Cys Pro Ser Asp Ser Glu Glu Asp Glu Gly Arg Gly Glu Arg
        770                 775                 780

Thr Ala Phe Ile Lys Asp Gln Ser Ala Leu
785                 790

<210> SEQ ID NO 364
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 364

Arg Thr Lys Arg
1

<210> SEQ ID NO 365
<211> LENGTH: 10
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 365

Pro Arg Ala Arg Arg Lys Lys Arg Thr
1               5                   10

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 366

Arg Ala Arg Arg Arg Lys Lys Arg Thr
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 367

Ala Arg Arg Arg Lys Lys Arg Thr
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 368

Arg Arg Arg Lys Lys Arg Thr
1               5

```
<210> SEQ ID NO 369
<211> LENGTH: 6
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 369

Arg Arg Lys Lys Arg Thr
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 370

Arg Lys Lys Arg Thr
1               5

<210> SEQ ID NO 371
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: X = A or G

<400> SEQUENCE: 371

Thr Pro Arg Xaa Arg Arg Arg Lys Lys Arg
1               5                   10

<210> SEQ ID NO 372
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X = A or G
<220> FEATURE:
<221> NAME/KEY: MISC_FEATURE
<222> LOCATION: (12)..(12)
<223> OTHER INFORMATION: X = any amino acid

<400> SEQUENCE: 372

Thr Pro Gln Arg Xaa Arg Arg Arg Lys Lys Arg Xaa
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: X = A or G
```

```
<400> SEQUENCE: 373

Thr Pro Gln Arg Xaa Arg Arg Arg Lys Lys Arg
1               5                   10
```